(12) United States Patent
Pesce et al.

(10) Patent No.: US 11,833,047 B2
(45) Date of Patent: Dec. 5, 2023

(54) HEART VALVE SUPPORT DEVICE AND METHODS FOR MAKING AND USING THE SAME

(71) Applicant: TriFlo Cardiovascular Inc., Newport Beach, CA (US)

(72) Inventors: Luca Pesce, Huntington Beach, CA (US); Alfonso Ussia, Rome (IT)

(73) Assignee: TriFlo Cardiovascular Inc., Newport Beach, CA (US)

( * ) Notice: Subject to any disclaimer, the term of this patent is extended or adjusted under 35 U.S.C. 154(b) by 325 days.

(21) Appl. No.: 16/712,832

(22) Filed: Dec. 12, 2019

(65) Prior Publication Data

US 2020/0113679 A1 Apr. 16, 2020

Related U.S. Application Data

(63) Continuation of application No. 15/850,255, filed on Dec. 21, 2017, now Pat. No. 10,765,518.
(Continued)

(51) Int. Cl.
*A61F 2/24* (2006.01)

(52) U.S. Cl.
CPC ............ *A61F 2/246* (2013.01); *A61F 2/2409* (2013.01); *A61F 2/2418* (2013.01); *A61F 2/2436* (2013.01);
(Continued)

(58) Field of Classification Search
CPC .......... A61F 2/24; A61F 2/246; A61F 2/2409; A61F 2/2418
See application file for complete search history.

(56) References Cited

U.S. PATENT DOCUMENTS

| 5,954,766 A | 9/1999 | Zadno Azizi et al. |
| 6,048,189 A | 4/2000 | Kurihara et al. |
| (Continued) | | |

FOREIGN PATENT DOCUMENTS

| CN | 102781371 A | 11/2012 |
| CN | 104994811 A | 10/2015 |
| (Continued) | | |

OTHER PUBLICATIONS

Pesce et al.; U.S. Appl. No. 16/882,226 entitled "Heart valve support device," filed May 22, 2020.
(Continued)

*Primary Examiner* — Matthew W Schall
(74) *Attorney, Agent, or Firm* — Shay Glenn LLP

(57) ABSTRACT

The disclosure relates to a device for supporting functions of a heart valve and methods for making and using the same. The device includes a flow optimizer configured to be located in the valve and having a cross sectional area that reduces a regurgitation orifice of the valve during systole. The device includes an anchoring mechanism coupled to the flow optimizer and configured to fix a position of the flow optimizer relative to the valve. The flow optimizer allows hemodynamic flow during diastole, minimizing risk of inducing atrioventricular pressure gradient and thrombogenesis, and seals or minimizes the regurgitation orifice during systole and reinstates efficacy of the valve. The anchoring system requires no traumatic interaction with the valve, atrium and ventricle. Implantation of the device can be achieved without invasive surgery. The device permits intraprocedural optimization of the positioning of the flow optimizer.

18 Claims, 48 Drawing Sheets

Related U.S. Application Data

(60) Provisional application No. 62/437,523, filed on Dec. 21, 2016.

(52) U.S. Cl.
CPC ..... *A61F 2/2466* (2013.01); *A61F 2210/0014* (2013.01); *A61F 2220/0008* (2013.01); *A61F 2220/0016* (2013.01)

(56) References Cited

U.S. PATENT DOCUMENTS

| | | | |
|---|---|---|---|
| 6,569,198 | B1 | 5/2003 | Wilson et al. |
| 6,764,510 | B2 | 7/2004 | Vidlund et al. |
| 6,797,002 | B2 | 9/2004 | Spence et al. |
| 6,848,440 | B2 | 2/2005 | Han et al. |
| 7,611,534 | B2 | 11/2009 | Kapadia et al. |
| 7,704,277 | B2 | 4/2010 | Zakay et al. |
| 7,789,909 | B2 | 9/2010 | Andersen et al. |
| 7,854,762 | B2 | 12/2010 | Speziali et al. |
| 7,901,454 | B2 | 3/2011 | Kapadia et al. |
| 8,092,525 | B2 | 1/2012 | Eliasen et al. |
| 8,109,996 | B2 | 2/2012 | Stacchino et al. |
| 8,377,115 | B2 | 2/2013 | Thompson |
| 8,408,214 | B2 | 4/2013 | Spenser |
| 8,449,599 | B2 | 5/2013 | Chau et al. |
| 8,470,028 | B2 | 6/2013 | Thornton et al. |
| 8,475,525 | B2 | 7/2013 | Maisano et al. |
| 8,597,347 | B2 | 12/2013 | Maurer et al. |
| 8,641,757 | B2 | 2/2014 | Pintor et al. |
| 8,778,017 | B2 | 7/2014 | Eliasen et al. |
| 8,932,348 | B2 | 1/2015 | Solem et al. |
| 8,961,596 | B2 | 2/2015 | Maisano et al. |
| 9,011,523 | B2 | 4/2015 | Seguin |
| 9,161,837 | B2 | 10/2015 | Kapadia |
| 9,232,998 | B2 | 1/2016 | Wilson et al. |
| 9,232,999 | B2 | 1/2016 | Maurer et al. |
| 9,241,702 | B2 | 1/2016 | Maisano et al. |
| 9,307,980 | B2 | 4/2016 | Gilmore et al. |
| 9,414,918 | B2 | 8/2016 | Chau et al. |
| 9,474,605 | B2 | 10/2016 | Rowe et al. |
| 9,504,570 | B2 | 11/2016 | Hauser et al. |
| 9,629,720 | B2 | 4/2017 | Nguyen et al. |
| 9,636,223 | B2 | 5/2017 | Khalil et al. |
| 9,750,604 | B2 | 9/2017 | Naor |
| 9,827,099 | B2 | 11/2017 | Mathis et al. |
| 10,195,033 | B2 | 2/2019 | Tuval et al. |
| 10,238,490 | B2 | 3/2019 | Gifford |
| 10,327,743 | B2 | 6/2019 | St. Goar et al. |
| 10,413,402 | B2 | 9/2019 | Squara |
| 10,420,565 | B2 | 9/2019 | Garcia et al. |
| 10,524,913 | B2 | 1/2020 | Delgado et al. |
| 10,779,829 | B2 | 9/2020 | Wei |
| 10,779,837 | B2 | 9/2020 | Lee et al. |
| 10,799,360 | B2 | 10/2020 | Kapadia |
| 10,842,626 | B2 | 11/2020 | de Canniere |
| 10,856,858 | B2 | 12/2020 | Thambar et al. |
| 10,888,424 | B2 | 1/2021 | Kuetting et al. |
| 10,945,718 | B2 | 3/2021 | Hiorth et al. |
| 10,966,823 | B2 | 4/2021 | Suri et al. |
| 10,980,632 | B2 | 4/2021 | Burriesci et al. |
| 11,000,372 | B2 | 5/2021 | Khairkhahan et al. |
| 11,007,060 | B2 | 5/2021 | He et al. |
| 11,020,221 | B2 | 6/2021 | Arcaro et al. |
| 11,026,785 | B2 | 6/2021 | Barash et al. |
| 11,045,311 | B2 | 6/2021 | Vaturi et al. |
| 11,058,535 | B2 | 7/2021 | Noe et al. |
| 11,090,158 | B2 | 8/2021 | Noe et al. |
| 2002/0077696 | A1 | 6/2002 | Zadno Azizi et al. |
| 2002/0095209 | A1 | 7/2002 | Zadno Azizi et al. |
| 2004/0260317 | A1 | 12/2004 | Bloom et al. |
| 2005/0070999 | A1 | 3/2005 | Spence |
| 2006/0178700 | A1 | 8/2006 | Quinn |
| 2006/0241745 | A1 | 10/2006 | Solem |
| 2007/0185571 | A1 | 8/2007 | Kapadia et al. |
| 2007/0203391 | A1 | 8/2007 | Bloom et al. |
| 2007/0282429 | A1 | 12/2007 | Hauser et al. |
| 2007/0293943 | A1 | 12/2007 | Quinn |
| 2008/0033541 | A1 | 2/2008 | Gelbart et al. |
| 2009/0222081 | A1 | 9/2009 | Linder et al. |
| 2011/0022164 | A1 | 1/2011 | Quinn et al. |
| 2011/0054598 | A1 | 3/2011 | Johnson |
| 2011/0077733 | A1 | 3/2011 | Solem |
| 2013/0238089 | A1 | 9/2013 | Lichtenstein et al. |
| 2014/0031928 | A1 | 1/2014 | Murphy et al. |
| 2014/0067048 | A1 | 3/2014 | Chau et al. |
| 2014/0114390 | A1 | 4/2014 | Tobis et al. |
| 2014/0163652 | A1 | 6/2014 | Witzel et al. |
| 2015/0100116 | A1 | 4/2015 | Mohl et al. |
| 2015/0173896 | A1 | 6/2015 | Richter et al. |
| 2015/0257885 | A1 | 9/2015 | McGuckin |
| 2015/0327971 | A1 | 11/2015 | Mujwid et al. |
| 2016/0030169 | A1 | 2/2016 | Shahriari |
| 2016/0089238 | A1 | 3/2016 | Centola et al. |
| 2016/0113766 | A1 | 4/2016 | Ganesan et al. |
| 2016/0166382 | A1 | 6/2016 | Nguyen |
| 2016/0199181 | A1 | 7/2016 | Kramer |
| 2016/0331523 | A1 | 11/2016 | Chau et al. |
| 2016/0367367 | A1 | 12/2016 | Maisano et al. |
| 2017/0056176 | A1 | 3/2017 | Rowe et al. |
| 2017/0079797 | A1 | 3/2017 | Maisano et al. |
| 2017/0112618 | A1 | 4/2017 | Li et al. |
| 2017/0239041 | A1 | 8/2017 | Quinn |
| 2017/0258589 | A1 | 9/2017 | Pham et al. |
| 2018/0036119 | A1 | 2/2018 | Wei et al. |
| 2018/0078361 | A1 | 3/2018 | Naor et al. |
| 2018/0168803 | A1 | 6/2018 | Pesce |
| 2018/0207336 | A1 | 7/2018 | Solem |
| 2018/0311037 | A1 | 11/2018 | Morriss et al. |
| 2019/0000618 | A1 | 1/2019 | Schweich et al. |
| 2019/0060072 | A1 | 2/2019 | Zeng |
| 2019/0069997 | A1 | 3/2019 | Ratz et al. |
| 2019/0083262 | A1 | 3/2019 | Hariton et al. |
| 2019/0201190 | A1 | 7/2019 | Dakin et al. |
| 2019/0343629 | A1 | 11/2019 | Solem |
| 2020/0000592 | A1 | 1/2020 | Lee et al. |
| 2020/0060818 | A1 | 2/2020 | Geist et al. |
| 2020/0069419 | A1 | 3/2020 | Lee et al. |
| 2020/0138570 | A1 | 5/2020 | Biadillah et al. |
| 2020/0205966 | A1 | 7/2020 | Khairkhahan et al. |
| 2020/0323616 | A1 | 10/2020 | Lashinski et al. |
| 2020/0337843 | A1 | 10/2020 | Khairkhahan et al. |
| 2020/0352707 | A1 | 11/2020 | Gifford |
| 2021/0022851 | A1 | 1/2021 | Pesce et al. |
| 2021/0022860 | A1 | 1/2021 | Lally et al. |
| 2021/0022864 | A1 | 1/2021 | Machold et al. |
| 2021/0030534 | A1 | 2/2021 | Siegel et al. |
| 2021/0038377 | A1 | 2/2021 | Pesce et al. |
| 2021/0038378 | A1 | 2/2021 | Sutherland et al. |
| 2021/0068950 | A1 | 3/2021 | Quill et al. |
| 2021/0085451 | A1 | 3/2021 | Kim |
| 2021/0128298 | A1 | 5/2021 | Rengarajan et al. |

FOREIGN PATENT DOCUMENTS

| | | |
|---|---|---|
| CN | 105188599 A | 12/2015 |
| WO | WO2005/027797 A1 | 3/2005 |
| WO | WO2008/141325 A1 | 11/2008 |
| WO | WO2013/173587 A1 | 11/2013 |
| WO | WO2016/180529 A1 | 11/2016 |
| WO | WO2018/042439 A1 | 3/2018 |
| WO | WO2018/145055 A1 | 8/2018 |

OTHER PUBLICATIONS

Pesce et al.; U.S. Appl. No. 17/649,329 entitled "Delivery system for heart valve support device," filed Jan. 28, 2022.

100

100

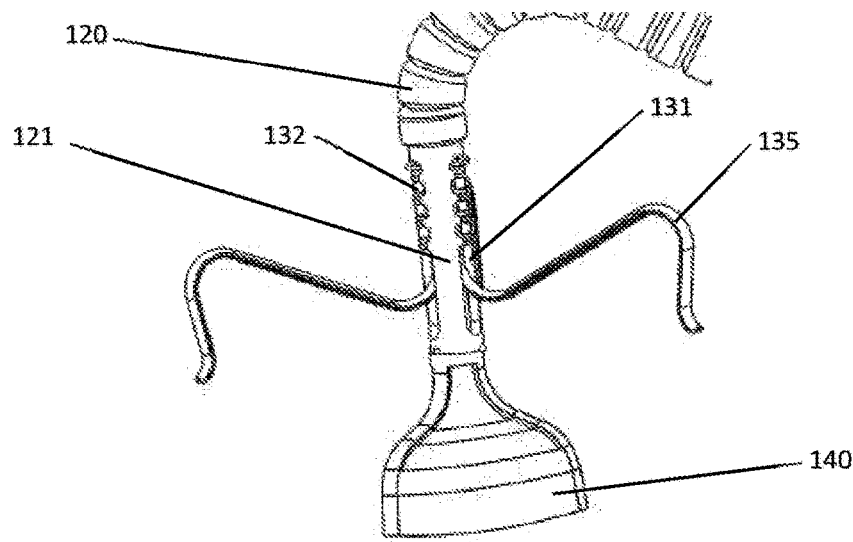
FIG. 3A
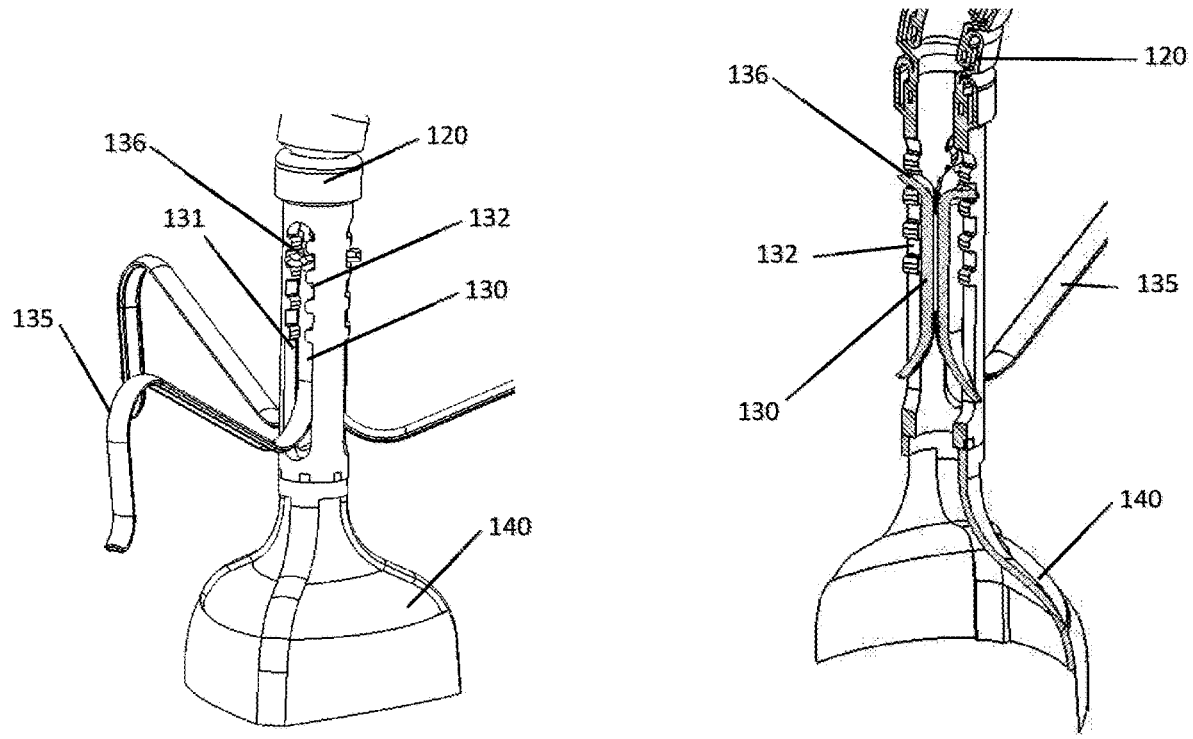
FIG. 3B
FIG. 3C

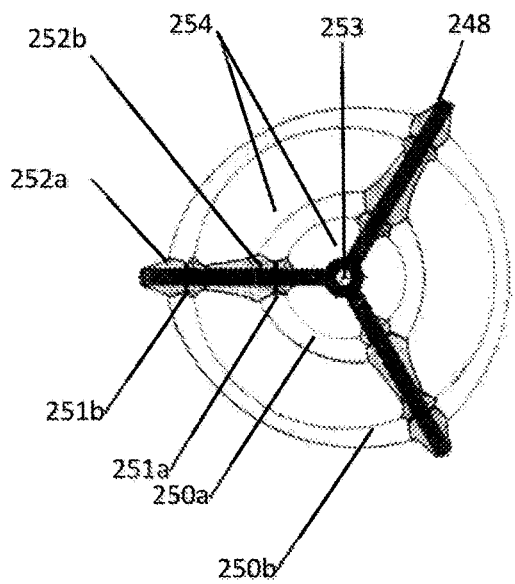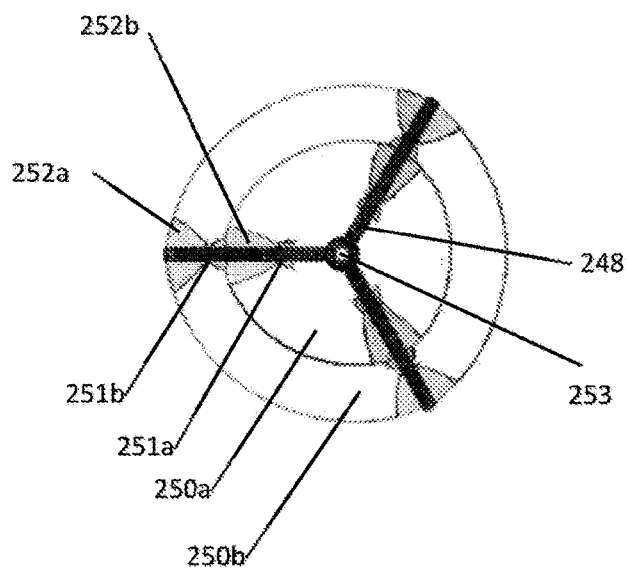
FIG. 8A  FIG. 8B
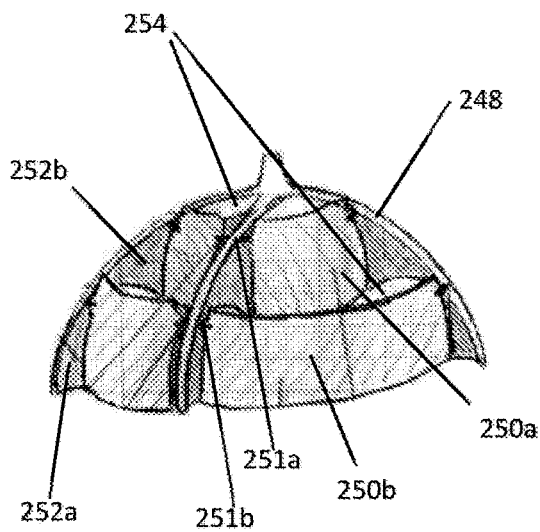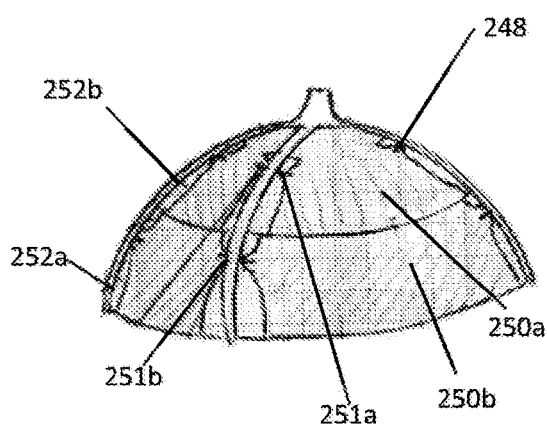
FIG. 8C  FIG. 8D

300

300

300

300

400

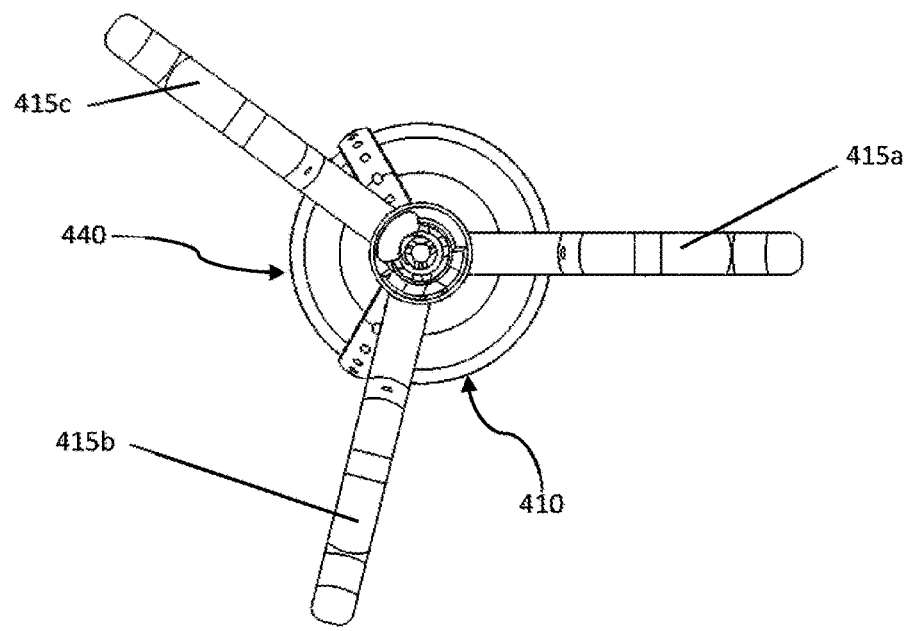
FIG. 32E
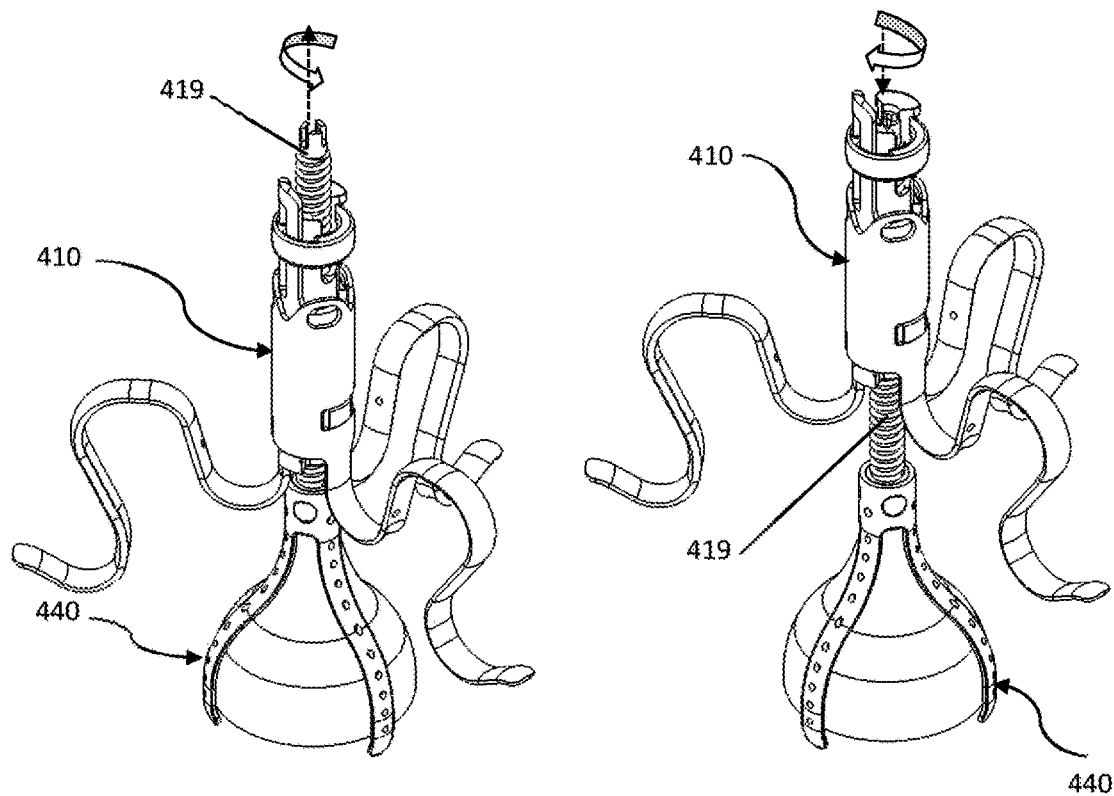
FIG. 33A
FIG. 33B

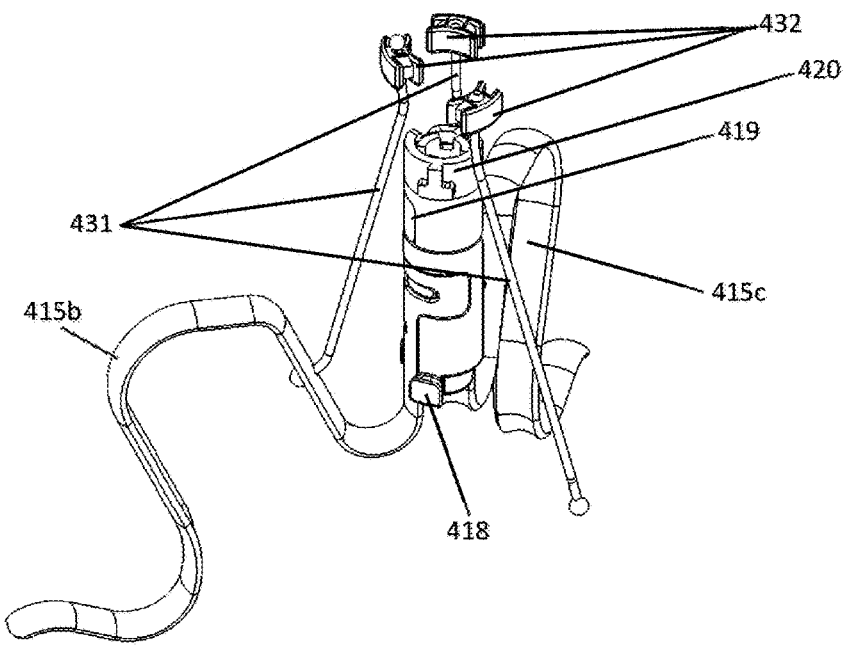
FIG. 38
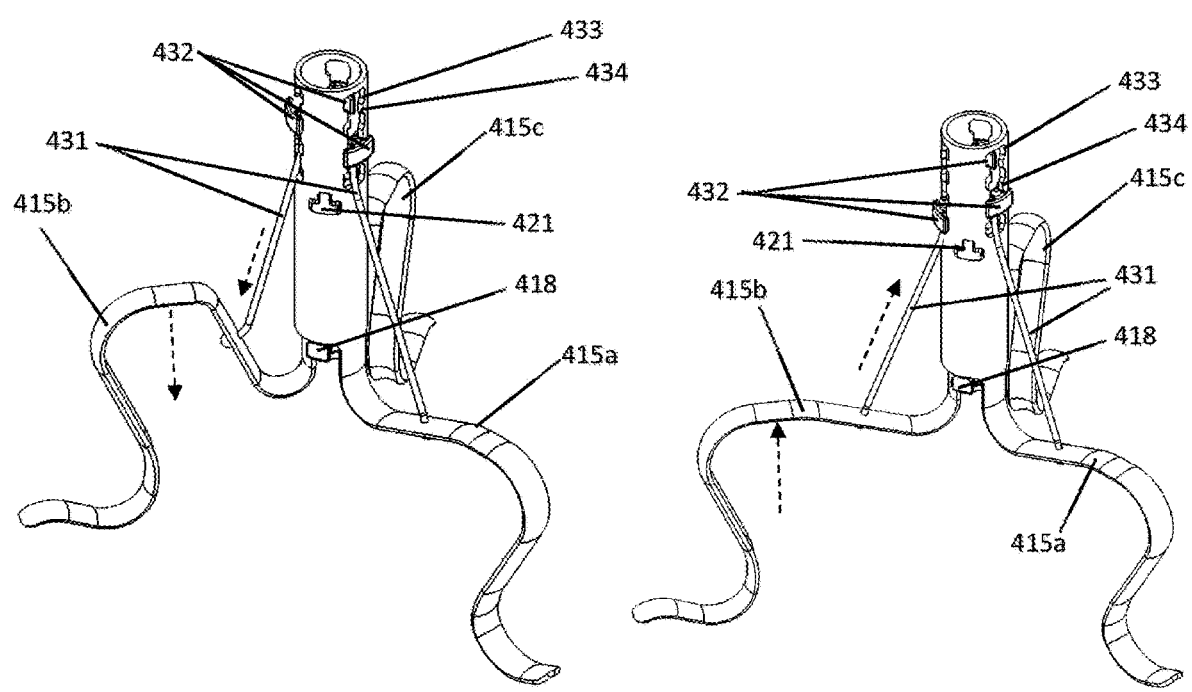
FIG. 39A
FIG. 39B

HEART VALVE SUPPORT DEVICE AND METHODS FOR MAKING AND USING THE SAME

CROSS REFERENCE TO RELATED APPLICATIONS

This application is a continuation of U.S. patent application Ser. No. 15/850,255, filed on Dec. 21, 2017, titled "HEART VALVE SUPPORT DEVICE AND METHODS FOR MAKING AND USING THE SAME," which claims priority to U.S. Provisional Patent Application No. 62/437,523, filed on Dec. 21, 2016. Priority to the provisional patent application is expressly claimed, and the disclosure of the provisional application is hereby incorporated herein by reference in their entireties and for all purposes.

CROSS-REFERENCE TO RELATED NONPROVISIONAL APPLICATIONS

The disclosure of the following PCT patent application is hereby incorporated herein by reference in its entirety and for all purposes: "HEART VALVE SUPPORT DEVICE AND METHODS FOR MAKING AND USING THE SAME," PCT International Patent Application No. PCT/US2015/034613, filed on Dec. 21, 2017.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The disclosed embodiments relate generally to medical device technology and more particularly, but not exclusively, to tricuspid valve support devices and methods for making and using the same.

BACKGROUND

A tricuspid valve (TV) is an atrioventricular valve located in the right side of the human heart, between the right atrium (RA) and the right ventricle (RV). Anatomy of the TV is constituted of three asymmetrical leaflets, septal, anterior, and posterior, supported by a complex sub-valvular apparatus constituted by the chordae tendineae and the papillary muscles. The TV is also in proximity of the tendon of Todaro, where the heart's delicate atrioventricular node is located.

Regurgitant flow occurs during the systolic phases of the cardiac cycle when the tricuspid valve becomes incompetent. The incompetence is mainly caused by the pathology-induced progressive enlargement of the valve's annulus, which prevents the leaflets from reaching full coaptation during systole (or during the systole phase of the cardiac cycle). The lack of leaflets coaptation causes the development of a regurgitant orifice within the valve through which blood can reenter the right atrium instead of exiting the right ventricle via the pulmonary valve. This condition induces a cardiac overload with subsequent enlargement of the right ventricle and the right atrium, reduction of the right ventricular stroke volume, and increase in systemic vein congestion and other symptoms of congestive heart failure. Tricuspid valve regurgitation can be isolated from or associated to other valvulopathies, and leads to congestive heart failure, with reduced functional cardiovascular capacity and ultimately increased risks of mortality.

Surgical repair or replacement are the most commonly used techniques for treating this pathology, but the clinical results (e.g. mortality and recurrence) are suboptimal. Also, due to the common presence of several comorbidities in most patients affected by tricuspid regurgitation, the majority is ineligible for surgical repair or replacement because of the high risk correlated with those procedures.

Transcatheter therapy doesn't require open-heart surgery and could be a viable safer alternative. The unique anatomical feature of the tricuspid valve is the main challenge for developing a safe and effective implant. The anchoring possibly requires burdening of the adjacent cardiac structure (e.g. superior or inferior vena cava, the atrioventricular node, the coronary sinus, the right coronary artery, the ventricular myocardium). Also, the low pressure and output of the hemodynamic flow in the right side of the heart increases the risks of inducing atrioventricular pressure gradient and thrombogenesis.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3A is a schematic of the distal end of an exemplary embodiment of a vena cava-anchored device in a deployed conformation.

FIG. 3B is a schematic of a height adjustment mechanism for atrial arms of an exemplary embodiment of a vena cava-anchored device.

FIG. 3C is a cross-section detailed view of a height adjustment mechanism for atrial arms of an exemplary embodiment of a vena cava-anchored device.

FIG. 8A is a top-view schematic of one embodiment described herein of tricuspid valve flow optimizer having two overlapping semi-rigid flaps in a diastolic conformation.

FIG. 8B is a top-view schematic of one embodiment described herein of tricuspid valve flow optimizer having two overlapping semi-rigid flaps in a systolic conformation.

FIG. 8C is an isometric schematic of one embodiment described herein of tricuspid valve flow optimizer having two overlapping semi-rigid flaps in a diastolic conformation.

FIG. 8D is an isometric schematic of one embodiment described herein of tricuspid valve flow optimizer having two overlapping semi-rigid flaps in a systolic conformation.

FIG. 32E is an atrial (top) view of an exemplary embodiment of a commissures-anchored device with the anchoring arm 415c radially displaced counterclockwise towards arm 415b starting from the position shown in FIG. 32E.

FIGS. 33A and 33B are schematics showing height and radial orientation adjustment functionality an exemplary embodiment of a flow optimizer.

FIG. 38 is a schematic of a commissures-anchored device in FIG. 35 with Arm 415a not displayed to allow visualization of the anchoring mechanism internal components.

FIGS. 39A and 39B are schematics showing a commissures-anchored device in FIG. 35 with arm 415b in different expanded conformations.

Figure 1A:
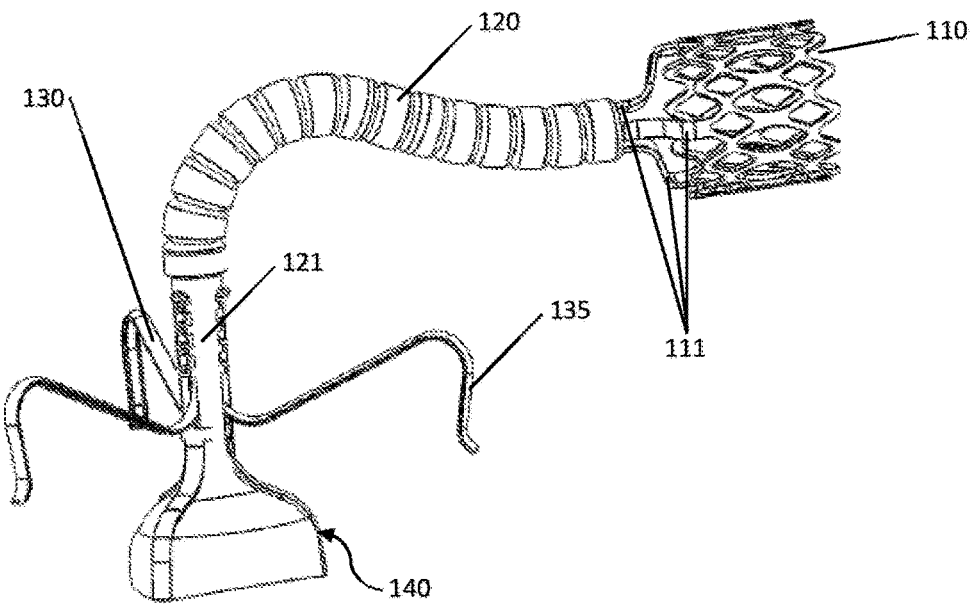
FIG. 1A is a schematic of an exemplary embodiment of a vena cava-anchored device in a deployed conformation.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION

The disclosed embodiments relate to catheter-delivered intracardiac implants for supporting and improving the function of the tricuspid valve.

This disclosure captures a novel device with one or more features to address such an anatomically and hemodynamically challenging scenario. During the diastolic phase of the cardiac cycle, a flow optimizer is devised to minimize its cross-sectional area and allows hemodynamic flow around and also through the implant, thus minimizing the potential risk of inducing atrioventricular pressure gradient and thrombogenesis. During the systolic phase, the flow optimizer seals or minimizes the regurgitant orifice and reinstates the efficacy of the tricuspid valve. The device's anchoring system doesn't require traumatic interaction with the tricuspid valve, right atrium and right ventricle, and implantation can be achieved with minimal procedural steps. Furthermore, anchoring mechanism of the device permits intra-procedural adjustments, under standard imaging techniques (e.g. fluoroscopy, echocardiography), of positioning of the flow optimizer within the native tricuspid valve to allow real-time optimization of the hemodynamic flow across the tricuspid valve. The disclosure is devised to increase the efficacy, safety, and procedural success of transcatheter therapy of tricuspid valve regurgitation.

The present disclosure provides tricuspid valve support devices that can be used to reduce or prevent tricuspid regurgitation (TR). The devices are capable of adopting a crimped conformation, so that they can be deployed using a standard intravascular catheter, and a deployed conformation within the body. Generally, the devices have a tricuspid valve flow optimizer that is placed within the lumen of the tricuspid valve. The flow optimizer permits diastolic hemodynamic flow from the right atrium into the right ventricle and, during systole, reduces or prevents blood regurgitation from the right ventricle into the right atrium through the regurgitation orifice present in the tricuspid valve of subjects affected by TR. The flow optimizer is directly connected to an anchoring structure that engages the tricuspid valve annulus at the commissure of the native leaflets and/or the supra-annular walls of the right atrium. In alternative configurations, the flow optimizer is attached to an anchoring element directly or through an articulating link. The articulating link can be configured to adopt and hold a three-dimensional configuration in order to maintain a proper shape and orientation from the anchoring device and within the tricuspid valve lumen. The anchoring element can be an intravascular stent configured to anchor the device by a frictional contact within the SVC or IVC, thereby providing support to the flow optimizer from the atrial side and further comprises an atrial support or anchoring structure. Alternatively, the anchoring element is frictionally engaged with the inner wall of the right ventricle, preferably at the ventricle apex. Optionally, this latter configuration further comprises an atrial anchoring structure.

Although shown and described with reference to a tricuspid valve for purposes of illustration only, the device, the flow optimizer and/or the anchoring mechanism can be applied to any valve of the heart.

In some embodiments, the device can be at least partially oriented such that two opposite end regions of the device are close to and away from the heart, respectively. In those embodiments, "distal" can be a relative term that can refer to the direction or side towards the heart and, more specifically, toward the ventricle apex of the heart. For example, the flow optimizer 140 in FIG. 1A is located at the distal end of the vena cava-anchored device, as described in more detail below. In those embodiments, "proximal" can be a relative term that can refer to the direction or side away from the heart. For example, anchoring stent 110 in FIG. 1A is located at the proximal end of the vena cava-anchored device, as described in more detail below.

The disclosure provides an implantable tricuspid valve support device that can be delivered and implanted using a catheter. The device provides a flow optimizer that is placed within the tricuspid valve to support and improve the hemodynamic function in patients affected by tricuspid regurgitation (TR). The device seals the coaptation gap between the native leaflets during the systolic phase of the cardiac cycle and allows blood flow from the right atrium to the right ventricle during the diastolic phase of the cardiac cycle. In some embodiments, the disclosure provides an anchored device. Anchoring can be achieved from the atrial side such as within the superior vena cava (SVC) or the inferior vena cava (IVC), or anchoring can be achieved by supporting the device from within the right ventricle. In some embodiments, the device is anchored only within the right atrium. In other embodiments, the device is anchored within the right atrium, at the commissures of the tricuspid valve annulus, and/or at the supra-annular region of the right atrium.

Vena Cava-Anchored Tricuspid Valve Support Device 100

Figure 1B:
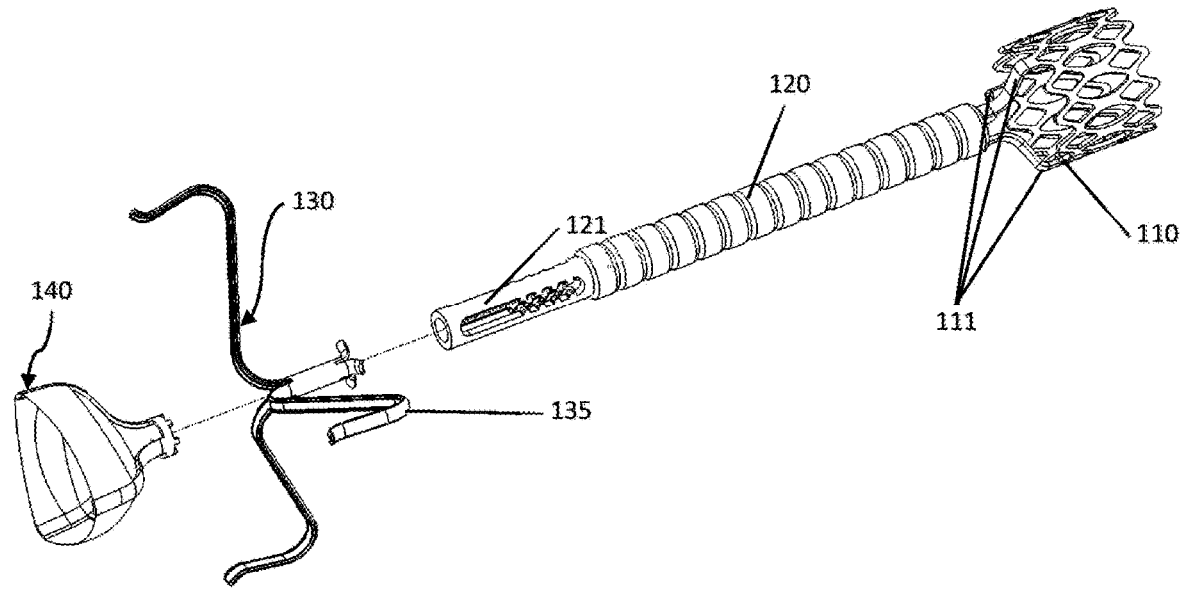
FIG. 1B is an exploded view of an exemplary embodiment of a vena cava-anchored device in a deployed conformation.
Figure 2A:
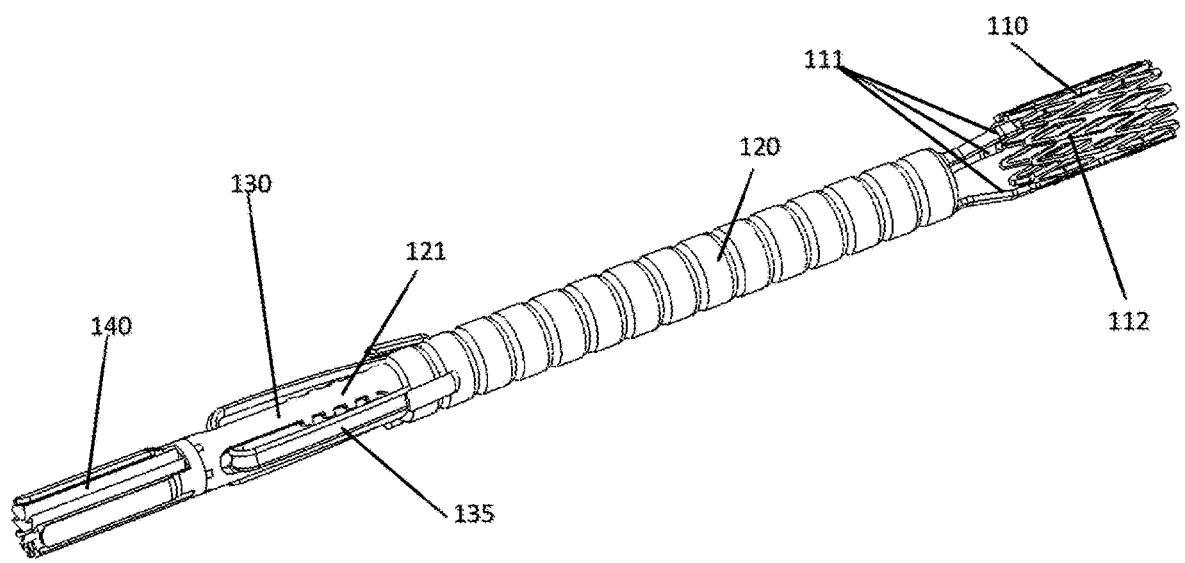
FIG. 2A is a schematic of an exemplary embodiment of a vena cava-anchored device in a crimped conformation.
Figure 2B:
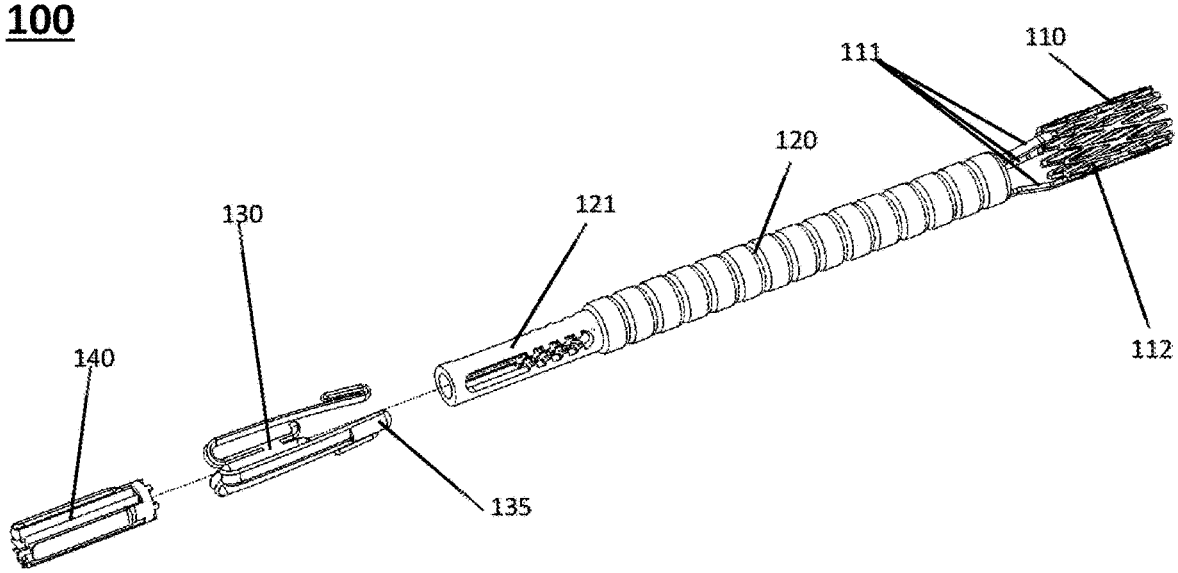
FIG. 2B is an exploded view of an exemplary embodiment of a vena cava-anchored device in a crimped conformation.

FIG. 1A illustrates a tricuspid valve support device 100, in a deployed conformation, configured to be anchored in the vena cava. The vena cava can include superior vena cava (SVC) and/or inferior vena cava (IVC). FIG. 1A shows the device 100 as including an anchoring stent 110 connected to an atrial anchor 130 via an articulating Link 120. The atrial anchor 130 is attached to a tricuspid valve flow optimizer 140 and comprises one or more (e.g., one, two, three, four, or more) atrial support arms 135. FIG. 1B illustrates an exploded view of these elements in the deployed conformation. FIG. 2A illustrates the tricuspid valve support device 100 in a crimped conformation as the tricuspid valve support device 100 can be loaded into an intravascular delivery catheter (not shown). FIG. 2B illustrates an exploded view of the tricuspid valve support device 100 in a crimped conformation. Each of the device elements and the method for deployment is described in more detail below.

Anchoring Stent 110

The anchoring stent 110 is sized and adapted to adopt a crimped conformation, when loaded and housed within an intravascular catheter, and a deployed conformation. The anchoring stent 110 can be self-expanding and/or balloon-deployed. The anchoring stent 110 can be appropriately sized for the desired anchoring vessel (i.e., the SVC or IVC) and is configured and constructed in accordance with standard techniques and materials used for intravascular stents. For example, the anchoring stent 110 can be formed from stainless steel, a memory shape metal such as Nitinol® (NiTi), or any suitable biocompatible polymer. The anchoring stent 110 serves to anchor the device within the body by a frictional contact with the inner wall of the blood vessel while maintaining vessel patency. The anchoring stent 110 can have a generally cylindrical stent body 112. The stent body 112 can be attached at a distal end region thereof to the articulating link 120. In one configuration, the stent body 112 can be attached at the distal end region thereof to a proximal end region of the articulating link 120 by one or more (e.g., one, two, three, four, or more) Stent Arms 111.

Articulating Link 120

The articulating link 120 is adapted to connect the anchoring stent 110 to the atrial anchor 130 without significantly impeding blood flow. For example, articulating link 120 can be configured to reside toward the center and/or midline of the vessel, when deployed. The articulating link 120 can be solid or hollow. Articulating link 120 further comprises a Receiver 121 at its distal end that is adapted to receive and secure the atrial anchor 130. The Receiver 121 can comprise a first mating pair member adapted to mate with a second mating pair member located on the atrial anchor 130. The receiver 121 can be articulating or non-articulating. For embodiments in which the receiver 121 is non-articulating, it is configured to reside entirely within the atrium so that the lack of articulation does not interfere with the proper placement and orientation of the atrial anchor 130 and/or the flow optimizer 140.

Figure 17A:
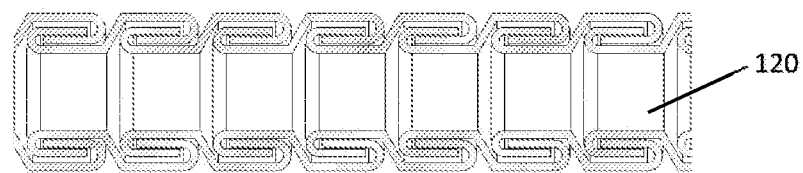
FIGS. 17A and 17B are schematics of exemplary embodiments of interlocking links that can be used with the articulating link in the devices described herein.
Figure 17B:
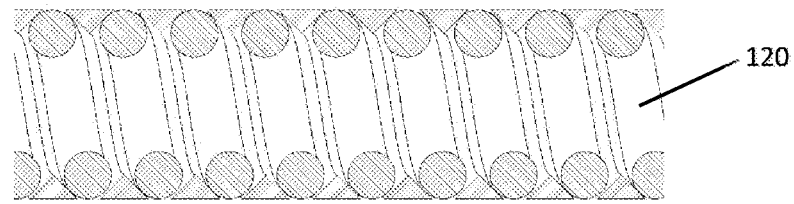

The articulating link 120 is configured to deform and maintain any three-dimensional curvature induced by the catheter delivery system. A variety of gooseneck, interlocking coils, and interlocking links can be used in accordance with the principles set forth herein. FIGS. 17A and 17B illustrate two exemplary types of interlocking links that can be used.

Atrial Anchor 130

The atrial anchor 130 comprises a second mating pair member adapted to mate with the first mating pair member located on receiver 121. The atrial anchor 130 can include one or more (e.g., one, two, three, four, or more) radially-deploying atrial support arms 135. The atrial anchor 130 is adapted to support the flow optimizer 140, on the distal end region of the atrial anchor 130 and within the tricuspid valve (e.g., through the receiver 121). Preferably, the arms 135 are self-deploying from the crimped conformation to the deployed conformation once released from the delivery catheter. The arms 135 can be formed from any suitable material, including memory shape materials such as NiTi. Optionally, the arms 135 further comprise a friction enhancing layer on a body-facing surface of the arms 135, in order to enhance adhesion with the atrial wall. Exemplary friction enhancing layer can be made of polymer including, for example, fabric hook and loop fasteners (for example, Velcro® available from Velcro company in United Kingdom) and microbarbs.

Additionally and/or alternatively, the atrial anchor 130 further comprises a height adjustment mechanism adapted to adjust the vertical positioning of the arms 135 relative to the flow optimizer 140. FIG. 3A illustrates an exemplary height adjustment mechanism defining a channel 131 having a series of notches 132 into which an arm 135 is fitted. FIG. 3B provides a close-up view of the vertical positioning system, and FIG. 3C provides a cross-sectional view of the interior elements. The distal end region of each arm 135 terminates in a tab 136. Each arm 135 is slidably engaged with a channel 131 in the receiver 121 such that arm 135 can be translocated in the proximal or distal axial direction. Channel 131 defines a series of horizontal notches 132 sized to accept tab 136.

In one embodiment, the arms 135 can be positioned in the deployed conformation, prior to loading the device 100 into the deliver catheter. The selection of the height positioning can be determined using imaging and/or other data obtained from the patient.

Additionally and/or alternatively, the arms 135 can be positioned proximally or distally relative to the flow optimizer 140 after deployment of the device 100 within the atrium. For example, the arms 135 can be translocated relative to the flow optimizer 140 using an internal operator-controlled wire that is affixed to the distal end of the arms 135 and adapted to pull the distal end regions of the arms 135 inward towards the central axis of lumen of the device 100, thereby releasing the tabs 136 from the notches 132. The arms 135 can be translocated in the axial direction and the spring/memory shape property of the distal ends returns the tabs 136 into the notches 132 when tension from the catheter is released.

Additionally and/or alternatively, the tabs 136 are reversibly engaged with a wire or tube internal to the catheter lumen in a manner that maintains the tabs 136 disengaged from the notches 132. After deployment of the device, the operator may translocate the arms 135 using that internal wire or tube until the arms 135 are properly positioned within the atrium (e.g., frictionally engaged with the atrial wall), and them disengage the tabs 136 from the internal wire or tube such that the tabs 136 become engaged with the notches 132.

Tricuspid Valve Flow Optimizer 140

Figure 4:
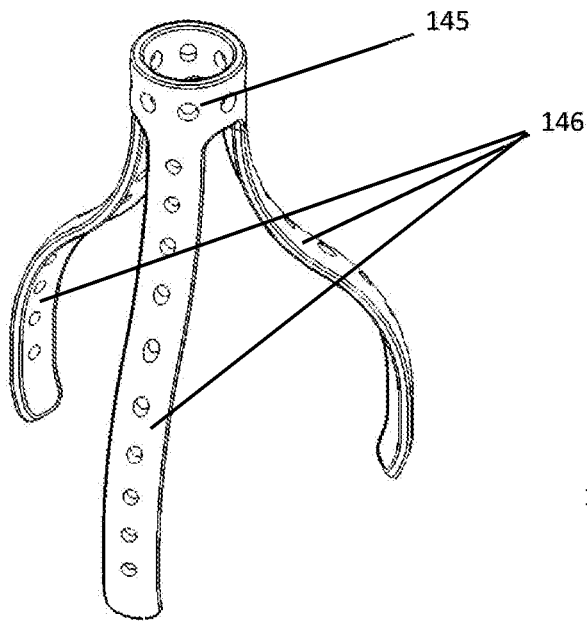
FIG. 4 is an isometric view of an exemplary embodiment of the frame of the tricuspid valve flow optimizer that can be used with the devices described herein.

FIG. 4 shows the tricuspid valve flow optimizer 140 as being in conical in shape. However, the tricuspid valve flow optimizer 140 can be formed in any desirable shape, preferably to match the tricuspid valve anatomy to ensure the atraumatic coaptation during systole of the native tricuspid valve leaflets on the flow optimizer. Specifically, during the systolic phase of the cardiac cycle, the flow optimizer 140 is devised to coapt with the tricuspid valve leaflets and fill the regurgitation orifice in the tricuspid valve. During the diastolic phase of the cardiac cycle, the flow optimizer 140 permits hemodynamic flow from the right atrium into the right ventricle. Exemplary flow optimizer 140 can include a frame 145. An exemplary frame 145 can be formed from a memory-shape material. For example, the frame 145 can include a wire/ribbon frame made from a memory shape material, such as NiTi. The exemplary flow optimizer 140 can include a covering formed from one or more (e.g., two, three, four, five, or more) layers of the leaflets 150 (shown in FIG. 5A).

Figure 6E:
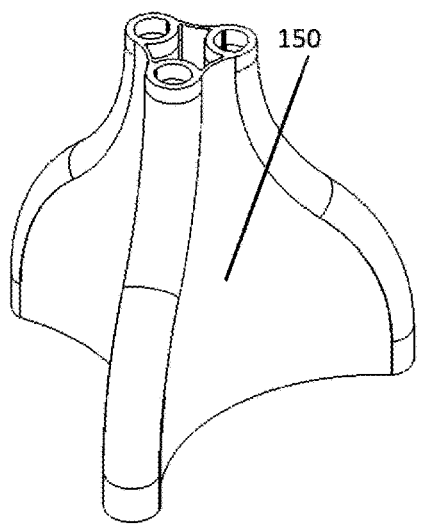
FIG. 6E is a view of an exemplary embodiment of a single-layer leaflets sub-assembly molded in diastolic conformation.
Figure 6F:
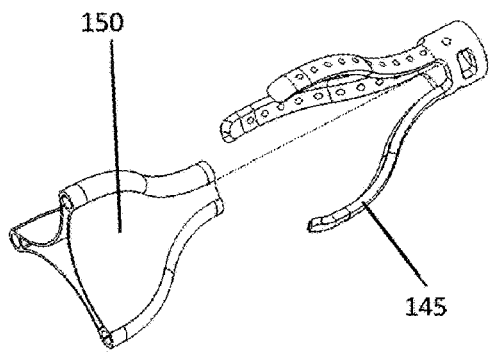
FIG. 6F is an exploded view of an exemplary embodiment of the flow optimizer 140 assembled with the frame 145 and a single-layer leaflets sub-assembly molded in diastolic conformation.
Figure 7A:
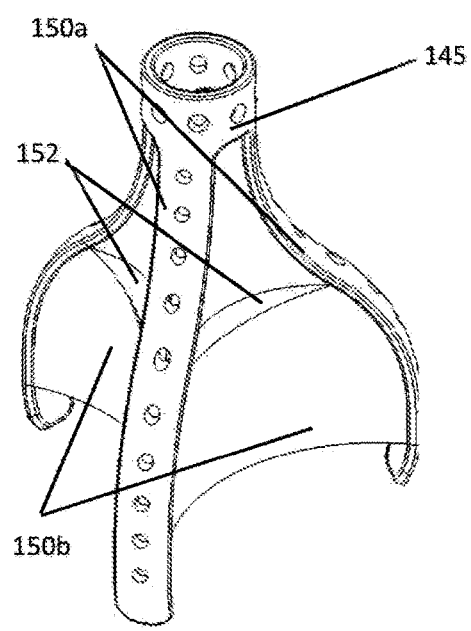
FIGS. 7A and 7C are schematics showing the conformation of an exemplary embodiment of a tricuspid valve flow optimizer having an overlapping leaflets configuration during the diastolic phase of the cardiac cycle.
Figure 7B:
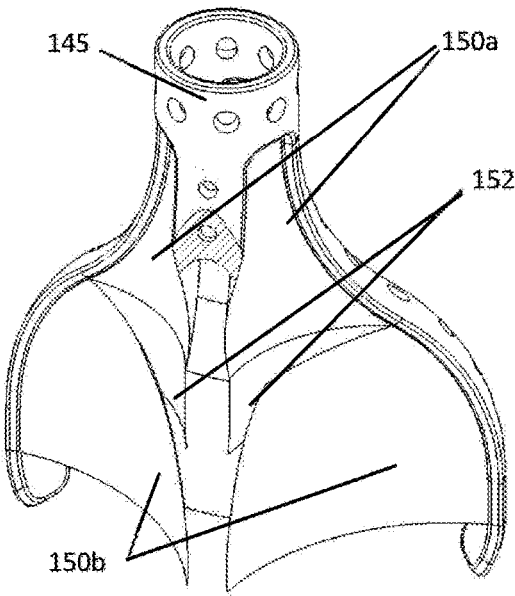
FIG. 7B is a cross-section view of the flow optimizer illustrated in FIG. 6A, showing a cut-away of the frame and leaflets layers.
Figure 7C:
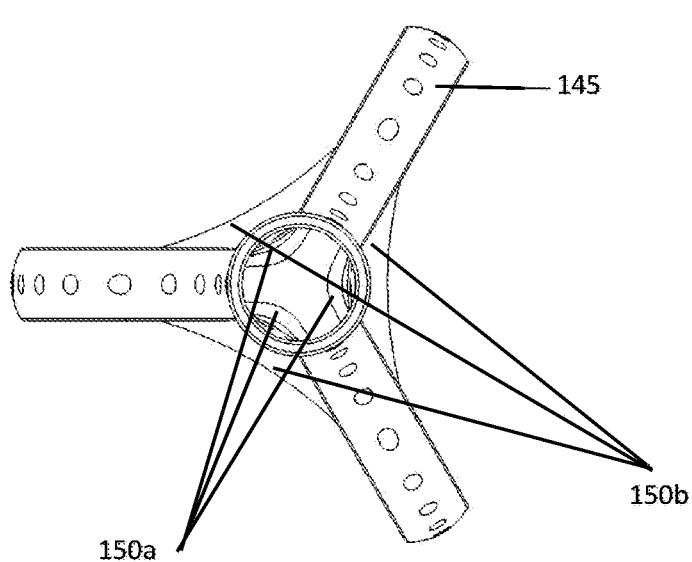
Figure 7D:
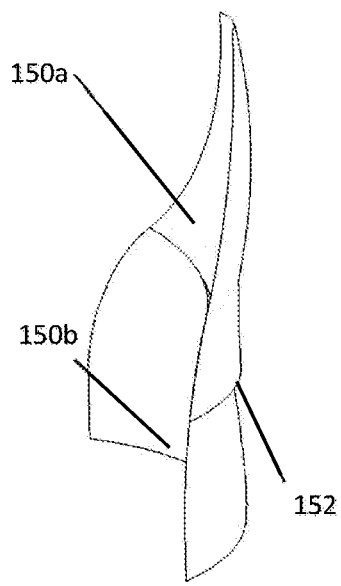
FIG. 7D is a view of the overlapping leaflets of the flow optimizer illustrated in FIGS. 7A-7C.
Figure 7E:
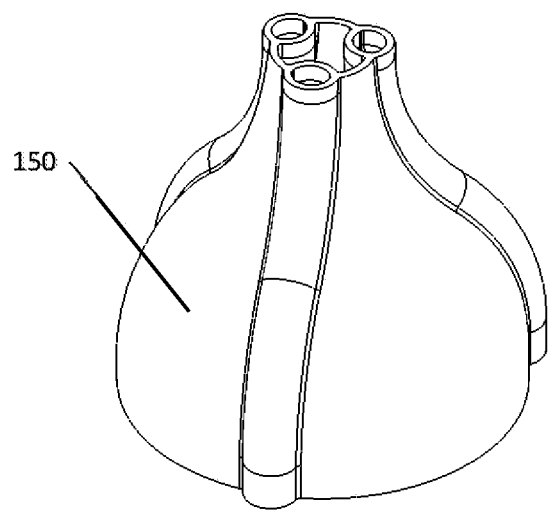
FIG. 7E is a view of an exemplary embodiment of a single-layer leaflets sub-assembly molded in systolic conformation.

As shown in FIG. 4, the flow optimizer frame can comprise two or more (e.g., two, three, four, five, or more) arms 146 that support the covering material and impart the desired three-dimensional shape to the leaflets 150. The leaflets 150 can be made of a material that is impermeable to blood cells and, preferably, impermeable to blood fluids (e.g., aqueous solutions). The leaflets 150 can be formed from any suitable biocompatible material including, for example, woven or nonwoven polymer fabrics or sheets, and/or biological tissue harvested from animals (e.g., bovine, porcine, and equine) or humans. Suitable biological tissue includes, for example, tissue obtained from the pericardial sac of the donor animal and/or human. The leaflets 150 are sutured or attached with other standard fastening methods (e.g. adhesives) on the arms 146 of the frame 145. Additionally and/or alternatively, the leaflets 150 can be molded in the desired three dimensional shape as a single sub-assembly mountable on the frame 145 as shown in FIGS. 6E-6F and FIG. 7E.

Figure 5A:
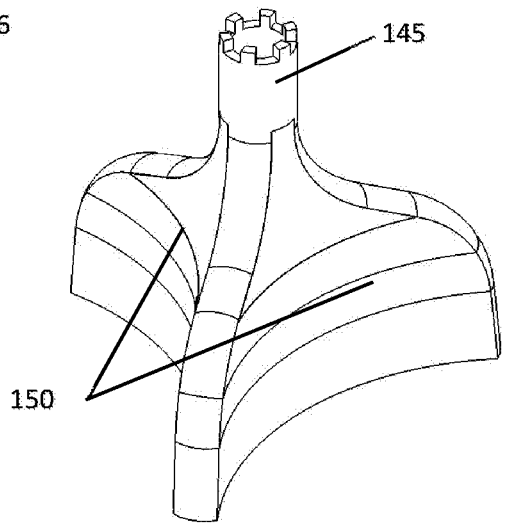
FIG. 5A is a schematic showing the conformation of an exemplary embodiment of a tricuspid valve flow optimizer having a single layer leaflets, during the diastolic phase of the cardiac cycle.

As shown in FIG. 5A, the tricuspid valve flow optimizer 140 can be configured to allow the leaflets 150 to collapse towards the center axis of frame 145 during diastole (or during a diastole phase of the cardiac cycle). The leaflets 150 of the tricuspid valve flow optimizer 140 are made from a pliable but impermeable material that forms a collapsible dome and/or other three-dimensional structures. During diastole, when blood flows from the right atrium into the right ventricle through the tricuspid valve under atrial contraction, the atrioventricular hemodynamic pressure gradient opens the tricuspid valve leaflets (not shown). The atrioventricular hemodynamic pressure gradient collapses the leaflets 150 of flow optimizer 140 towards the center axis of the frame 145, such that the three-dimensional volume and cross sectional area of the flow optimizer 140 can be reduced as shown in FIG. 5A, thereby allowing blood to flow unrestricted into the ventricle around the flow optimizer 140. The cross sectional area of the tricuspid valve flow optimizer 140 can include a size of the tricuspid valve flow optimizer 140 when the tricuspid valve flow optimizer 140 is viewed from the right atrium.

Figure 5B:
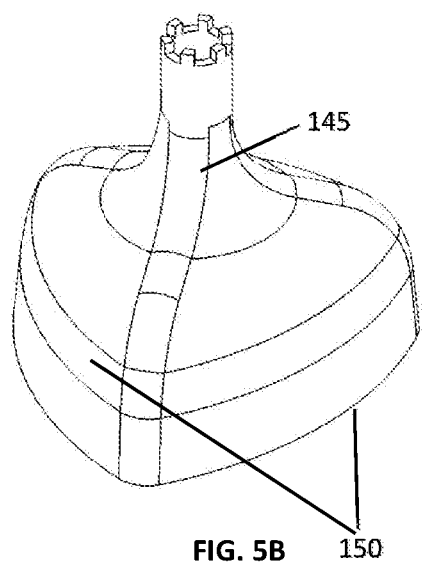
FIG. 5B is a schematic showing the conformation of an exemplary embodiment of a tricuspid valve flow optimizer having a single layer leaflets, during the systolic phase of the cardiac cycle.
Figure 5C:
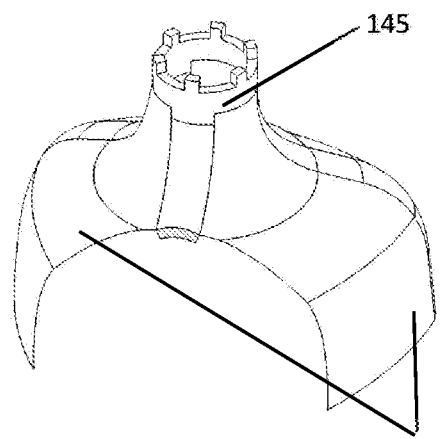
FIG. 5C is a cross-section view of the flow optimizer illustrated in FIG. 5B, showing a cut-away of the frame and leaflet layer.

As shown in FIG. 5B, the tricuspid valve flow optimizer 140 can be configured to inflate towards the arms 146 to fill the lumen of the regurgitation orifice (not shown) and thereby prevents regurgitation during systole. As shown in FIG. 5B, during systole (i.e., ventricular contraction), when the tricuspid valve leaflets coapt around the flow optimizer 140, the ventricular hemodynamic pressure inflates the leaflets 150 to their full three-dimensional volume which is sufficient to close the tricuspid valve regurgitant orifice and reduce or prevent blood flow into the right atrium.

Figure 6A:
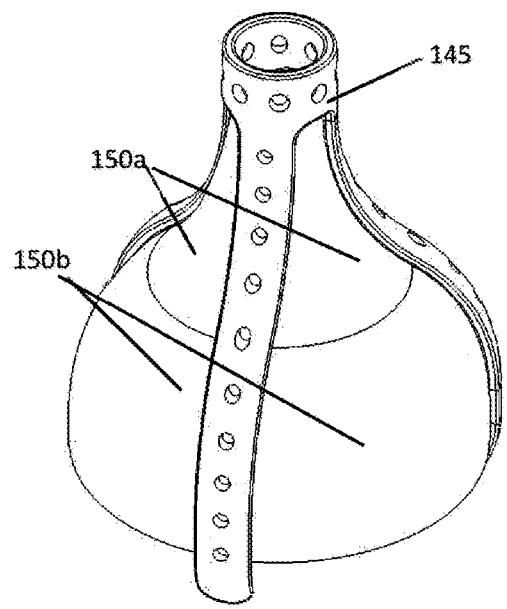
FIGS. 6A and 6C are schematics showing the conformation of an exemplary embodiment of a tricuspid valve flow optimizer having an overlapping (two) leaflets configuration during the systolic phase of the cardiac cycle.
Figure 6B:
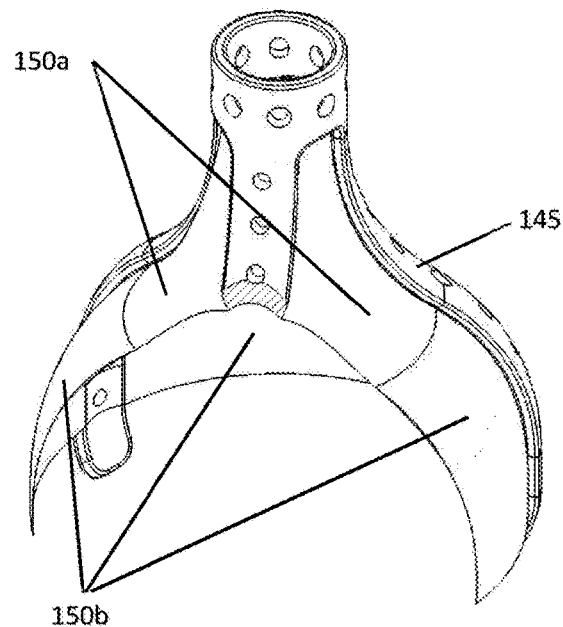
FIG. 6B is a cross-section view of the flow optimizer illustrated in FIG. 6A, showing a cut-away of the frame and leaflets layers to further illustrate the principles and construction of this element.
Figure 6C:
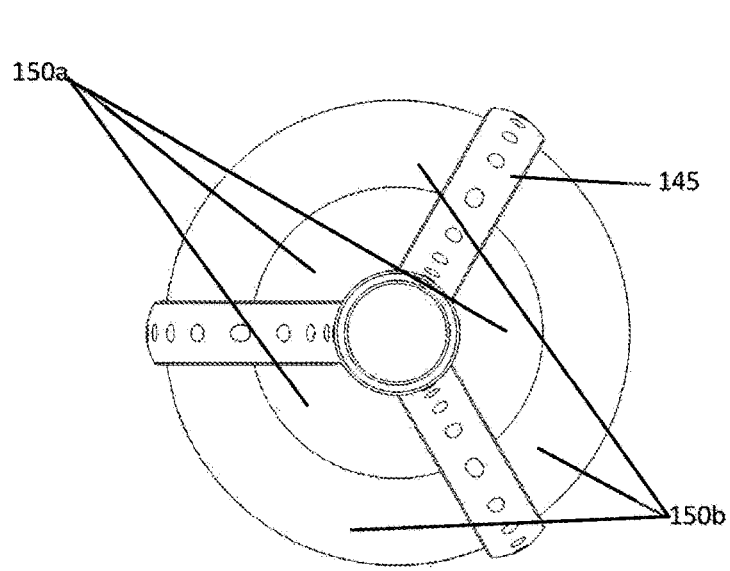
Figure 6D:
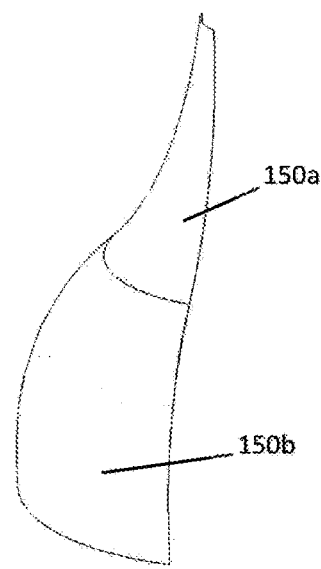
FIG. 6D is a view of the overlapping (two) leaflets of the flow optimizer illustrated in FIGS. 6A-6C.

Additionally and/or alternatively, as shown in FIG. 6A, the covering of flow optimizer 140 can be formed from an overlapping cascade of two or more (e.g., two, three, four, or more) circumferential leaflet layers of the leaflets 150 to achieve, during the diastolic phase, an efficient reduction of the three-dimensional volume, and to leave open gaps between the leaflet layers of the leaflets 150, allowing a blood flow path throughout the flow optimizer 140. The gaps further minimize the cross-section area of the flow optimizer 140 that can restrict the hemodynamic flow, thus reducing the potential of creating a pressure gradient across the native tricuspid valve. The gaps also improve blood washout within the flow optimizer, minimizing blood stagnation and thus risk of thrombogenesis. The circumferential leaflets are aligned such that the distal (bottom, or the ventricle-side) edge of the upper leaflet layer (closest to the atrium) 150a overlaps on the inside of the proximal (upper, or the atrium-side) edge of the lower leaflet layer (closest to the ventricle) 150b.

As shown in FIGS. 6A-6D, during systole, the ventricular pressure closes the leaflets of the tricuspid valve, making the leaflets of the tricuspid valve coapt around the flow optimizer 140, and expands the leaflets layers 150a, 150b to a full three-dimensional shape, pressing the leaflets layers 150a, 150b together to seal gaps 152 (shown in FIG. 7A), and preventing blood flowing into the ventricle to pass through and around the flow optimizer 140.

During diastole, depending upon the construction and choice of materials and shapes, the leaflets layers 150a, 150b of the flow optimizer 140 partially and/or completely collapse, allowing blood flow from the atrium into the ventricle around the flow optimizer 140 and also through the gaps 152 open between the leaflets layers 150a and 150b as shown in FIGS. 7A-7D. A similar pattern of overlapping three, four or more leaflet layers can be used for each leaflet 150.

In one embodiment shown in FIG. 8A and FIG. 8C, six flaps 250a, 250b, arranged over two levels, allow hemodynamic flow through gaps 254 of the flow optimizer 140 during the diastolic phase of the cardiac cycle. As shown in FIGS. 8B and 8D, the flaps 250a and 250b close the gaps 254 during the systolic phase of the cardiac cycle and thus prevent regurgitation through the native tricuspid valve. The flaps 250a, 250b are semi-rigid in order to retain a shape when opening or closing. Three flaps 250a are arranged on the upper layer of the frame 248, and three flaps 250b are arranged on the lower layer of the frame. The flaps 250a and 250b are connected to the frame 248 of flow optimizer 140 with connection strips 252a, 252b, which are patches of soft tissue or other pliable impermeable material preventing blood passage through the boundaries of flaps 250a and 250b. The patches are connected to the frame 248 with hinges 251a, 251b. FIG. 8A and FIG. 8C show flow optimizer 140 during the diastolic phase of the cardiac cycle, when the atrioventricular pressure gradient rotates the flaps 250a and 250b about hinges 251a and 251b in the direction of the hemodynamic flow. In this conformation, blood can pass through the open gaps 254 between the flaps 250a and 250b, providing a washing action to prevent risk of blood stagnation and thrombogenesis within the flow optimizer.

FIG. 8B shows the flow optimizer 140 during the systolic phase of the cardiac cycle, when the atrioventricular pressure gradient rotates the flaps 250a and 250b towards the atrium. In this conformation, the distal (closer to the ventricle) edges of the flaps 250b overlap with the proximal (closer to the atrium) edges of the flaps 250a, thus sealing gaps 254 and preventing blood passage through.

Deployment of Vena Cava-Supported Device 100

Device 100 can be anchored in the SVC and/or the IVC, depending upon which vessel is accessed. Deployment through the SVC is shown herein. The same principles and techniques can apply to the deployment of device 100 through the IVC.

Figure 9A:
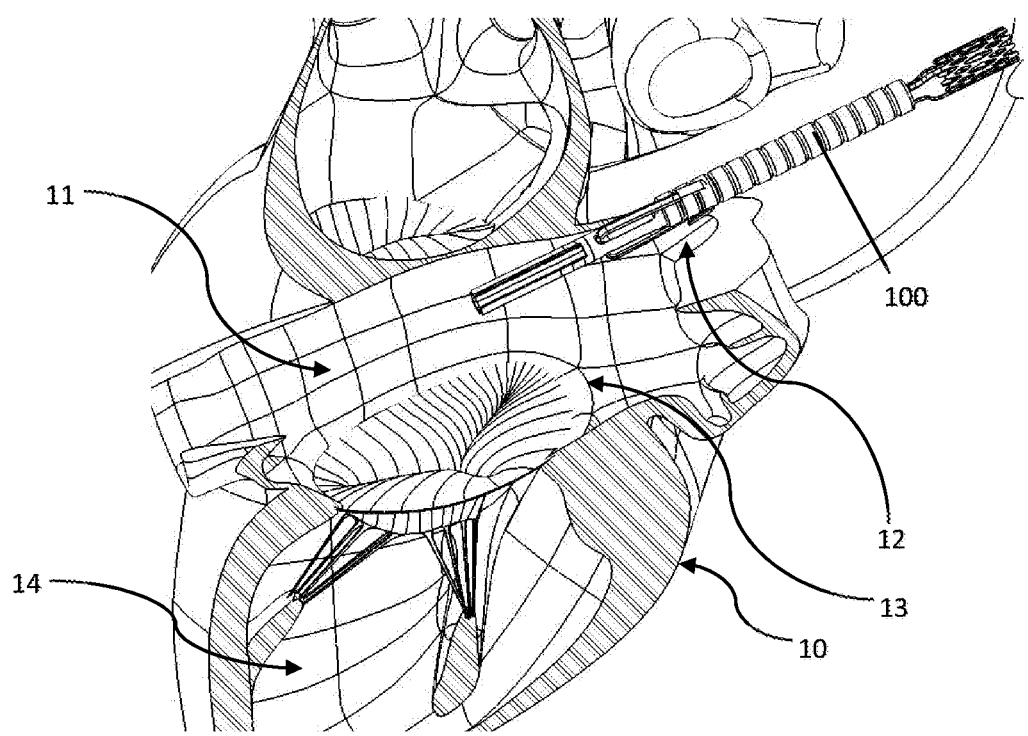
FIGS. 9A-9E illustrate the deployment sequence of an exemplary embodiment of a vena cava-anchored device.
Figure 9B:
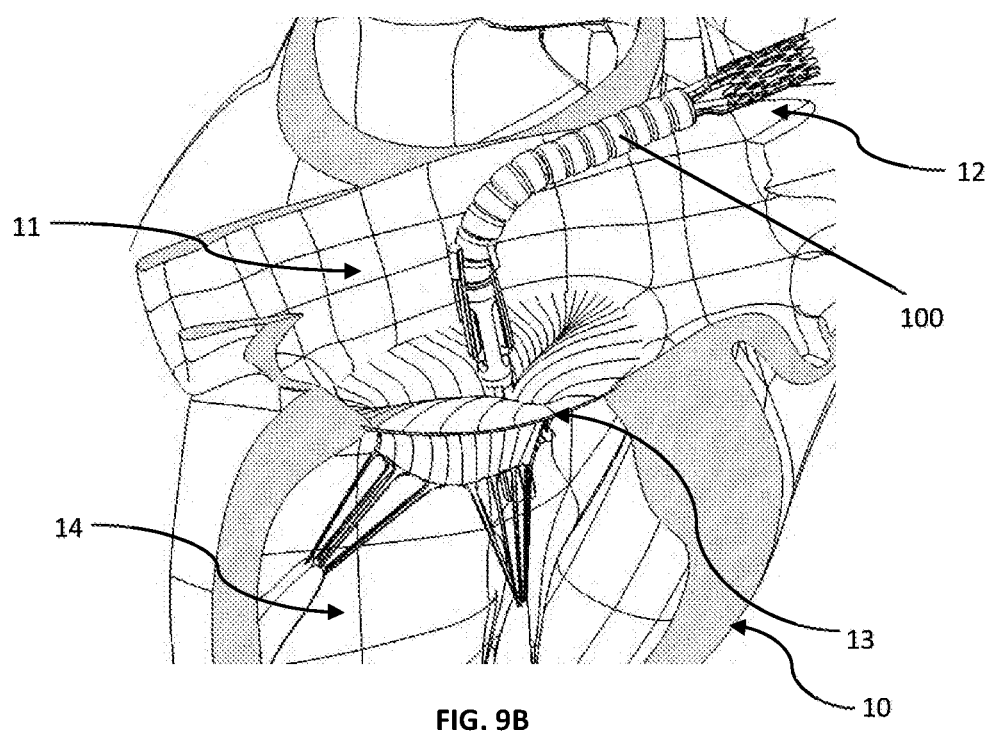
Figure 9C:
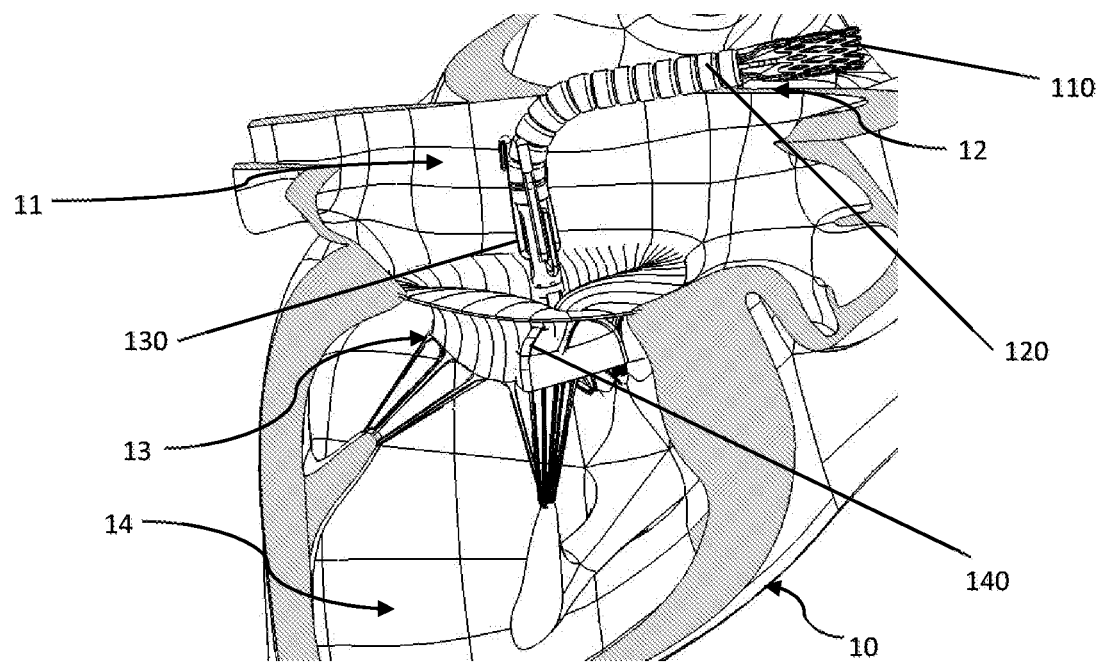
Figure 9D:
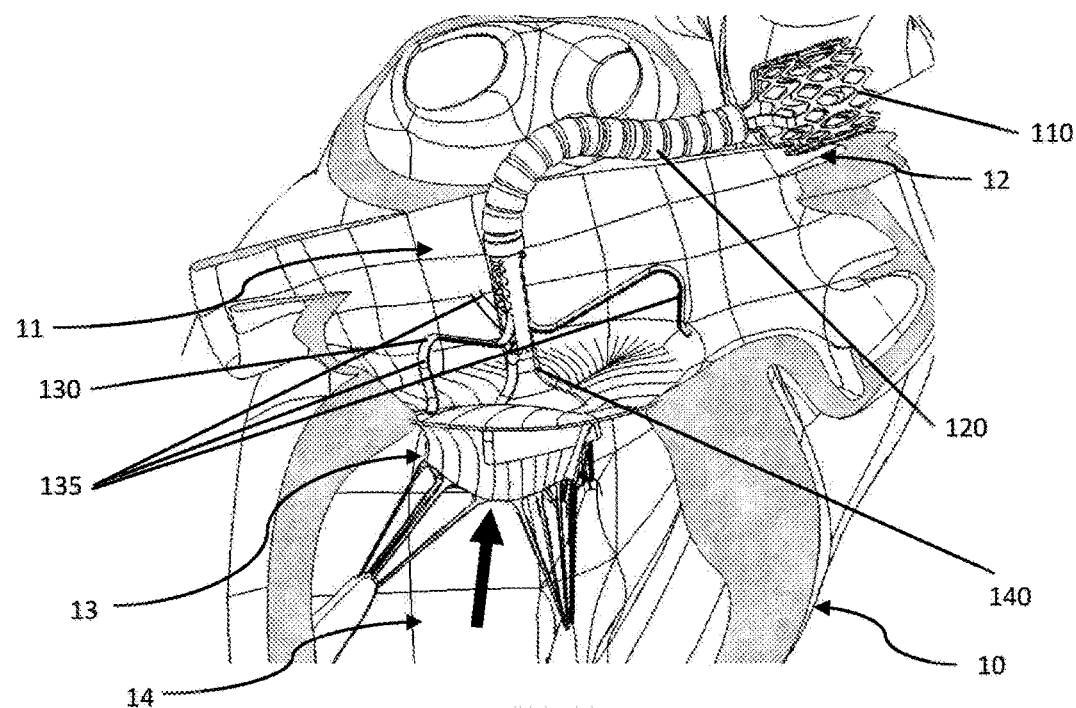
Figure 9E:
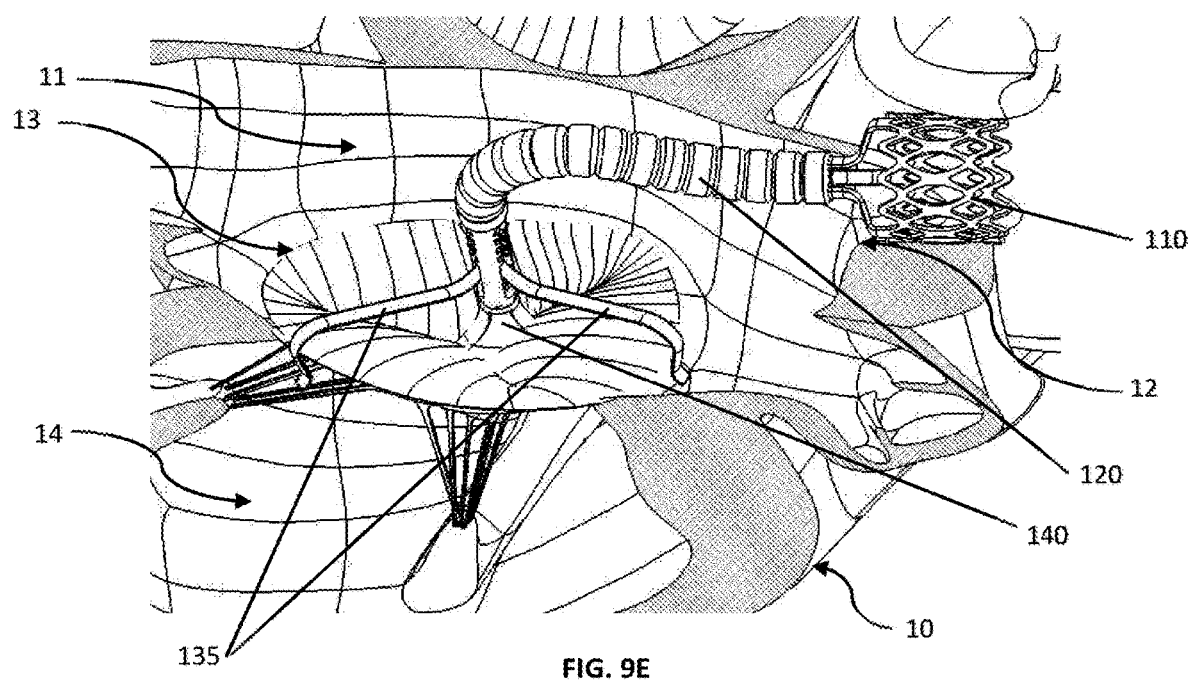
Figure 10:
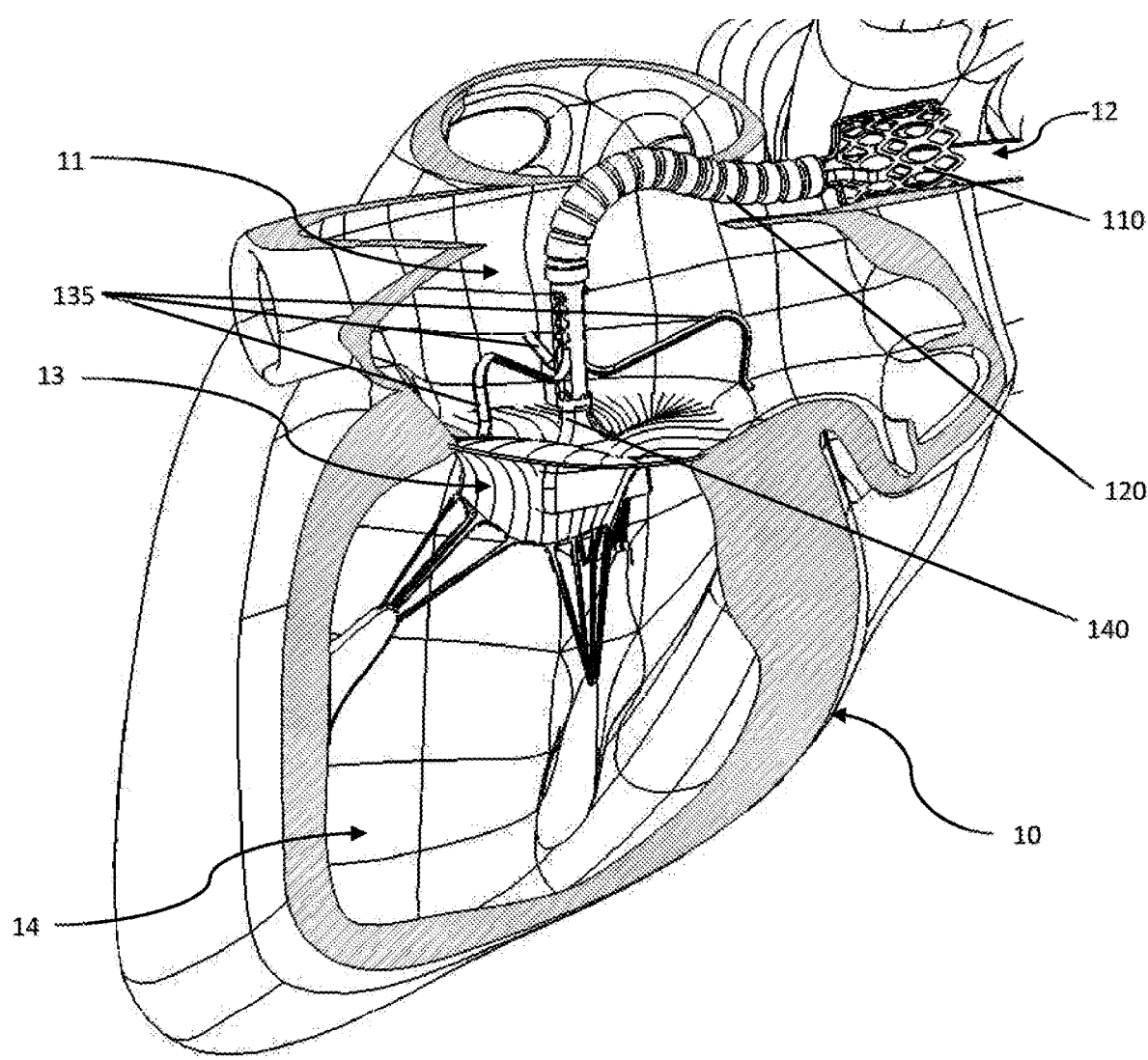
FIG. 10 is a wireframe drawing of an exemplary embodiment of a vena cava-anchored device fully deployed in a heart.

FIGS. 9A-9E illustrate the deployment sequence of device 100 into the heart 10 of a subject (for example, a patient). FIG. 9A illustrates that the device is inserted into the right atrium 11 via the SVC 12. Device 100 is housed within an intravascular delivery catheter (not shown) which holds device 100 in the crimped conformation. As illustrated in FIG. 9B, device 100 is deflected toward tricuspid valve 13 using the catheter steering mechanism. When aligned with tricuspid valve 13, device 100 can be pushed through into such that the distal end region of device 100 (and catheter) is located within the right ventricle 14. The flow optimizer 140 can be deployed as shown in FIG. 9C and device 100 is positioned such that flow optimizer 140 is disposed within tricuspid valve 13. The flow optimizer 140 can be deployed by a partial retraction of the catheter. As shown FIG. 9D, the arms 135 can be deployed such that the distal end regions of the arms 135 are seated on the top of tricuspid valve 13 and/or against the wall of atrium 11 so as to suspend flow optimizer 140 within the tricuspid valve 13. Optionally, arms 135 can be height-adjusted as described herein. FIG. 9E provides a perspective view of a fully deployed device 100. FIG. 10 provides a wire drawing illustrating a fully deployed device 100 within the heart 10.

Atrium/Ventricle-Anchored Tricuspid Valve Support Device—200

Figure 11A:
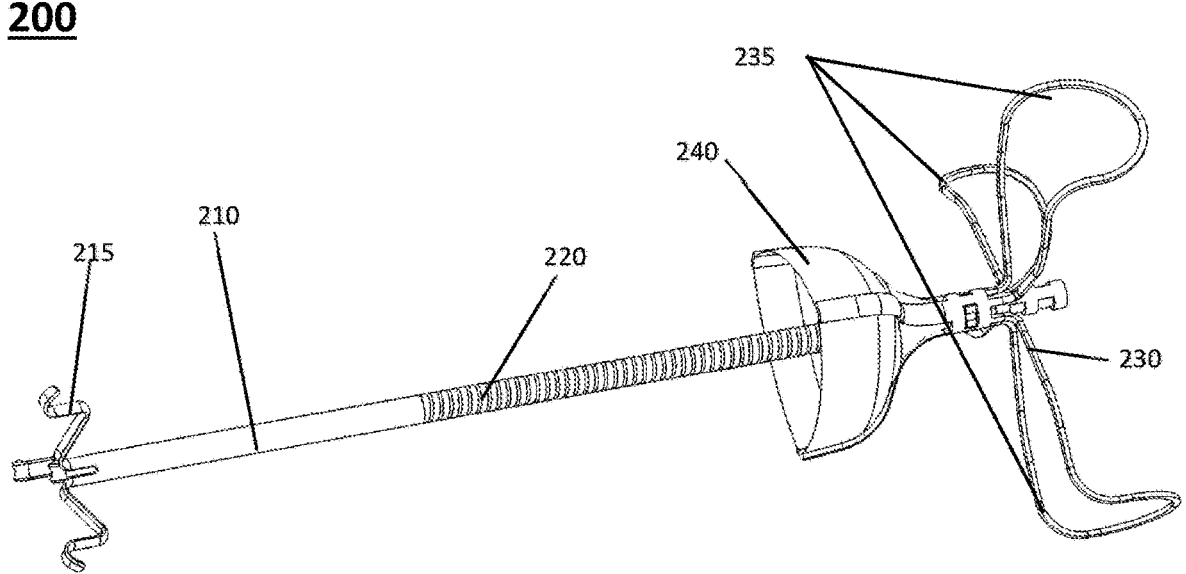
FIG. 11A is a schematic of an exemplary embodiment of an atrium and/or ventricle-anchored device in a deployed conformation.
Figure 11B:
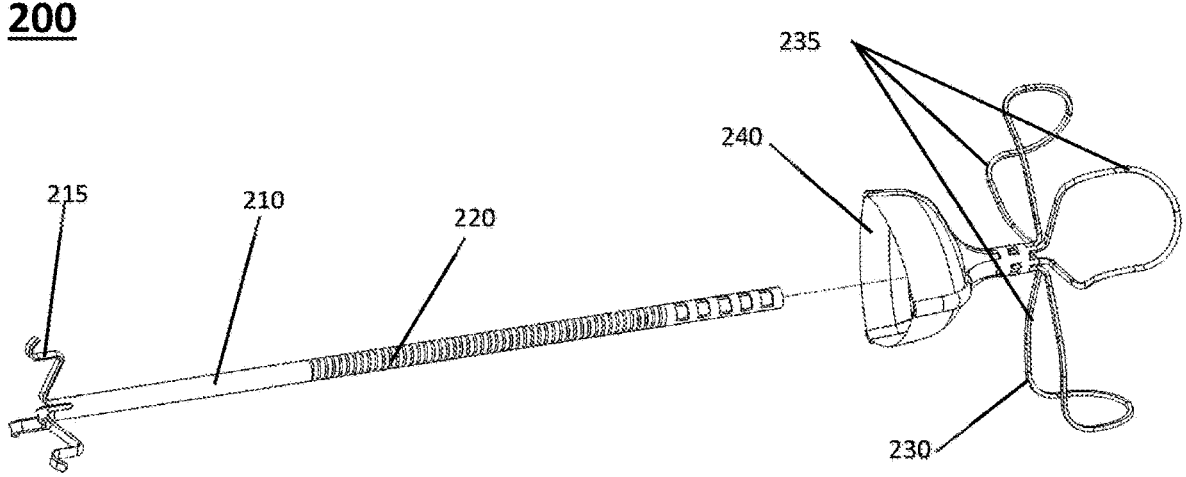
FIG. 11B is an exploded view of an exemplary embodiment of an atrium and/or ventricle-anchored device in a deployed conformation.
Figure 12A:
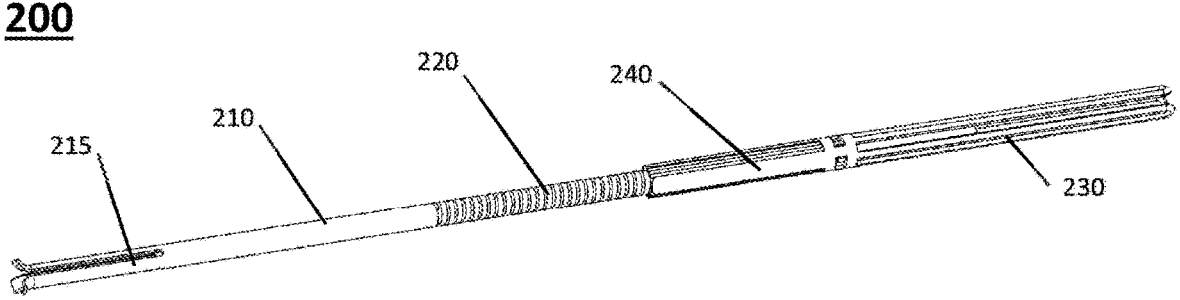
FIG. 12A is a schematic of an exemplary embodiment of an atrium and/or ventricle-anchored device in a crimped conformation.
Figure 12B:
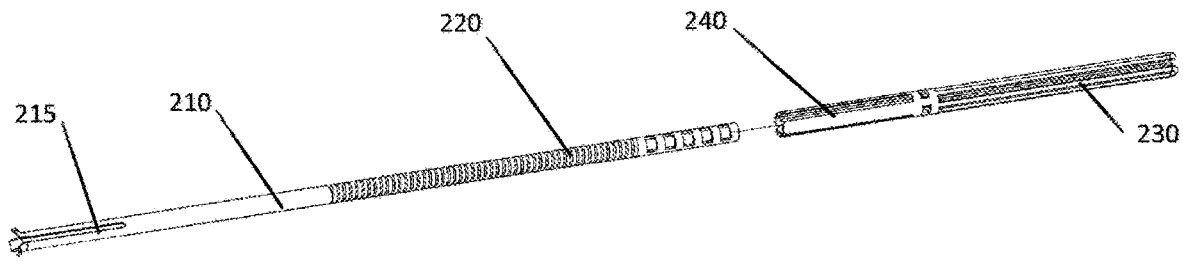
FIG. 12B is an exploded view of an exemplary embodiment of an atrium and/or ventricle-anchored device in a crimped conformation.

FIG. 11A illustrates a tricuspid valve support device 200, in a deployed conformation, configured to be anchored in the right ventricle and in the right atrium. FIG. 11A shows the device 200 as including a ventricular anchor 210, which can include one or more (e.g., one, two, three, four, or more) support arms 215, connected to an articulating link 220 which is attached to tricuspid valve flow optimizer 240. Additionally and/or alternatively, device 200 can further comprise an atrial anchor 230 that can have one or more (e.g., one, two, three, four, or more) arms 235. The arms 235 can be radially disposed from a central axis of device 200 and can be single ribbons or rods, or regular geometric or random shapes, as illustrated. FIG. 11B illustrates an exploded view of the tricuspid valve support device 200 in the deployed conformation. FIG. 12A illustrates the tricuspid valve support device 200 in a crimped conformation as the tricuspid valve support device 200 can be loaded into an intravascular delivery catheter (not shown). FIG. 12B illustrates an exploded view of the tricuspid valve support device 200, in a crimped conformation. Each of the device elements of the tricuspid valve support device 200 and the method for deployment is described in more detail below.

Ventricular Anchor 210

The ventricular anchor 210 is configured and adapted to support device 200 by resting against the inner wall of the right ventricle at and/or near the ventricle apex. In some embodiments, the ventricular anchor 210 contains a plurality of arms 215 on the distal side. The arms 215 can be formed from a memory shape material as described herein such that the arms 215 are self-expanding when released from the intravascular delivery catheter. The arms 215 can be formed from any suitable material, including memory shape materials such as NiTi. Additionally and/or alternatively, the arms 215 can comprise a friction enhancing layer (e.g., polymer) including, for example, Velcro® and micro-barbs, in order to enhance adhesion with the ventricular wall. Additionally and/or alternatively, the arms 215 can partially penetrate the ventricular wall in order to facilitate anchoring. The ventricular anchor 210 is attached to articulating link 220 on a distal end region of the articulating link 220.

Articulating Link 220

The articulating link 220 can have similar or the same construction as the articulating link 120, as described above in the context of device 100. A tricuspid valve flow optimizer 240 can be attached at a proximal end region of the articulating link 220.

Tricuspid Valve Flow Optimizer 240

The tricuspid valve flow optimizer 240 can have the same or similar construction as the tricuspid valve flow optimizer 140, as described above in the context of device 100. The tricuspid valve flow optimizer 240 can be supported from the ventricle at the ventricle apex by the articulating link 220 and from the atrium by the atrial anchor 230.

Additionally and/or alternatively, the flow optimizer 240 and the articulating link 220 can have a height adjustment mechanism to allow for more precise positioning of the flow optimizer 240 within the tricuspid valve. In one embodiment, illustrated in FIGS. 15A-15B and FIGS. 16A-16B, the articulating link 220 can have a centrally-disposed non-articulating attachment member 225 defining a plurality of notches 226. The flow optimizer 240 comprises a frame 242 having a centrally-disposed sleeve 244 which one or more detents 246 configured to mate with notches 226. The flow optimizer 240 positioning can be adjusted by sliding the frame 242 longitudinally along attachment member 225 such that the detents 246 disengage and re-engage with the notches 226. In one embodiment, the detents 246 are configured to allow sliding in only one direction. For example, unidirectional detents 246 are configured to allow translocation in the proximal direction (i.e., toward the ventricle apex). In another embodiment, the frame 242 and the attachment member 225 have a threaded engagement such that the operator can rotate the frame 242 to cause a translocation in either direction.

Atrial Anchor 230

Additionally and/or alternatively, the device 200 can comprises an atrial anchor 230 which extends proximally from the tricuspid valve flow optimizer 240 into the right atrium. When deployed, atrial anchor 230 rests on the inner wall of the right atrium above and/or adjacent to the annulus of the tricuspid valve, to provide additional support and stabilization to the tricuspid valve flow optimizer 240. The atrial anchor 230 can comprise one or more (e.g., one, two, three, four, or more) support arms 235. The arms 235 can be linear and/or contoured to conform to the atrial wall in and/or adjacent to the supra-annular region of the tricuspid valve. Alternatively, the arms 235 can each include a wire that defines a closed shape. Preferably, the atrial anchor 230 and/or the arms 235 are formed from a memory shape material (e.g., NiTi) such that they are self-expanding when released from the delivery catheter. Additionally and/or alternatively, the arms 235 can comprise, on the body-facing surface thereof, a friction enhancing layer (e.g., polymer) including, for example, Velcro® and micro-barbs, in order to enhance adhesion with the atrial wall.

In one embodiment, the atrial anchor 230 can be locked in the desired position relative to the articulating link 220 prior to loading the device 200 into the deliver catheter. The selection of the height positioning can be determined using imaging and/or other data obtained from the patient.

Additionally and/or alternatively, the atrial anchor 230 can be positioned proximally or distally relative to the articulating link 220 after deployment of the ventricular anchor 210 within the ventricle. For example, the atrial anchor 230 can be translocated relatively to the articulating link 220 via an internal operator-controlled lumen that is affixed to the central sleeves 244 of the flow optimizer 240. A secondary operator-controlled lumen connected to the proximal end of the articulating link 220 and covering the notches 226 can prevent the notches 226 from engaging with the detents 246 of the sleeves 244. Once the flow optimizer 240 is translocated to the desired position on the articulating link 220, the secondary operator-controlled lumen can be retrieved to expose the notches 226 thus allowing the detents 246 to engage with the notches 226 and lock the position of the flow optimizer 240 on the articulating link 220.

Deployment of Ventricle-Supported Device 200

Figure 13A:
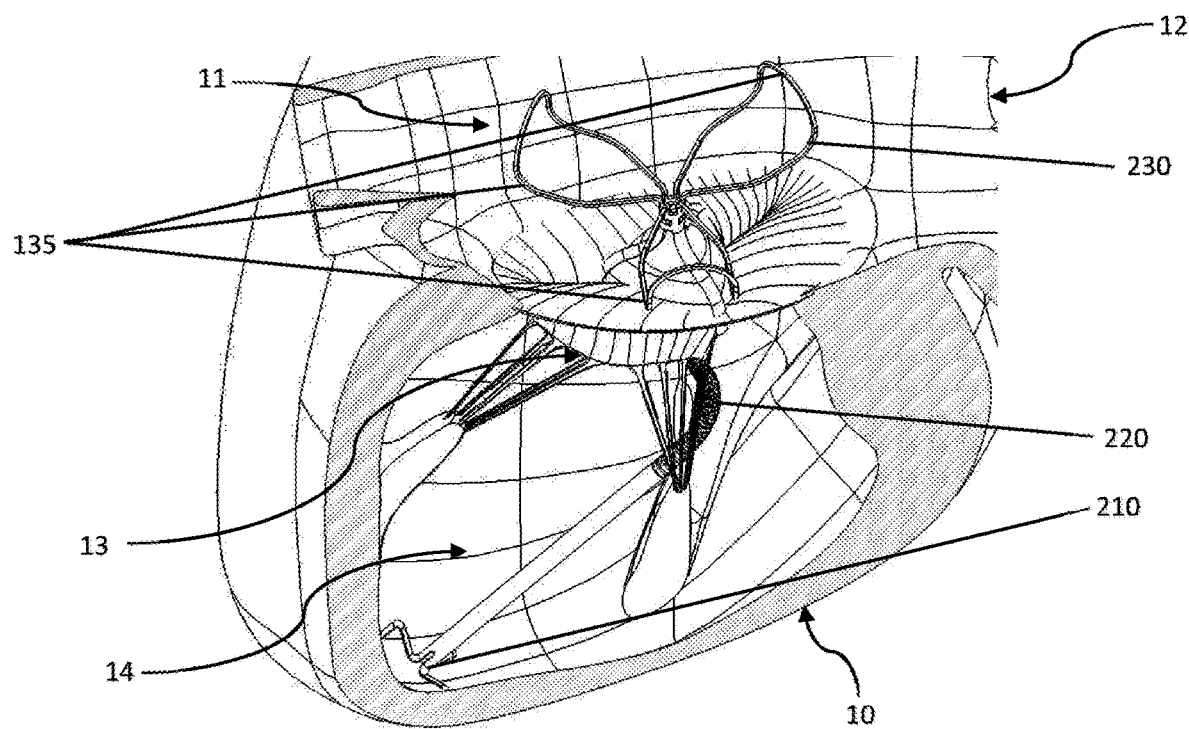
FIG. 13A is a wireframe drawing of an exemplary embodiment of an atrium ventricle-anchored device fully deployed in a heart.
Figure 13B:
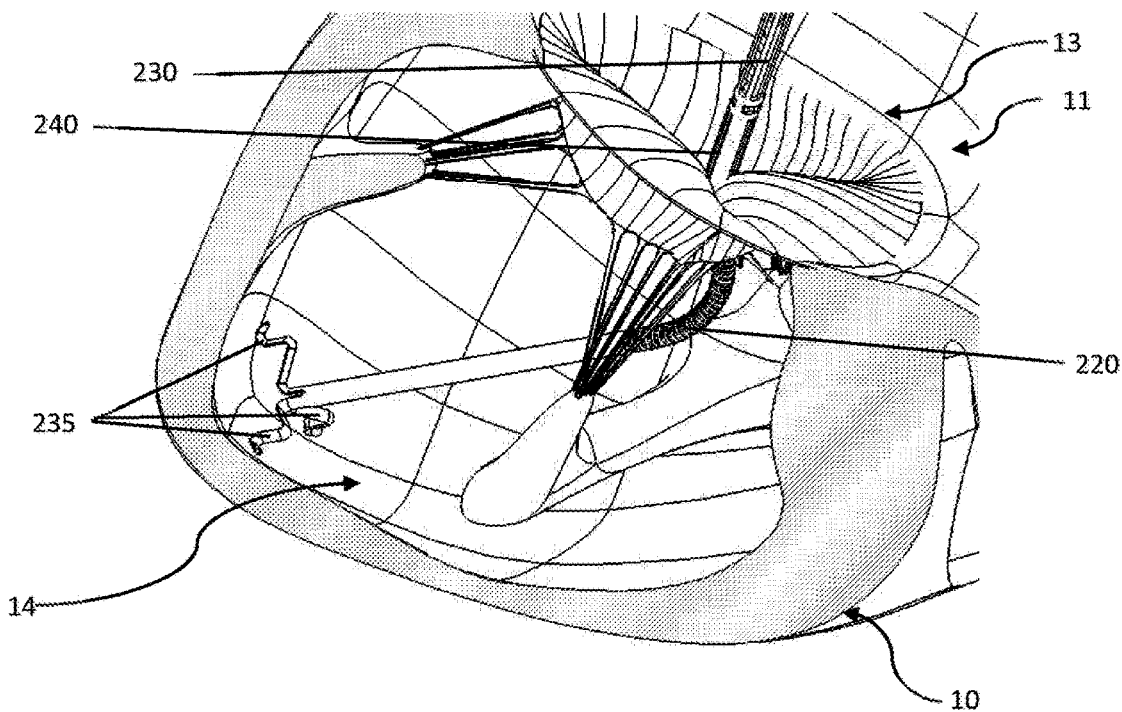
FIG. 13B is a wireframe drawing showing the deployed ventricle anchor of an exemplary embodiment of an atrium and/or ventricle-anchored device positioned at the ventricle apex.
Figure 14:
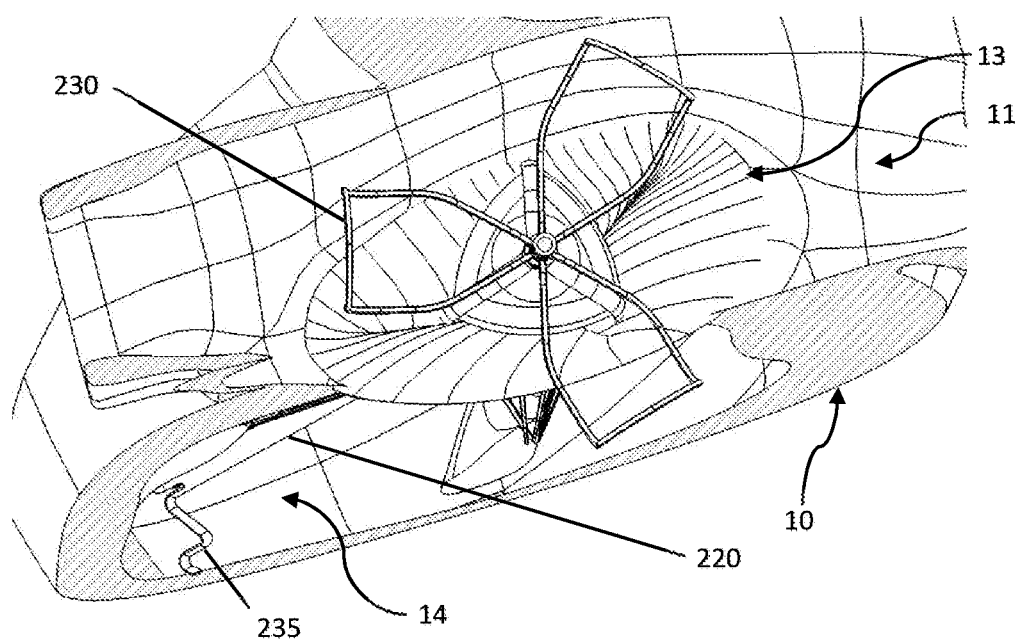
FIG. 14 is a schematic illustrating an exemplary embodiment of a deployed atrium and/or ventricle-anchored device viewed from the top of the right atrium.
Figure 15A:
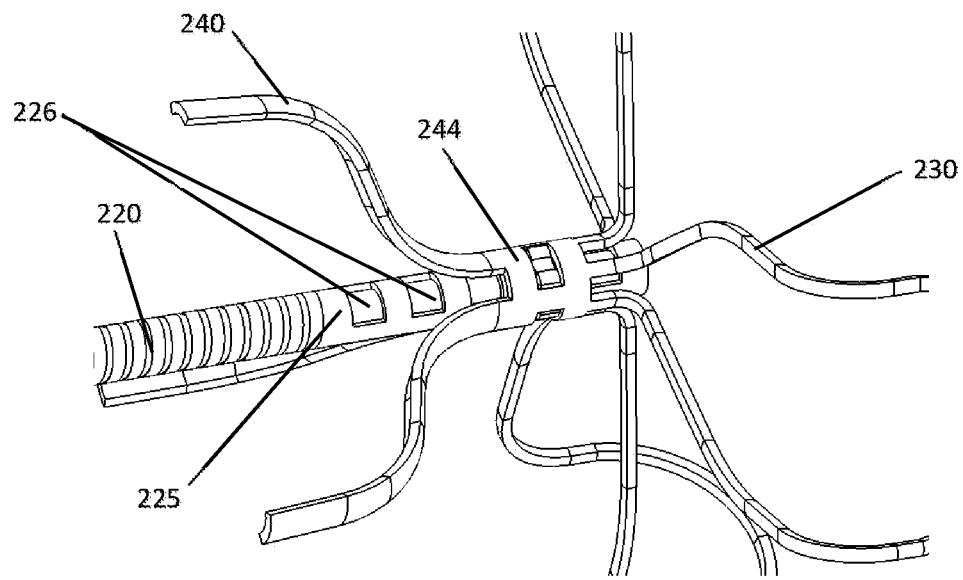
FIGS. 15A and 15B are schematics of an exemplary embodiment of a height adjustment mechanism suitable for use with a ventricle-anchored device.
Figure 15B:
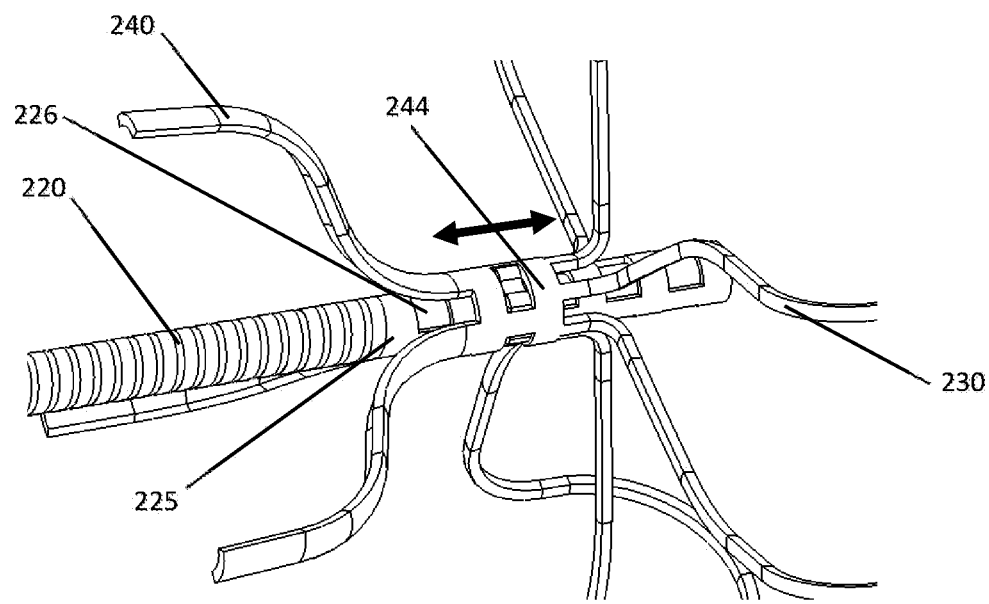
Figure 16A:
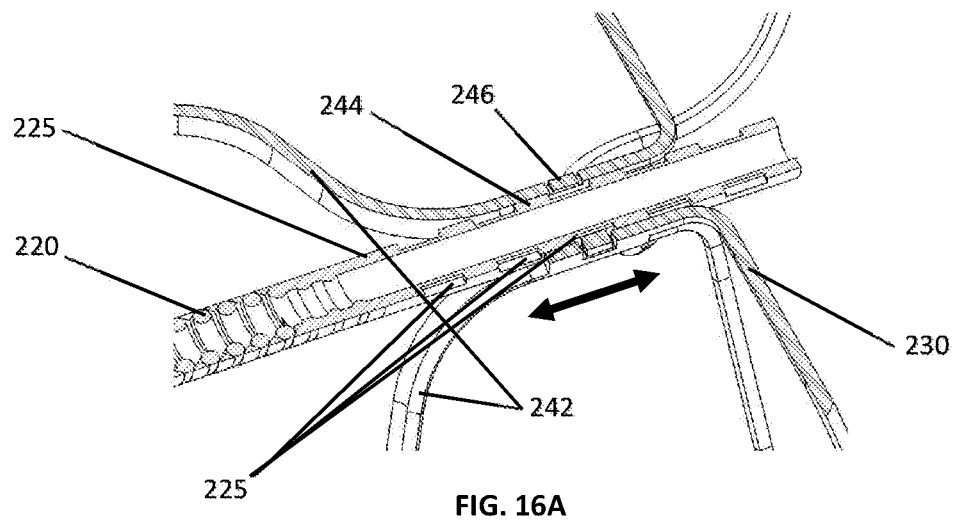
FIGS. 16A and 16B are cross-section views of an exemplary embodiment of a height adjustment mechanism suitable for use with a ventricle-anchored device.
Figure 16B:
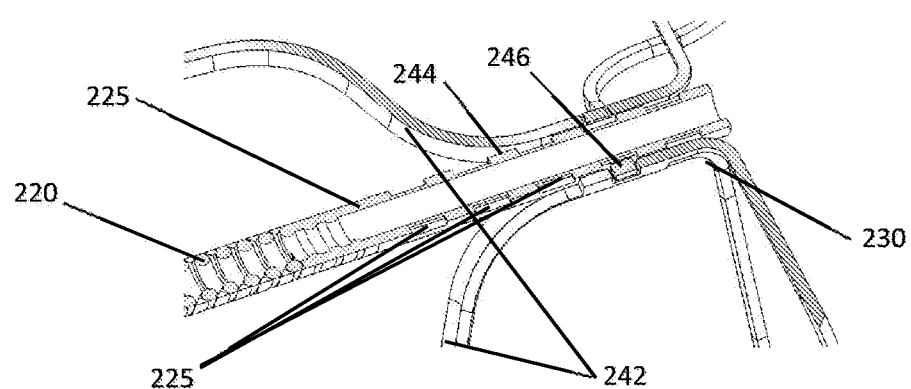

Similarly to the deployment of device 100, device 200 can be deployed using an intravascular catheter (not shown) and delivered through either the SVC or IVC. The catheter is pushed through the tricuspid valve from the right atrium into the right ventricle, with the catheter lumen positioned near the ventricle apex. The catheter's outer lumen can be partially retracted to deploy the ventricular anchor 210 and/or the arms 215. Using a catheter with steerable distal-end functionality, the positioning of device 200 can be adjusted to seat the ventricular anchor 210 at the ventricle apex. The catheter's outer lumen can be further retracted, exposing articulating link 220 and the flow optimizer 240. The articulating link 220 can be manipulated using the catheter's steerable distal end to seat the flow optimizer 240 at the desired location within the tricuspid valve. The catheter's outer lumen can be fully retracted, deploying the atrial anchor 230. FIG. 13A is a wireframe drawing showing device 200 fully deployed in the right atrium. FIG. 13B is an enlargement illustrating the positioning of the ventricular anchor 210 at the ventricle apex of the right ventricle. FIG. 14 is an illustration of a deployed device 200 viewed from the atrial side.

Right-Atrium Anchored Tricuspid Valve Support Device—300

Figure 18A:
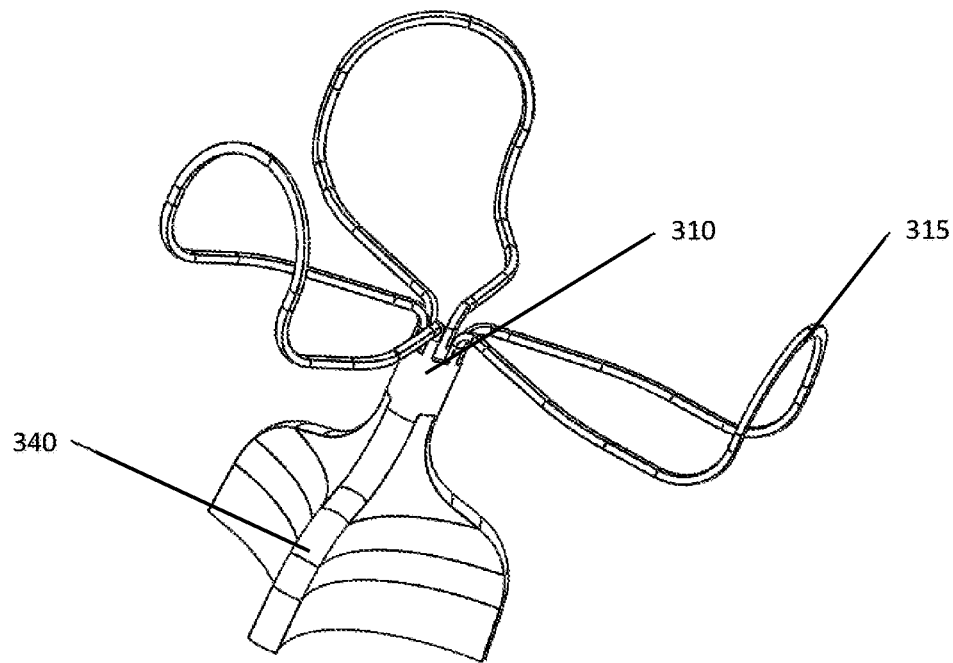
FIG. 18A is a schematic of an exemplary embodiment of an atrium-anchored device in the deployed conformation.
Figure 18B:
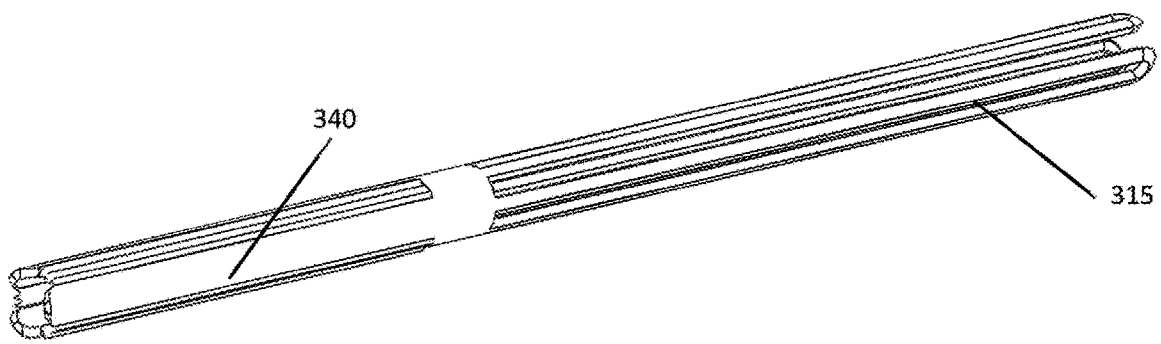
FIG. 18B is a schematic of an exemplary embodiment of an atrium-anchored device in the crimped conformation.
Figure 18C:
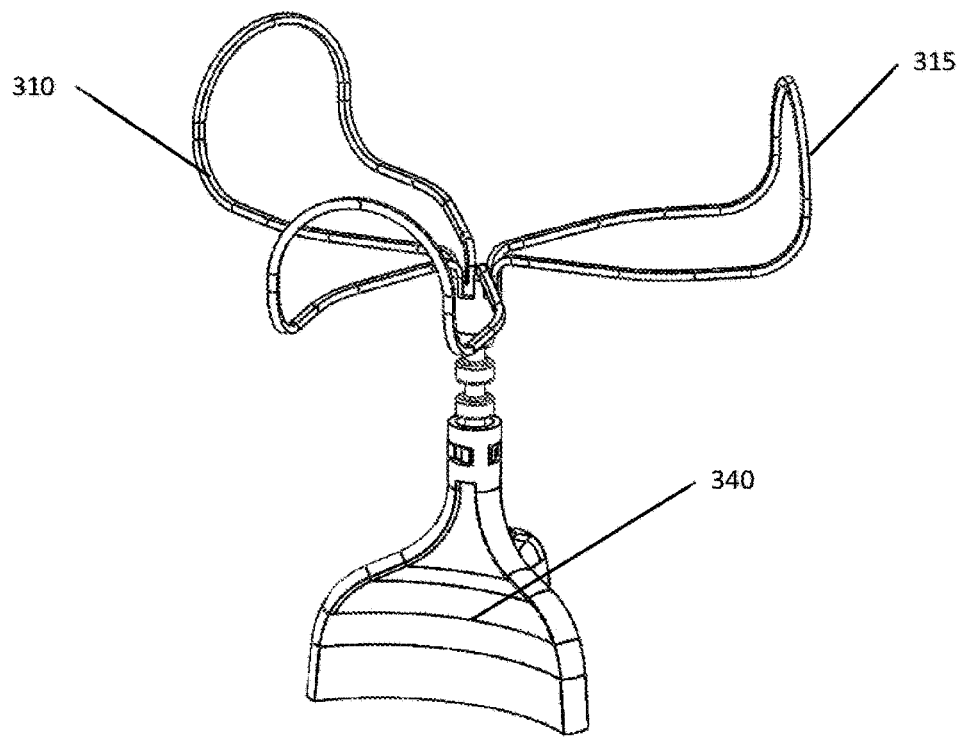
FIG. 18C is a schematic showing an exemplary embodiment of an atrium-anchored device with vertical height adjustment mechanism.

FIG. 18A illustrates a tricuspid valve support device 300, in a deployed conformation, configured to be anchored in the right atrium. FIG. 18A shows the device 300 as including an Atrial Anchor 310. The atrial anchor 310 can include one or more (e.g., one, two, three, four, or more) support arms 315, attached to tricuspid valve flow optimizer 340. The arms 315 can be radially disposed from the central axis of device 300 and can be single ribbons or rods, or regular geometric or random shapes, as illustrated. FIG. 18B illustrates the tricuspid valve support device 300 in a crimped conformation as the tricuspid valve support device 300 can be loaded into an intravascular delivery catheter. FIG. 18C illustrates the tricuspid valve support device 300 including an optional vertical height adjustment mechanism to vary the relative distance between the flow optimizer 340 and the atrial anchor 310. Each of the device elements and the method for deployment is described in more detail below.

Tricuspid Valve Flow Optimizer 340

The tricuspid valve flow optimizer 340 can have the same or similar construction as the tricuspid valve flow optimizer 140, as described above in the context of device 100. The tricuspid valve flow optimizer 340 can be supported from a proximal direction by the atrial anchor 310.

Atrial Anchor 310

Device 300 further comprises an atrial anchor 310 which extends proximally from the tricuspid valve flow optimizer 340 into the right atrium. When deployed, the atrial anchor 310 rests on the inner wall of the right atrium above and/or adjacent to the annulus of the tricuspid valve to provide support and stabilization to the tricuspid valve flow optimizer 340. The atrial anchor 310 can comprise one or more (e.g., one, two, three, four, or more) support arms 315. The arms 315 can be linear and/or contoured to conform to the atrial wall in and/or adjacent to the supra-annular region of the tricuspid valve, and they can have individual shapes and/or length. Alternatively, the arms 315 can include a wire that defines a closed shape, for example a looped shape. Preferably, the atrial anchor 310 and/or the arms 315 are formed from a memory shape material (e.g., NiTi) such that the atrial anchor 310 and/or the arms 315 are self-expanding when released from the delivery catheter. Optionally, the arms 315 further comprise on the body-facing surface a friction enhancing layer (e.g., polymer) including, for example, Velcro® and micro-barbs, in order to enhance adhesion with the atrial wall.

Figure 19A:
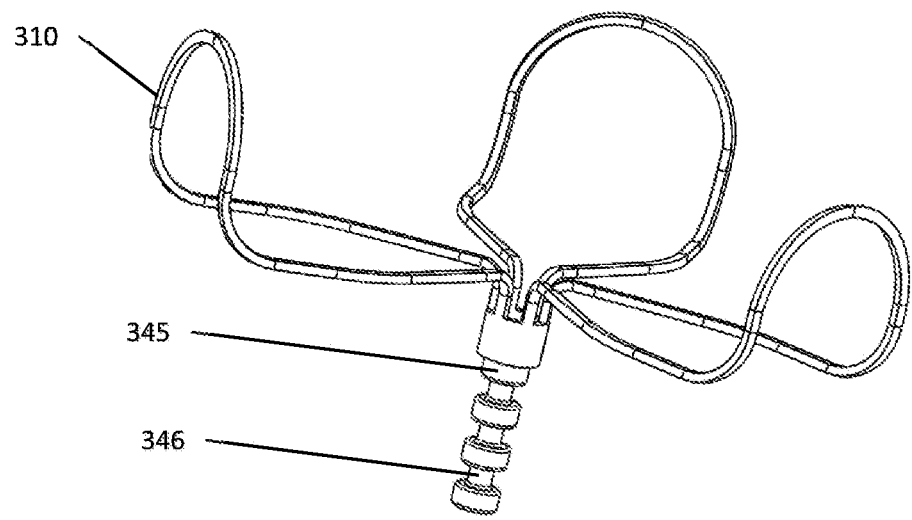
FIG. 19A is a schematic showing the atrium anchor component of an exemplary embodiment of an atrium anchored device having a height adjustment mechanism.
Figure 19B:
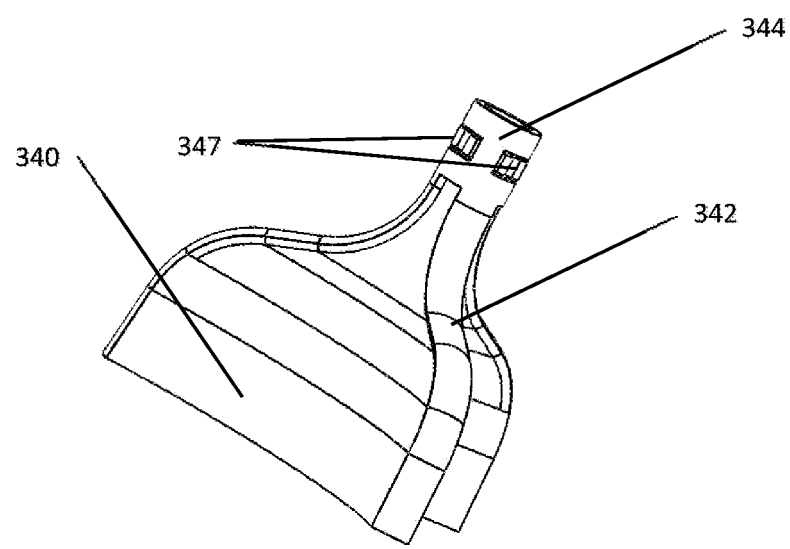
FIG. 19B is a schematic showing an exemplary embodiment of a tricuspid valve Flow optimizer component of an atrium-anchored device with a receiver portion for the height adjustment mechanism.
Figure 19C:
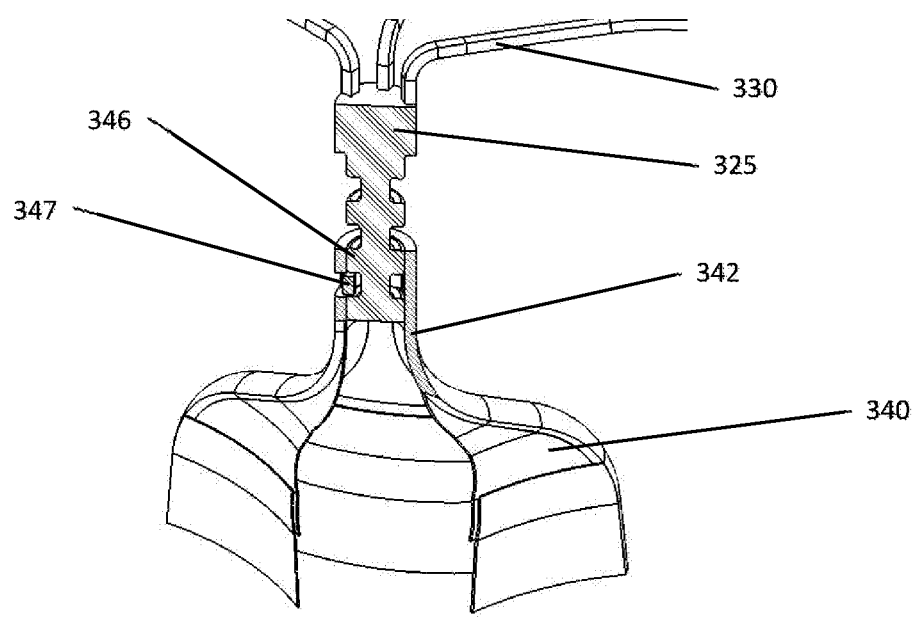
FIG. 19C is a schematic showing the cross section of an exemplary embodiment of a flow optimizer and an atrium anchor in a mated conformation through the height adjustment mechanism of atrium-anchored device 300.
Figure 20:
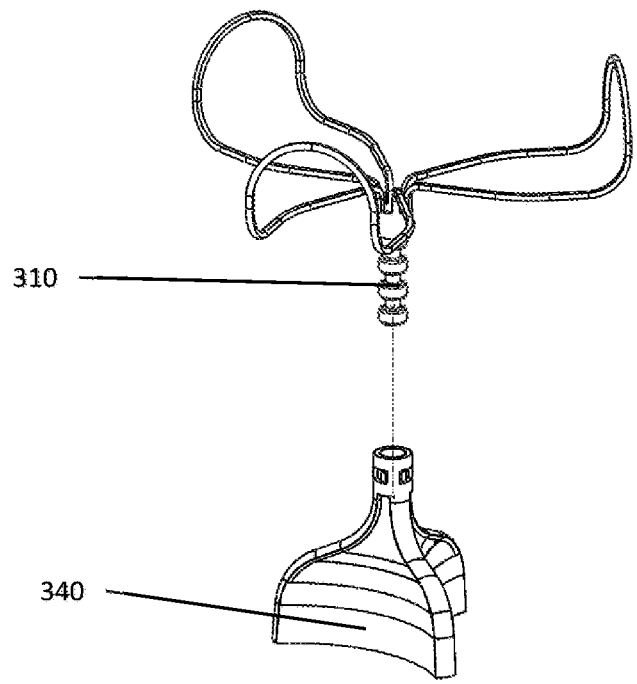
FIG. 20 is a wireframe drawing showing the exploded view of an exemplary embodiment of an atrium-anchored device in a deployed conformation.

Optionally, the flow optimizer 340 and the atrial anchor 310 can be coupled with a height adjustment mechanism to allow for more precise positioning of the flow optimizer 340 within the tricuspid valve. In one embodiment, illustrated in FIGS. 19A-19C and 20, the atrial anchor 310 has a centrally-disposed articulating or non-articulating attachment member 345 defining a plurality of notches 346. The flow optimizer 340 comprises a Frame 342 having a centrally-disposed sleeve 344 which one or more detents 347 configured to mate with notches 346. The flow optimizer 340 positioning can be adjusted by sliding the frame 342 longitudinally along attachment member 345 such that the detents 347 disengage and re-engage with the notches 346 as shown in FIG. 19C. In one embodiment, the notches 346 are configured to allow sliding in both distal and proximal directions. Optionally, unidirectional the notches 346 are configured to allow translocation in one direction, either distal (e.g., towards the ventricle) or proximal (e.g. towards the atrium). In another embodiment, the frame 342 and attachment member 345 have a threaded engagement such that the operator can rotate the frame 342 to allow a translocation in either direction.

In one embodiment, the atrial anchor 310 can be positioned in the desired position relative to the flow optimizer 340 prior to loading the device 300 into the deliver catheter. The selection of the height positioning can be determined using imaging and/or other data obtained from the patient.

Additionally and/or alternatively, the atrial anchor 310 can be positioned proximally or distally relative to the flow optimizer 340 after deployment of the device 300 within the atrium. For example, the atrial anchor 310 can be translocated relatively to the flow optimizer 340 via an internal operator-controlled lumen that is affixed to the proximal end of the flow optimizer 340. A secondary operator-controlled lumen connected to the distal end of anchoring mechanism 310 and covering the notches 346 can prevent the notches 346 from engaging with the detents 347. Once achieved the desired positioning of the flow optimizer 340 on the anchoring mechanism 310, the secondary operator-controlled lumen is retrieved to expose the notches 346 thus allowing the detents 347 to engage the notches 346 and lock the position of the flow optimizer 340 on the anchoring mechanism 310.

Deployment of Ventricle-Supported Device 300

Figure 21A:
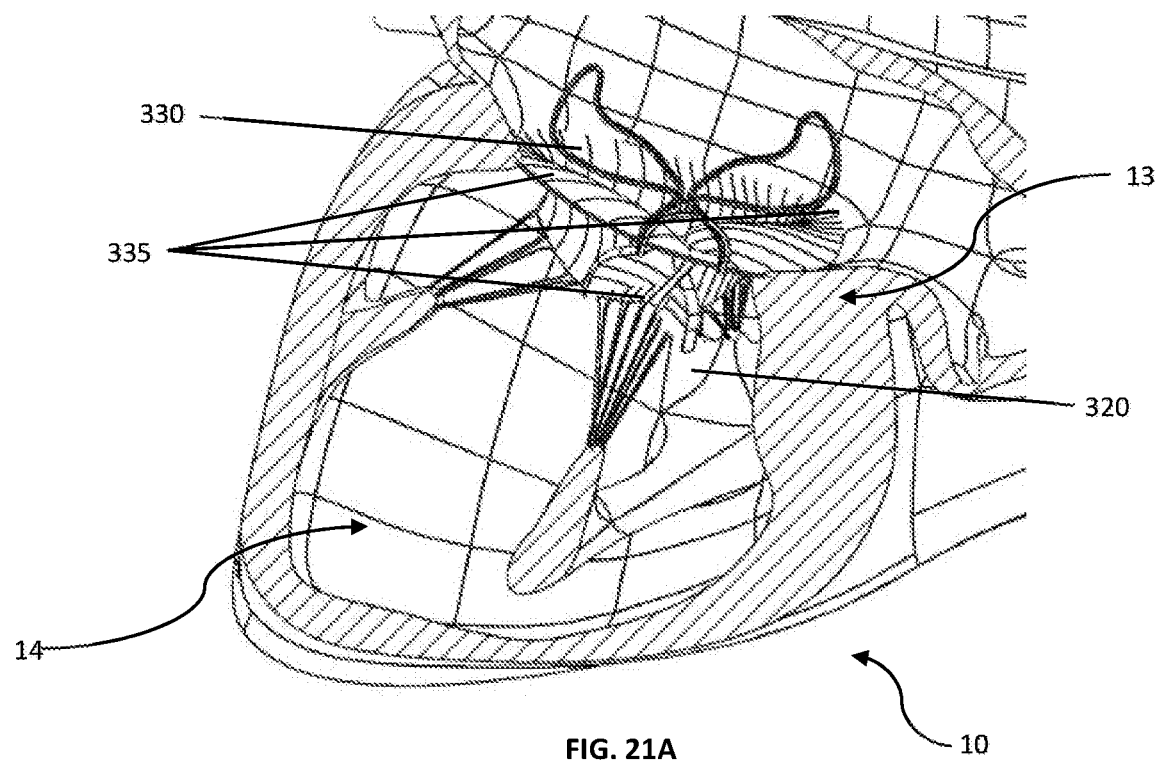
FIG. 21A is wireframe schematic showing an exemplary embodiment of an atrium anchored device as deployed in the tricuspid valve anatomy.
Figure 21B:
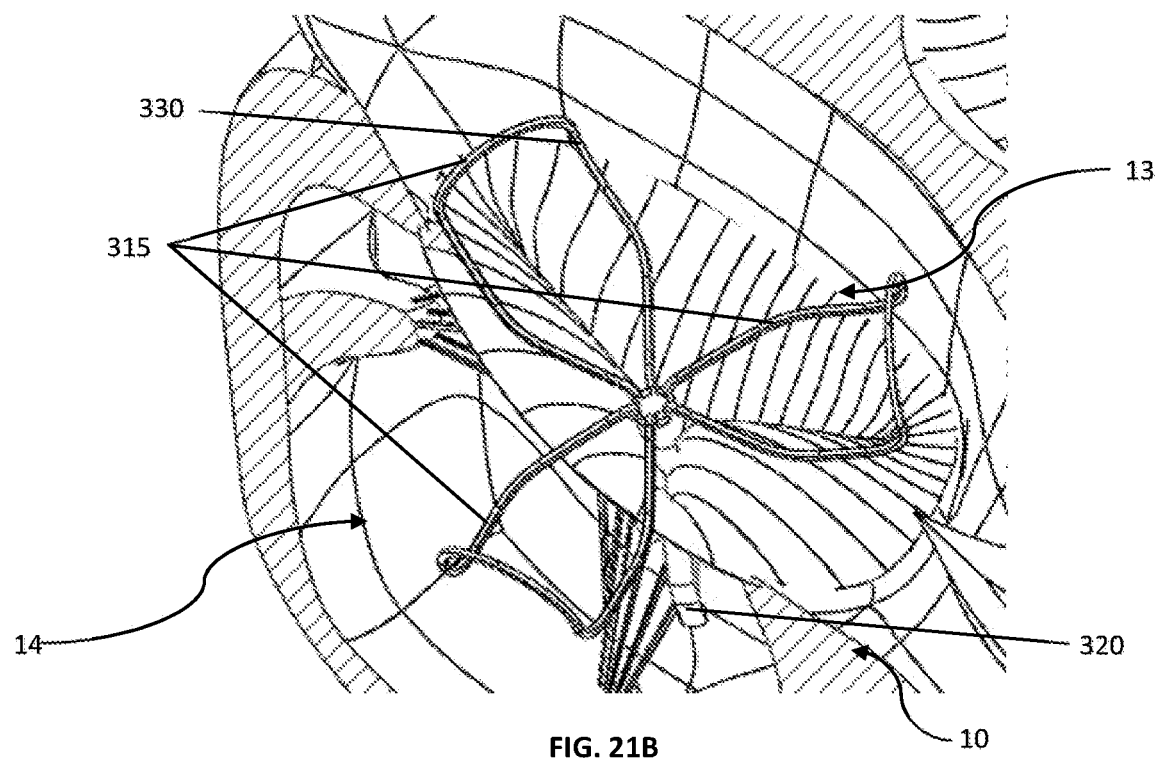
FIG. 21B is a wireframe schematic showing an exemplary embodiment of an atrium-anchored device as deployed in the tricuspid valve anatomy viewed from the right atrium.

Similarly to the deployment of device 100, the device 300 can be deployed using an intravascular catheter and delivered through either the SVC or IVC. For example, the catheter is pushed through the tricuspid valve from the right atrium into the right ventricle, with the catheter lumen positioned near the ventricle apex. The catheter can be partially retracted, exposing the flow optimizer 340 and the atrial anchor 330. The catheter can be further retracted to deploy the shortest of the atrial anchor arms 315. The catheter can be fully retracted deploying all remaining atrial arms 315. FIG. 21A is a wireframe drawing showing device 300 fully deployed in the right atrium. FIG. 21B is an illustration of a deployed device 300 viewed from the atrial side.

Commissures Anchored Tricuspid Valve Support Device—400

Figure 25:
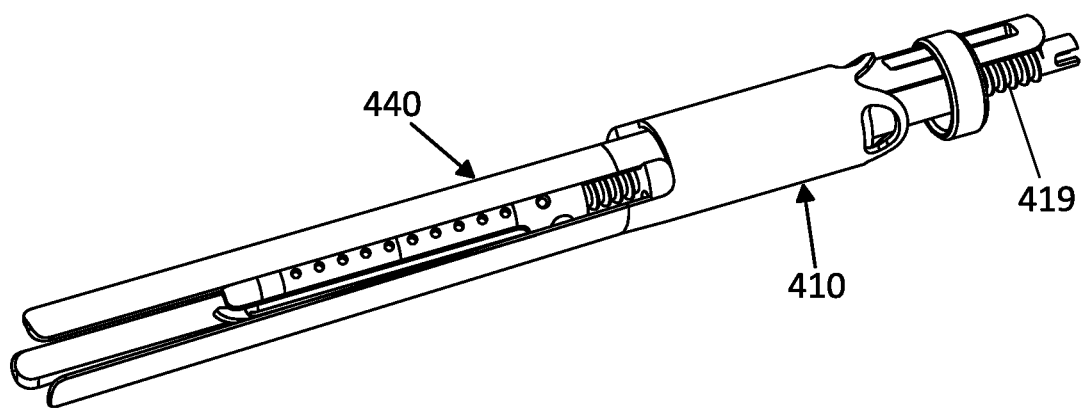
FIG. 25 is a schematic of an exemplary embodiment of a commissures-anchored device in a crimped conformation.

FIGS. 22A-B and FIGS. 23A-B illustrate a tricuspid valve support device 400, in a deployed conformation, configured to be anchored at the annulus of the tricuspid valve in correspondence of commissures of the native leaflets of the tricuspid valve. Generally, the device 400 comprises an anchoring mechanism 410, which can contain one or more (e.g., one, two, three, four, or more) support arms 415, and its connected via a threaded shaft 419 to the tricuspid valve flow optimizer 440. The arms 415 can be radially disposed from the central axis of the device 400 and can be single ribbons or rods defining geometric, regular and/or random shapes, as illustrated. Alternatively, the arms 415 can be formed by a wire defining a closed shape. The end region (or distal end region) 416 of the arms 415a-415c is contoured to mate with the tissue wall of the tricuspid valve annulus at the commissures of the native leaflets. The intermediate portion 417 of the arm 415 is shaped to conform to the inner supra-annular wall of the right atrium to provide further support and/or stabilization. FIG. 25 illustrates the tricuspid valve support device 400 in a crimped conformation as it can be loaded into an intravascular delivery catheter. Each of the device elements and the method for deployment is described in more details below.

Tricuspid Valve Flow Optimizer 440

Tricuspid valve flow optimizer 440 can have similar or the same construction as the tricuspid valve flow optimizer 140, as described above in the context of device 100. The tricuspid valve flow optimizer 440 can be connected to the threaded shaft 419. The tricuspid valve flow optimizer 440 can be supported in the proximal direction by commissures/atrial wall anchoring mechanism 410 via the threaded shaft 419.

Although FIGS. 22A-23B shows the shaft 419 as being threaded, the shaft 419 can be threaded and/or non-threaded, without limitation. The anchoring mechanism 410 can be connected to the shaft 419 via any mechanism that is same as and/or different from threading.

Commissures Anchoring Mechanism 410

Figure 24A:
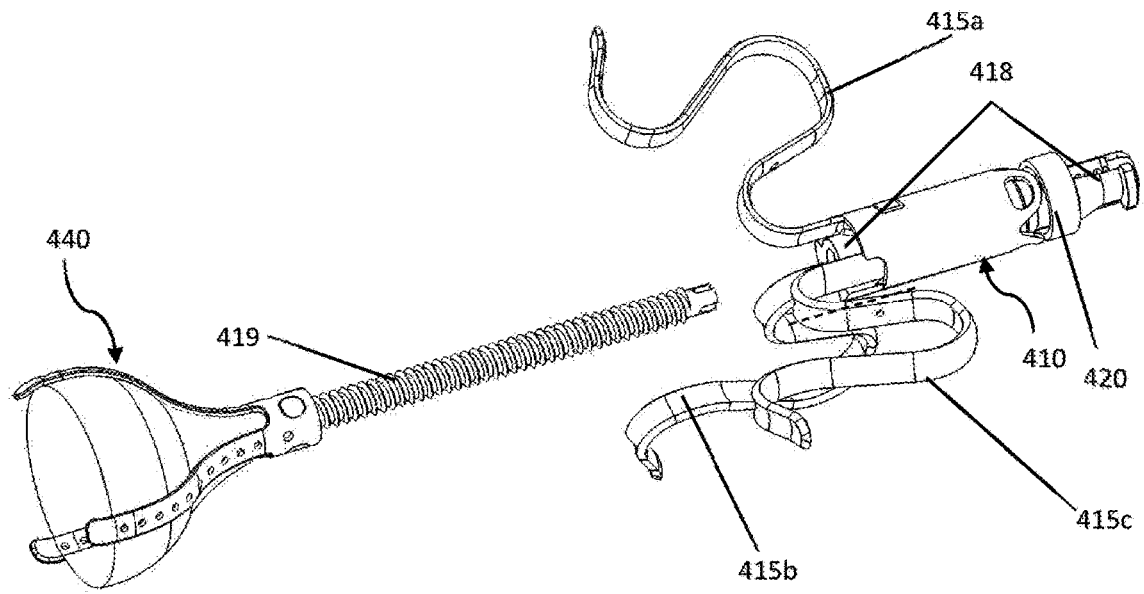
FIG. 24A is a schematic of an exemplary embodiment of a commissures-anchored device in a deployed conformation with the anchoring mechanism 410 separated from the flow optimizer 440.
Figure 24B:
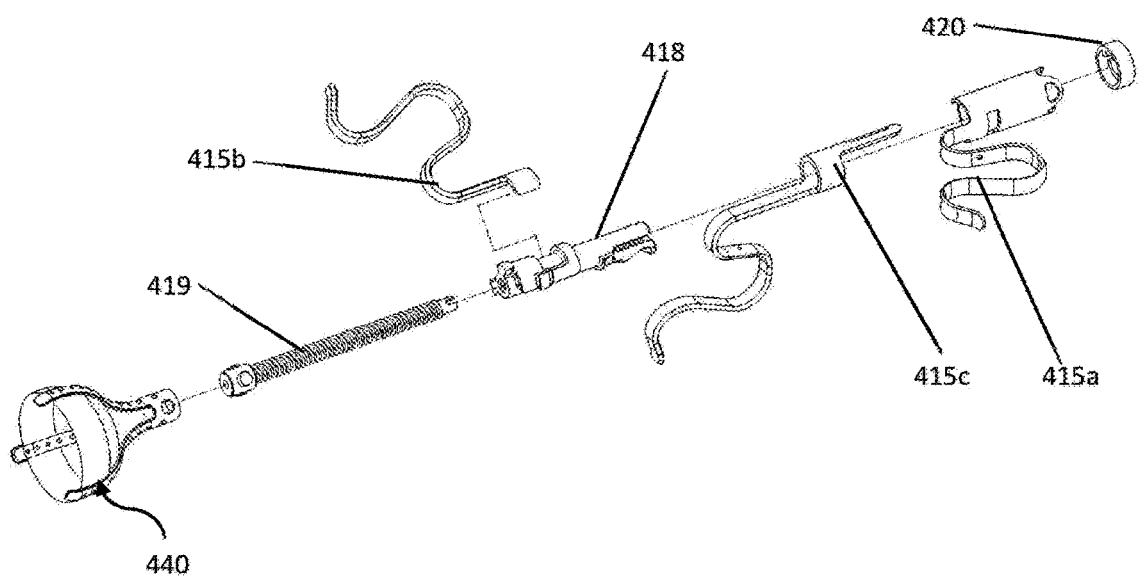
FIG. 24B is an exploded view of an exemplary embodiment of a commissures-anchored device in a deployed conformation.
Figure 26:
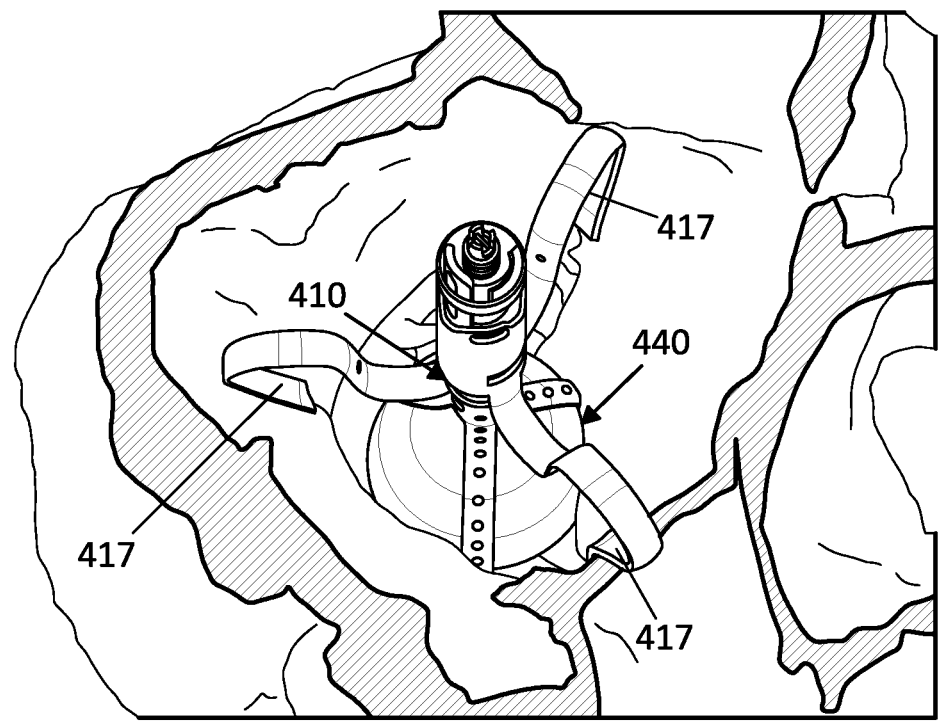
FIG. 26 is a schematic atrial view of an exemplary embodiment of a commissures-anchored device in a deployed conformation within the heart anatomy.
Figure 27:
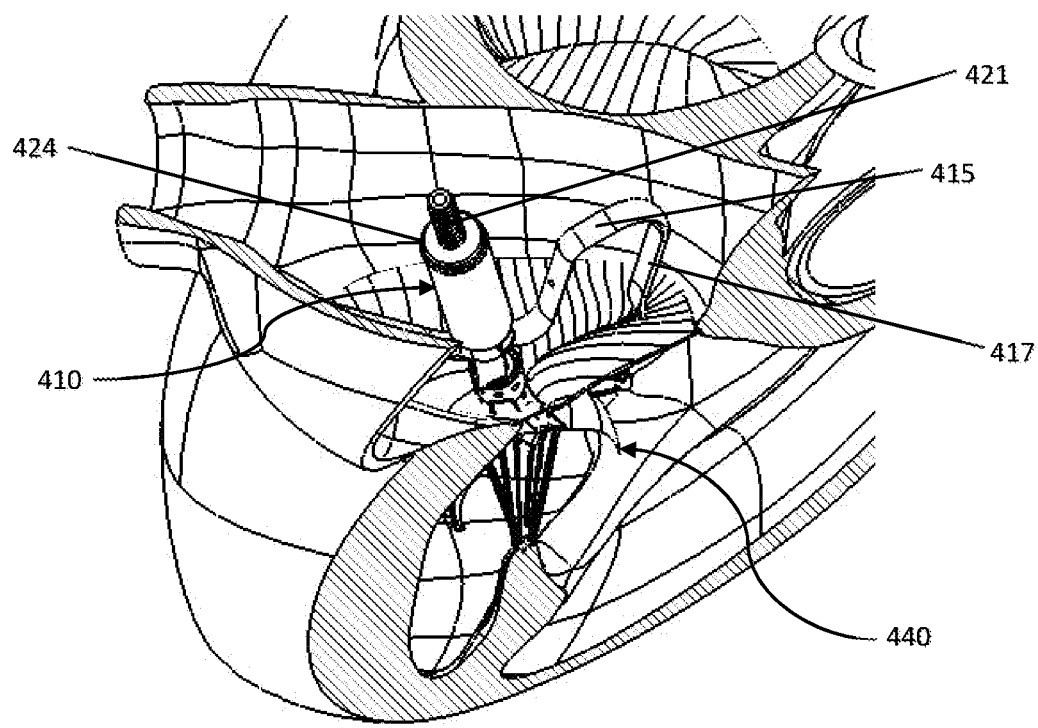
FIG. 27 is an atrial schematic view of an exemplary embodiment of a commissures-anchored device in a deployed conformation within the heart anatomy showing the placement of an anchoring arm within the tricuspid valve commissure.
Figure 28:
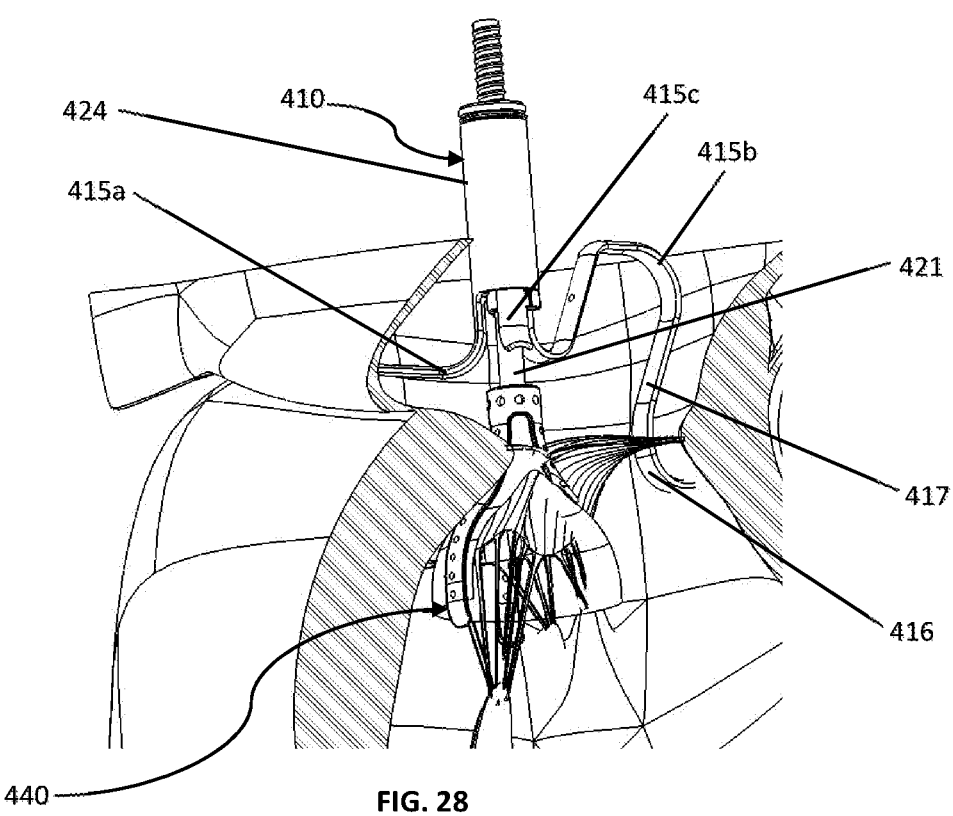
FIG. 28 is a ventricular schematic view of an exemplary embodiment of a commissures-anchored device in a deployed conformation within the heart anatomy showing the placement of an anchoring arm within the tricuspid valve leaflets' commissure.
Figure 29A:
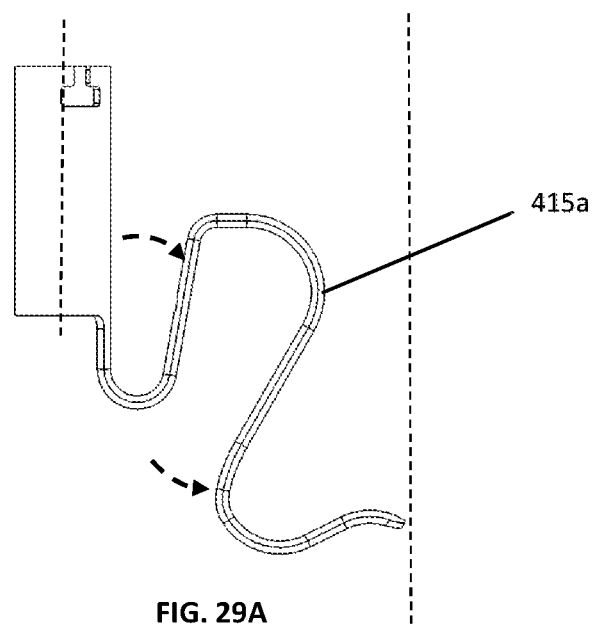
FIGS. 29A and 29B are schematic views of an anchoring arm of an exemplary embodiment of a commissures-anchored device shown in different expansion conformations.
Figure 29B:
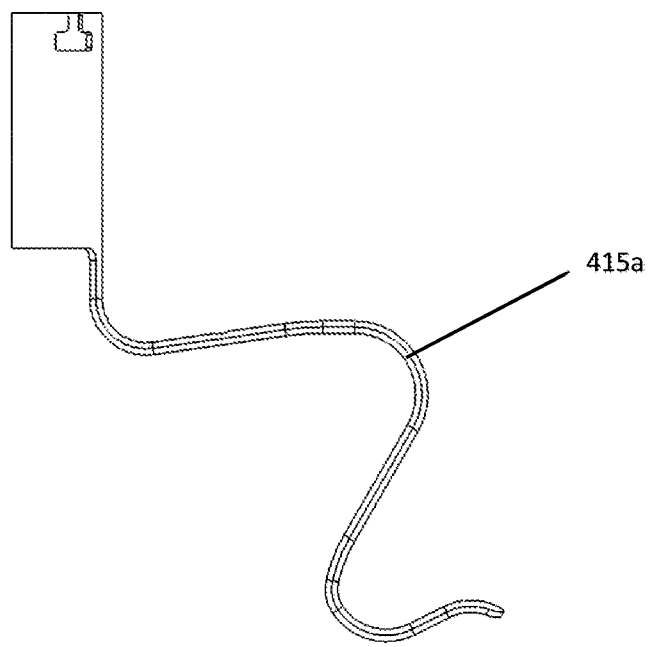

As shown in FIG. 24A, the Device 400 further comprises commissures anchoring mechanism 410 which extends proximally from tricuspid valve flow optimizer 440 into the right atrium (not shown). The commissures anchoring mechanism 410 can comprise one or more (e.g., one, two, three, four, or more) anchoring arms 415. The anchoring arms 415 can have identical or individual shapes and/or length (shown in FIG. 24B). As shown in FIGS. 26-28, when deployed, the end regions (or the distal end regions) 416 of the arms 415a-415c mate with the tissue wall of the tricuspid valve annulus at the commissures of the leaflets, and the intermediate portion 417 rests against the inner supra-annular wall of the right atrium to provide further retention and stabilization to the tricuspid valve flow optimizer 440. Preferably, the arms 415a-415c are formed from a memory shape material (e.g., NiTi) such that they are self-expanding when released from the delivery catheter. As an example, FIGS. 29A-29B show an exemplary range of expansion of the shape of the arm 415a from the center axis of the device. The arm 415a can expand into either of the shapes shown in FIGS. 29A-29B and/or any intermediate shapes between the shapes shown in FIGS. 29A-29B, allowing placement and/or fitting of commissures anchoring mechanism 410 in tricuspid valve annuli of variable shape and size. Similar range of displacement applies to the arms 415a-415c. Optionally, the arms 415a-415c can comprise, on the tissue-facing surface, a friction enhancing layer (e.g., polymer) including, for example, Velcro® and micro-barbs, in order to enhance adhesion with the tissue at the commissures and at the inner supra-annular wall. The inner core 418, threaded shaft 419, locking collar 420 as shown in FIG. 24B can be machined from standard metallic alloys or polymers.

Figure 22A:
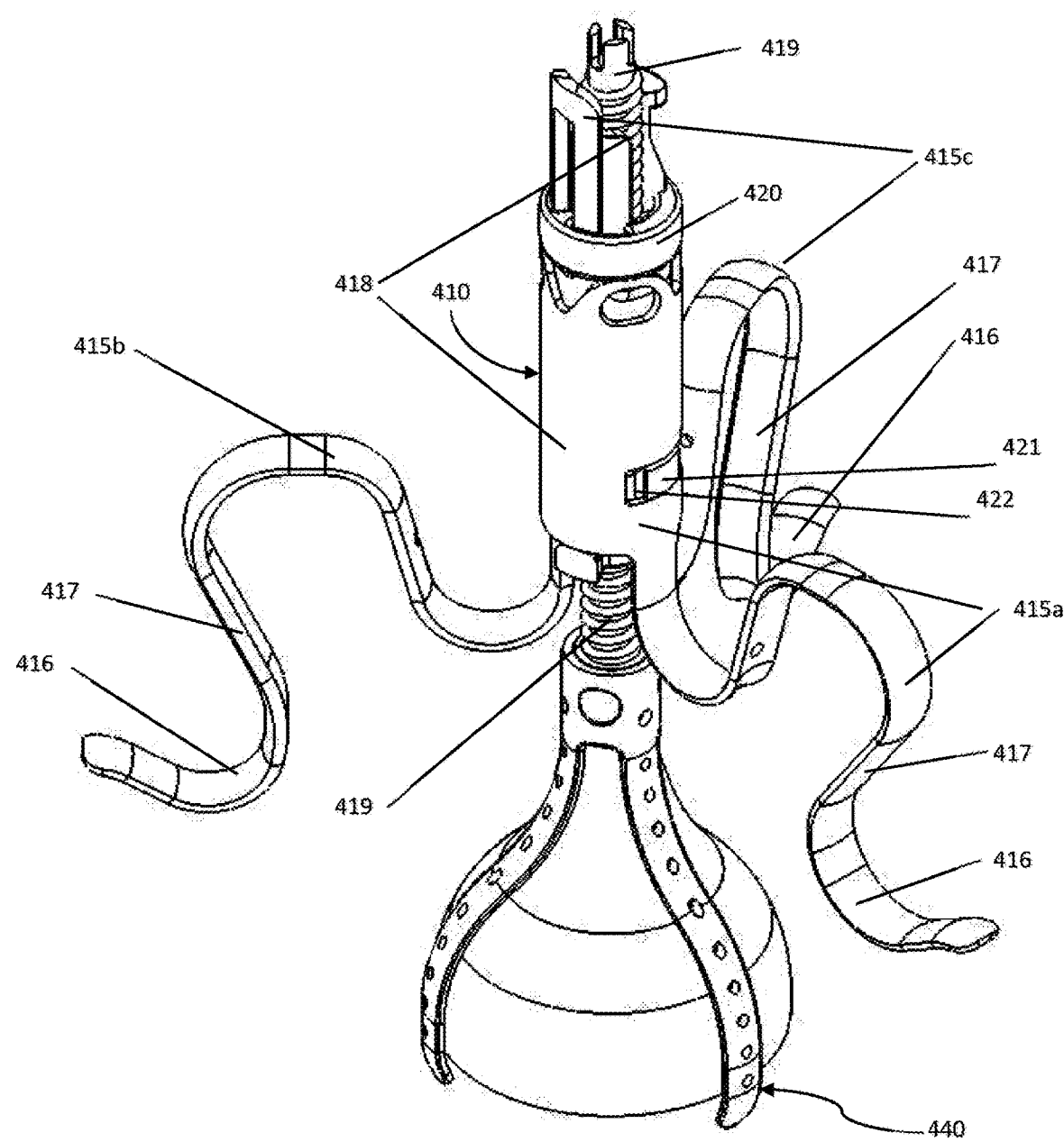
FIG. 22A is a schematic of an exemplary embodiment of a commissures-anchored device in a deployed conformation.
Figure 22B:
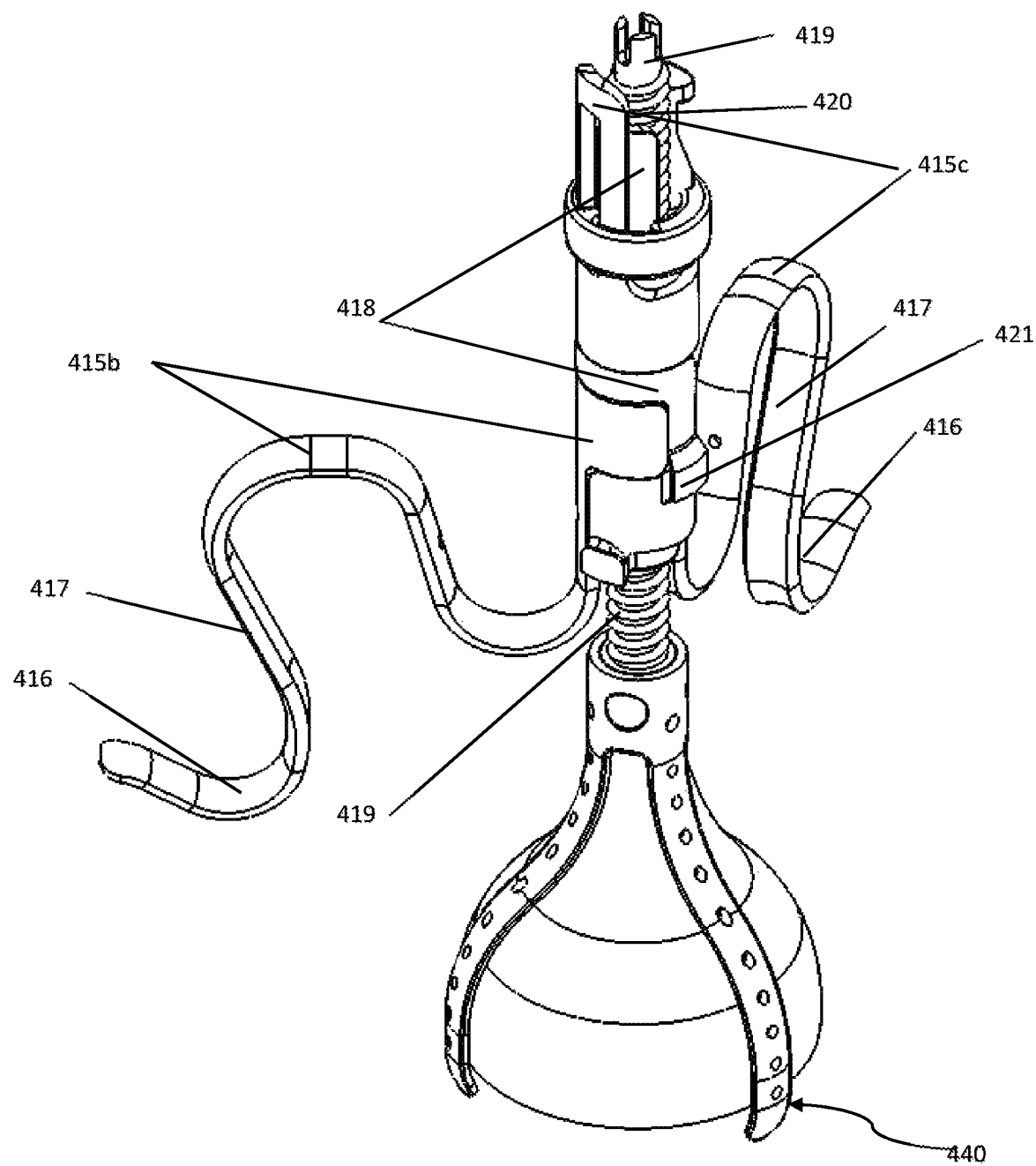
FIG. 22B is a schematic illustrating an exemplary embodiment of a commissures-anchored device in a deployed conformation with arm 415a not displayed to allow visualization of the Anchoring mechanism 410 internal components.
Figure 22C:
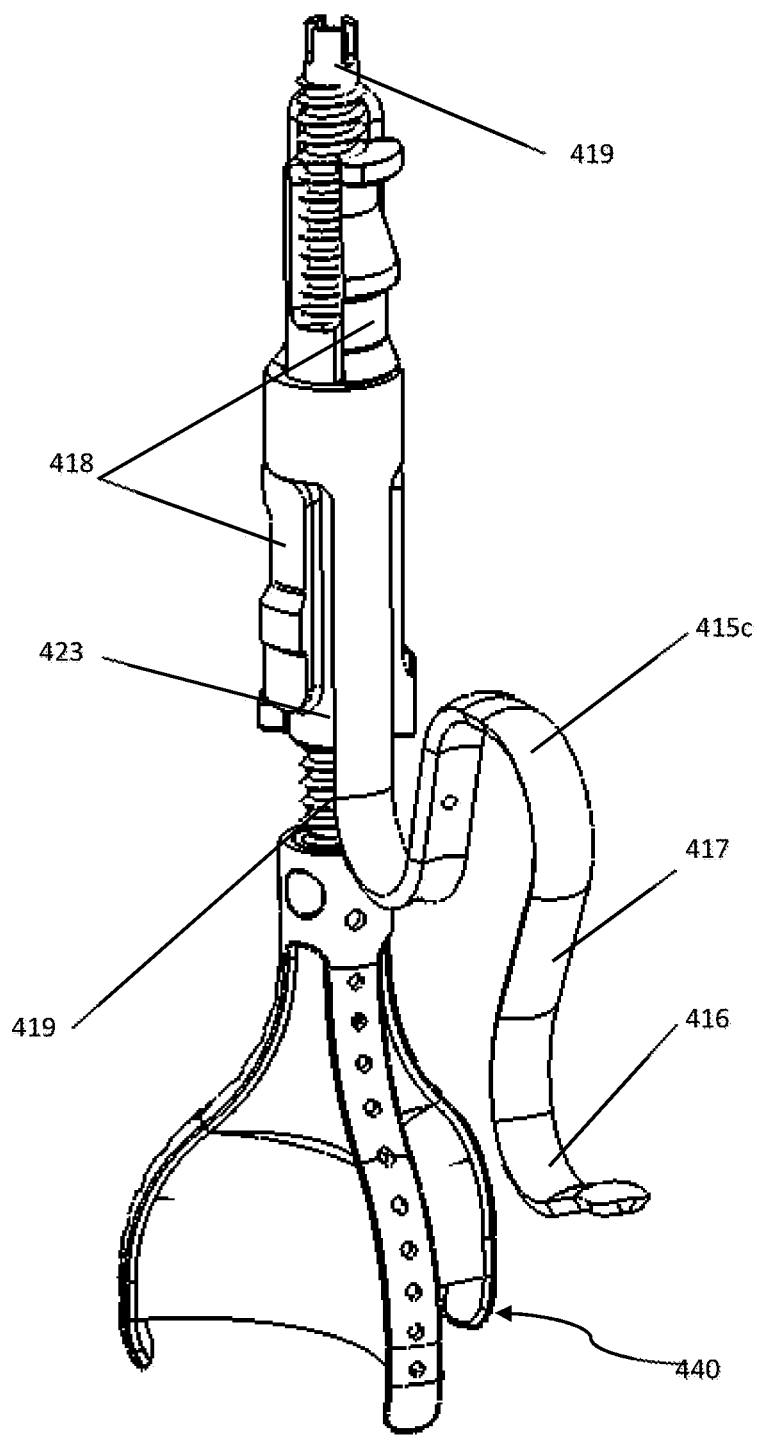
FIG. 22C is a schematic illustrating an exemplary embodiment of a commissures-anchored device in a deployed conformation with arms 415a and 415b not displayed to allow visualization of the Anchoring mechanism 410 internal components.
Figure 22D:
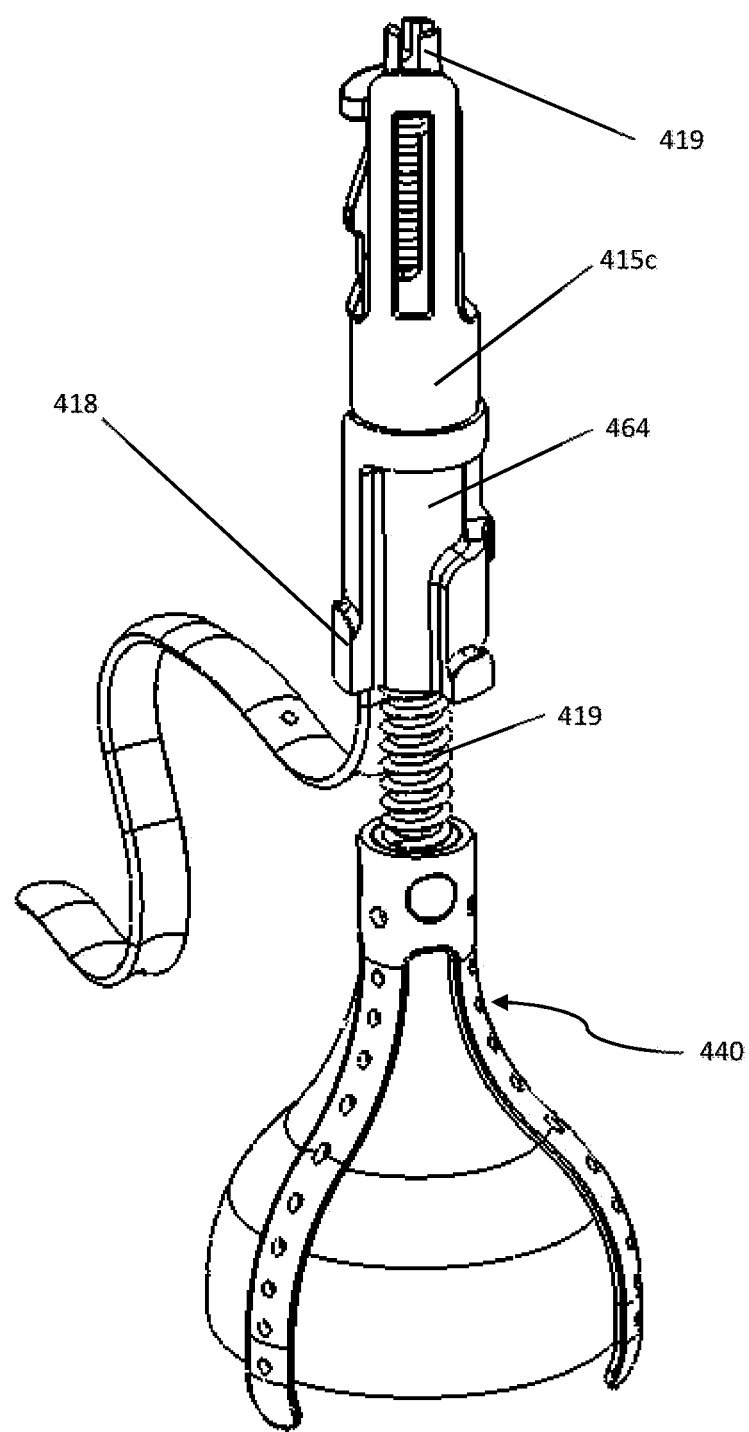
FIG. 22D is a schematic illustrating an exemplary embodiment of a commissures-anchored device in a deployed conformation with arms 415a and 415b not displayed to allow visualization of internal components of the Anchoring mechanism 410.

As shown in FIG. 22A, the arm 415a protrudes proximally in a cylindrical shape. Stated somewhat differently, the arm 415a includes a proximal end region that includes a cylindrical protrusion. The inner core 418 can sit within the cylindrical shape protruding from the arm 415a. As shown in FIG. 22A, snap-fit edge 421 on the inner core 418 is devised to mate with notch 422 of the arm 415a, axially interlocking the components while still allowing limited rotation of inner core 418 within the arm 415a. As shown in FIG. 22B and FIG. 22D, the arm 415b is mated to the inner core 418 within matching groove 464 defined on the inner core 418, allowing combined rotation of the arm 415b with inner core 418. As shown in FIG. 22C, the arm 415c protrudes proximally in a cylindrically-shaped central portion. The central portion of the arm 415c can be inserted on the inner core 418 by mating in a groove 423 defined on the inner core 418, allowing the arm 415a to be rotated independently from inner core 418. Clockwise (CW) and/or counterclockwise (CCW) rotations of arm 415b can be limited by the edges of groove 423 on the inner core 418 within which the central portion of the arm 415c is mated.

Figure 30A:
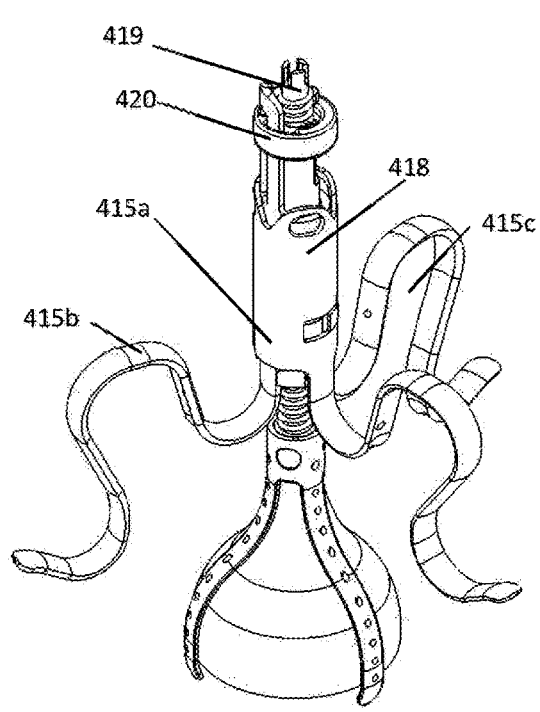
FIGS. 30A-30C are schematics of exemplary embodiments of a commissures-anchored device illustrating the anchoring arm 415b radial displacement functionality. The arm 415a is not displayed in FIGS. 30B and 30C to allow visualization of internal components of the anchoring mechanism 410.
Figure 30B:
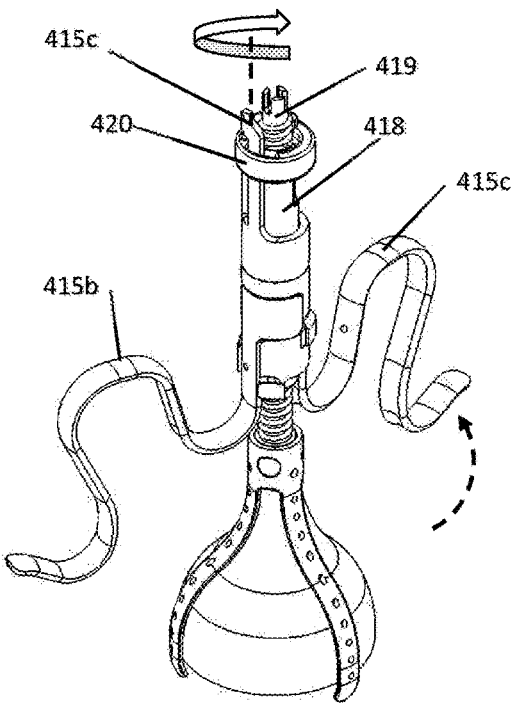
Figure 30C:
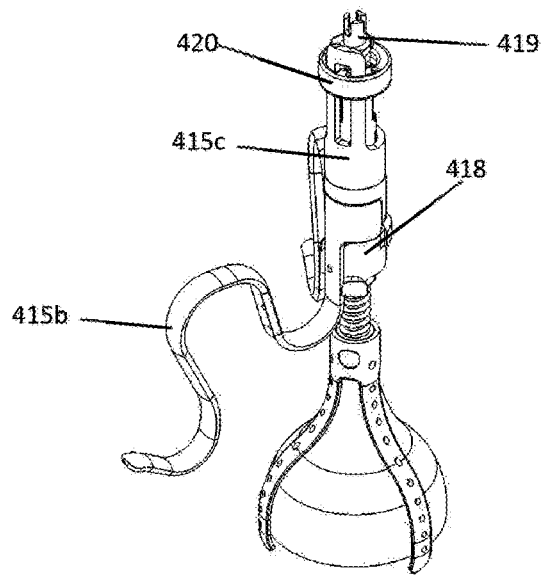
Figures 31A, 31B:
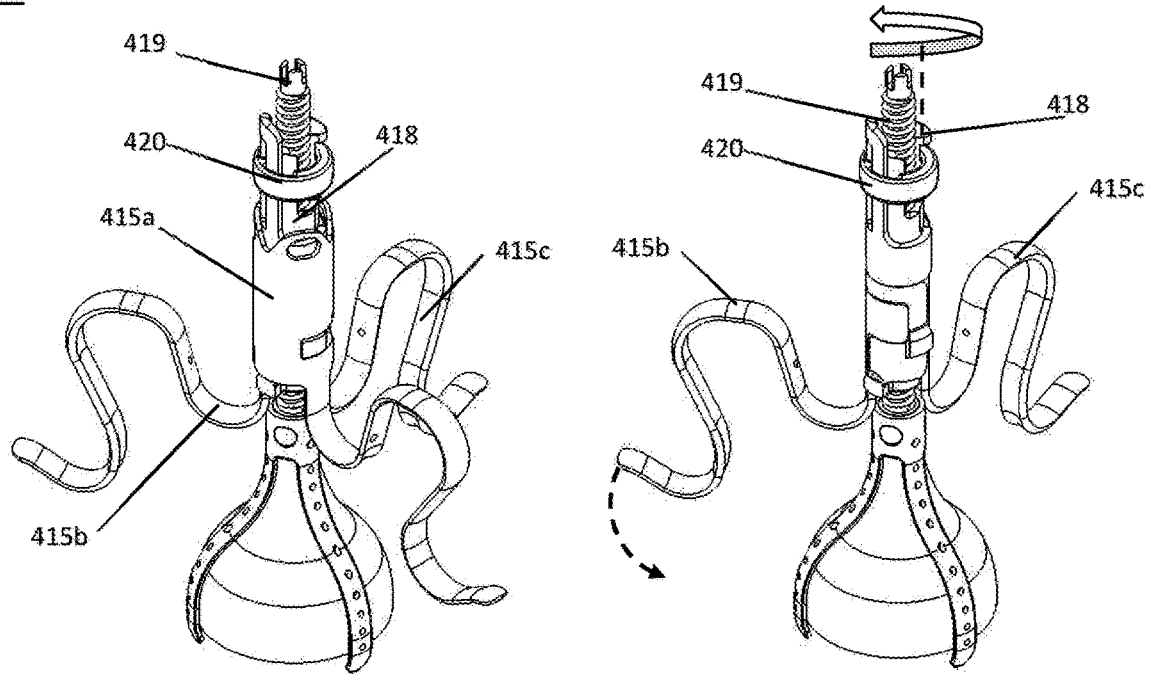
FIGS. 31A-31C are schematics of exemplary embodiments of a commissures-anchored device illustrating the anchoring arm 415c radial displacement functionality. Arm 415a is not displayed in FIGS. 31B and 31C to allow visualization of internal components of the anchoring mechanism 410.
Figure 31C:
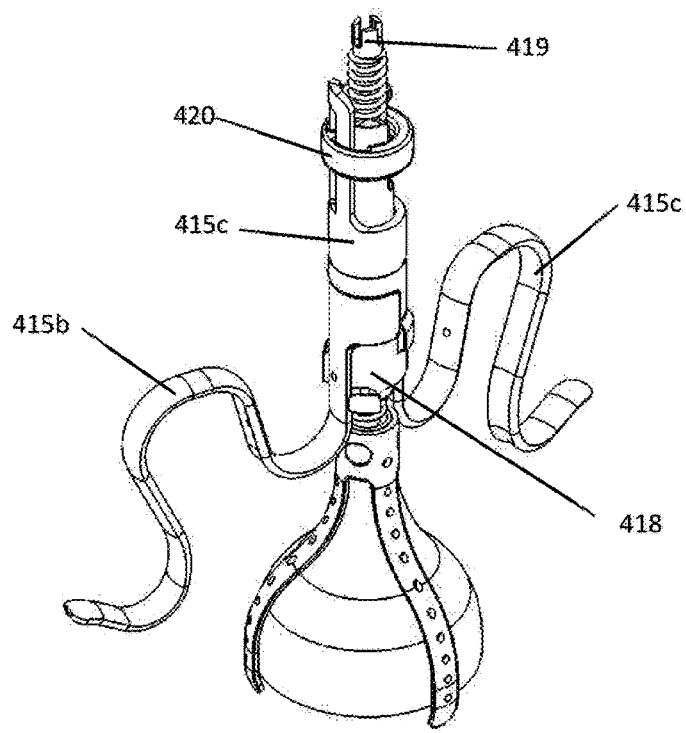
Figure 32A:
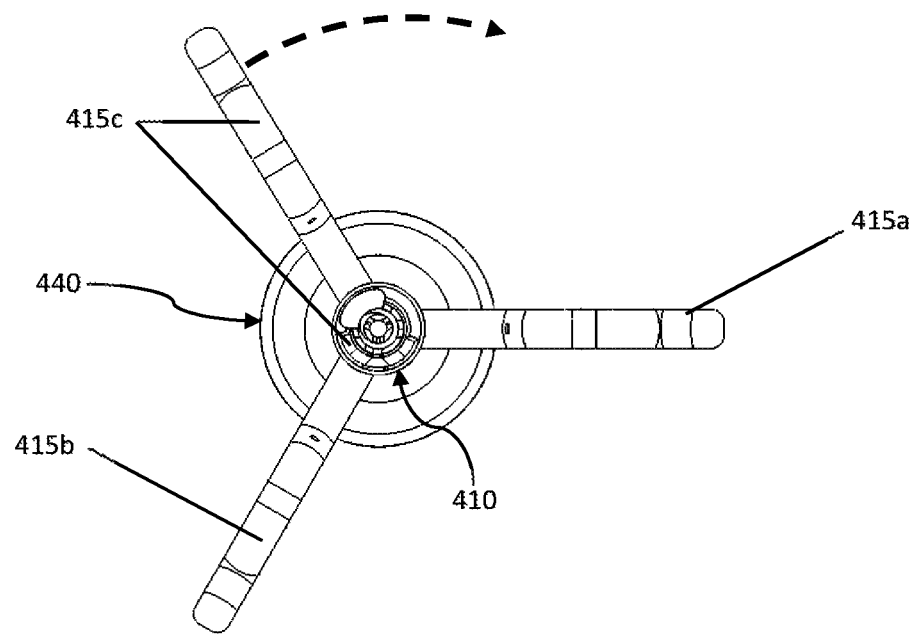
FIG. 32A is an atrial (top) view of an exemplary embodiment of a commissures-anchored device with anchoring arms 415 radially positioned in a symmetric configuration.
Figure 32B:
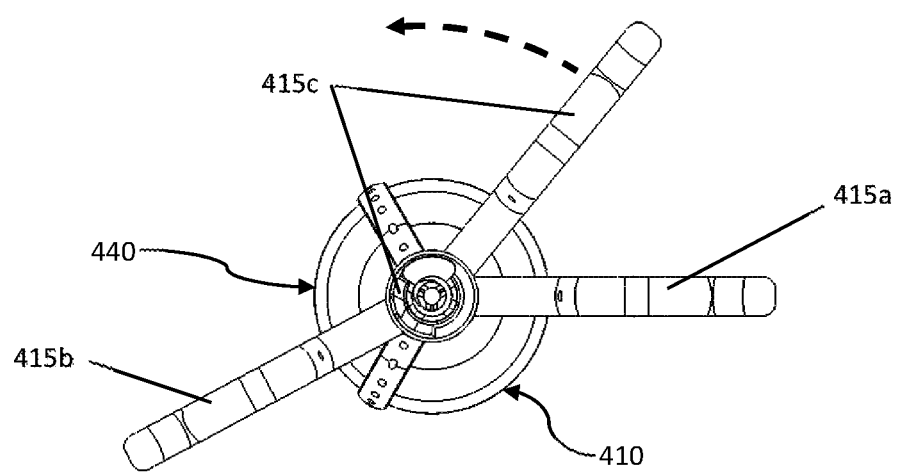
FIG. 32B is an atrial (top) view of an exemplary embodiment of a commissures-anchored device with the anchoring arms 415c radially displaced clockwise towards arm 415a starting from the position shown in FIG. 32A.
Figure 32C:
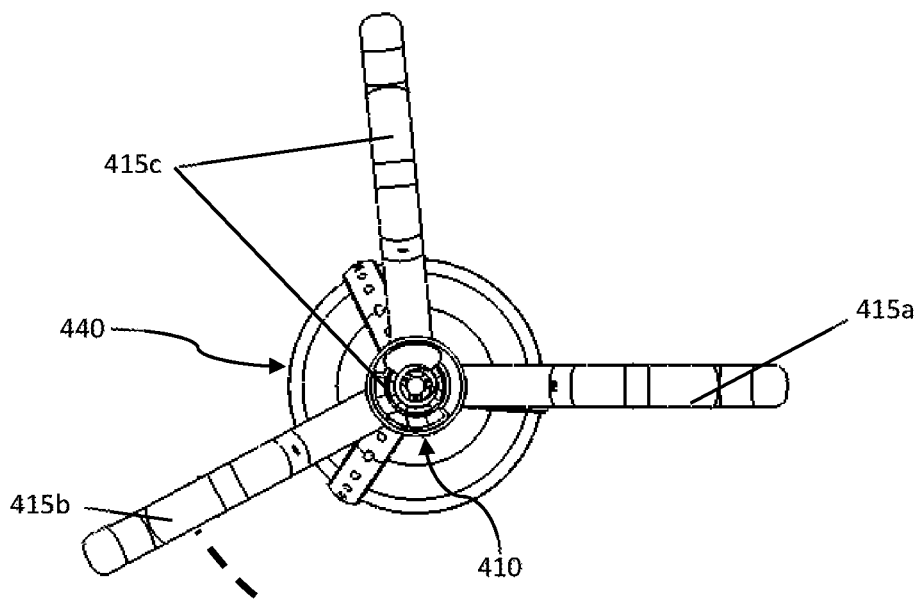
FIG. 32C is an atrial (top) view of an exemplary embodiment of a commissures-anchored device with the anchoring arms 415c radially displaced counterclockwise towards arm 415b starting from the position shown in FIG. 32B.
Figure 32D:
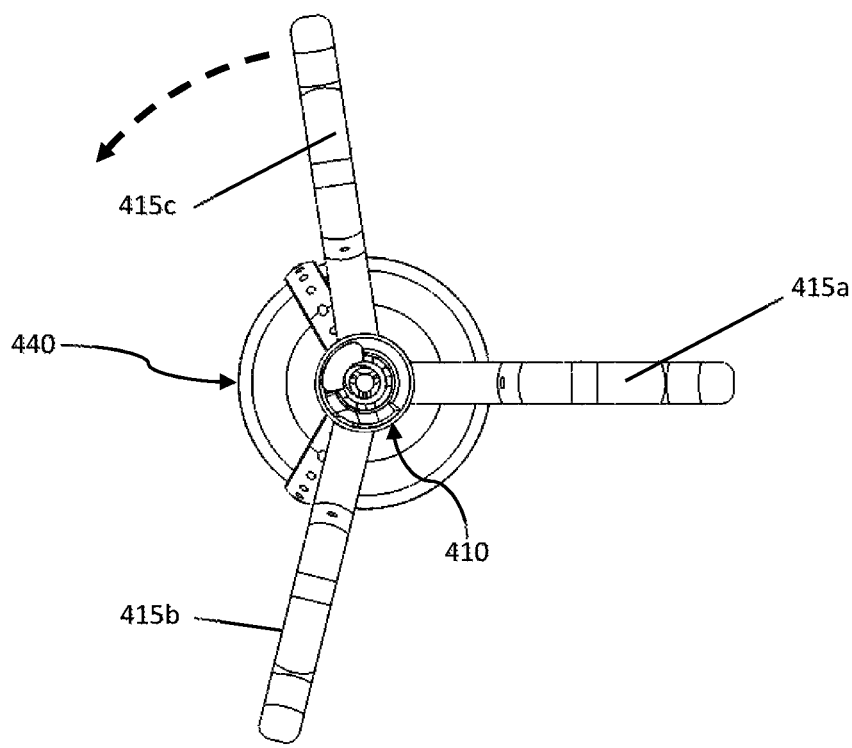
FIG. 32D is an atrial (top) view of an exemplary embodiment of a commissures-anchored device with the anchoring arm 415b radially displaced counterclockwise towards arm 415a starting from the position shown in FIG. 32C.

As shown in FIGS. 30A-30C, the arm 415c can be radially displaced by rotating CW or CCW a proximal end region of the arm 415c. The proximal end region of the arm 415c protrudes through the locking collar 420. Similarly, as shown in FIGS. 31A-31C, the arm 415b can be radially displaced by rotating clockwise or counterclockwise the proximal end region of the inner core 418 protruding along the threaded shaft 419. As shown in the atrial views in FIGS. 32A-32E, by rotating the proximal end regions of the inner core 418 and/or of the arm 415c, an operator can individually position arms 415a-415c at different relative angles, matching angles across the commissures of the leaflets of the patients' native tricuspid valves. The rotating arms 415a-415c can be performed pre-procedurally (for example, prior to loading of the device 400 into the delivery catheter), and/or intra-procedurally (for example, prior to loading of the device 400 into the delivery catheter) via the device's delivery system controls.

Figure 23A:
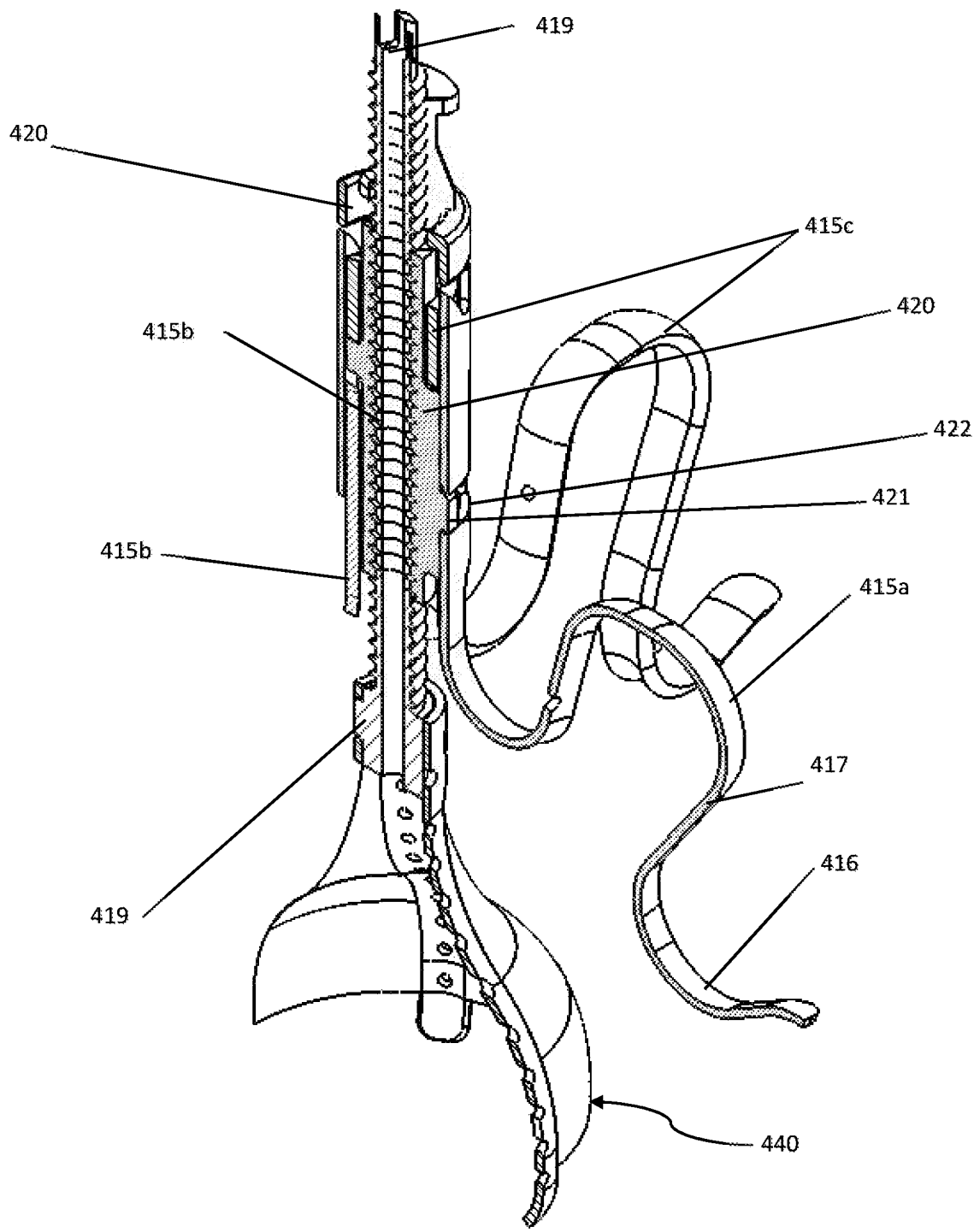
FIG. 23A is a schematic illustrating a longitudinal cross-section along arm 415a of an exemplary embodiment of a commissures-anchored device in a deployed conformation.
Figure 23B:
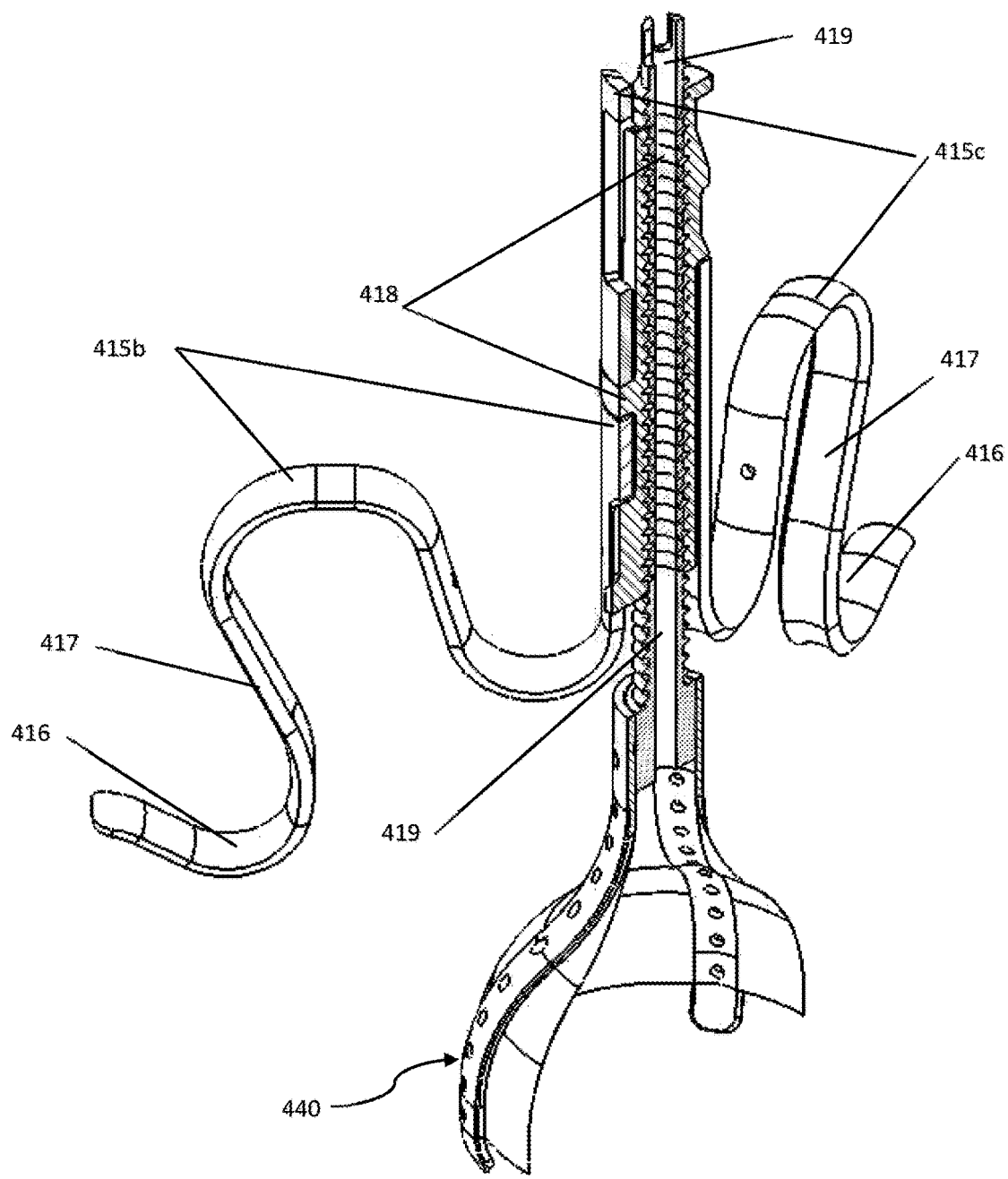
FIG. 23B is a schematic illustrating a longitudinal cross-section, orthogonal to the longitudinal cross-section shown in FIG. 23A, of an exemplary embodiment of a commissures-anchored device in a deployed conformation.

The threaded shaft 419 supports the flow optimizer 440 and is threaded through the inner core 418 as shown in FIG. 23A and FIG. 23B. As shown in FIGS. 33A-33B, CW and/or CCW rotations of the distal end region of the threaded shaft 419 can axially displace the distally-connected flow optimizer 440 in the distal and proximal longitudinal directions, allowing shortening or extending the relative distance between the flow optimizer 440 and commissures anchoring mechanism 410, and/or to change the radial orientation of the flow optimizer 440 relatively to the anchoring arms 415a-415c.

Figure 34A:
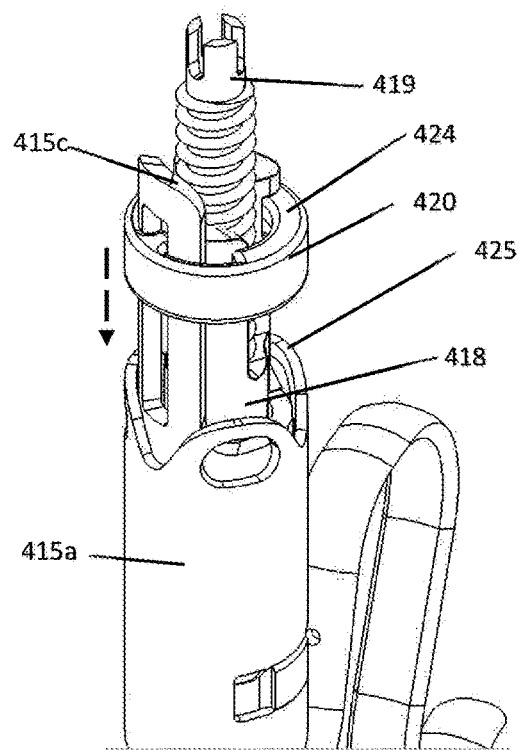
FIG. 34A is a close-up view of an exemplary embodiment of a commissures-anchored device with locking collar 420 disengaged.
Figure 34B:
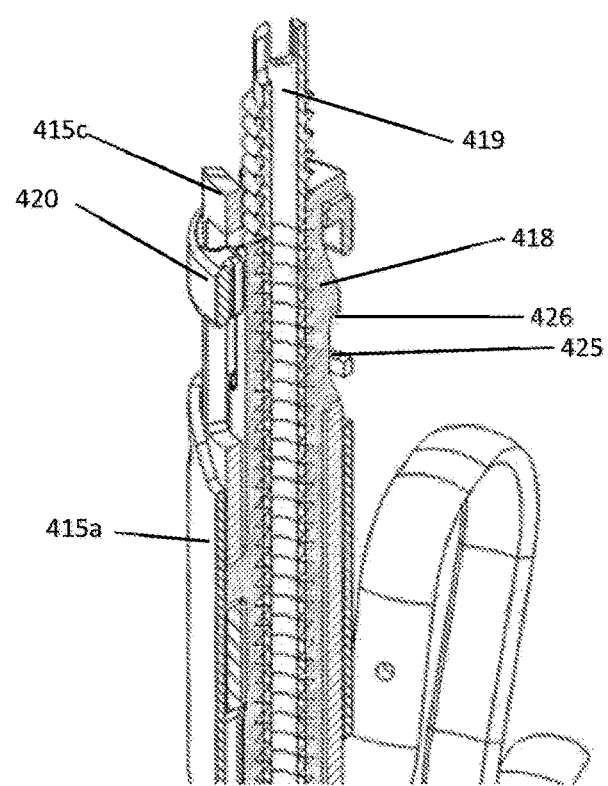
FIG. 34B is a longitudinal cross section view of an exemplary embodiment of a commissures-anchored device with locking collar 420 disengaged.
Figure 34C:
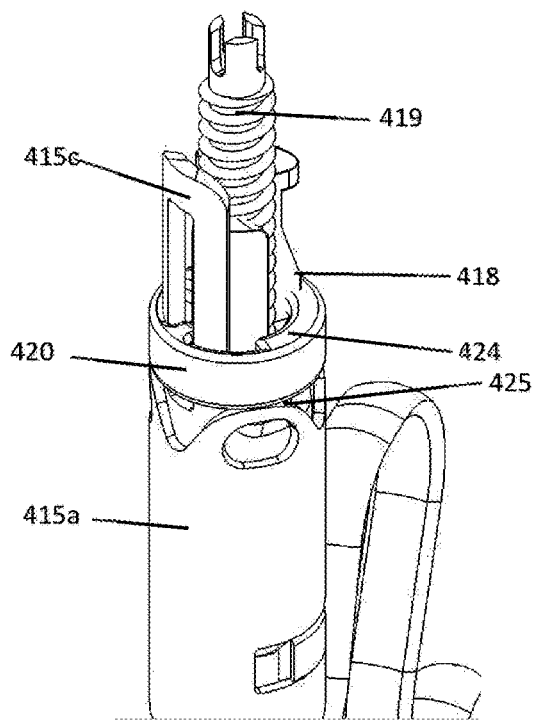
FIG. 34C is a close-up view of an exemplary embodiment of a commissures-anchored device 400 with locking collar 420 engaged.
Figure 34D:
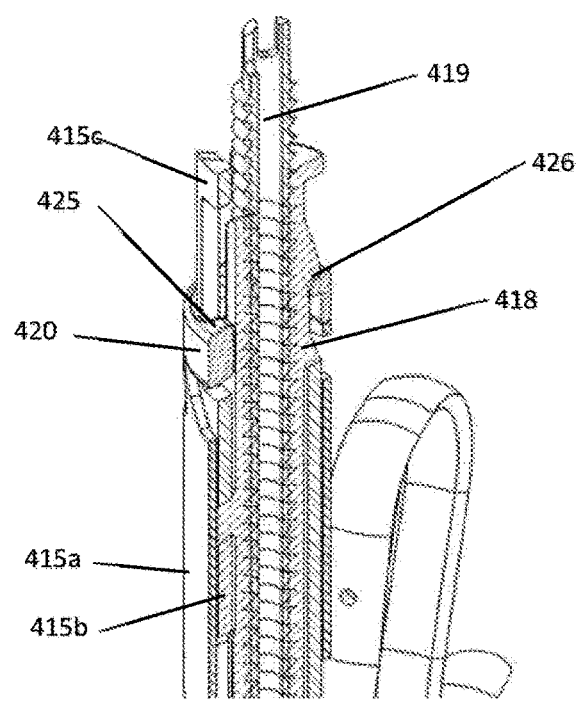
FIG. 34D is a longitudinal cross section view of a commissures-anchored device 400 with locking collar 420 engaged.
Figure 35:
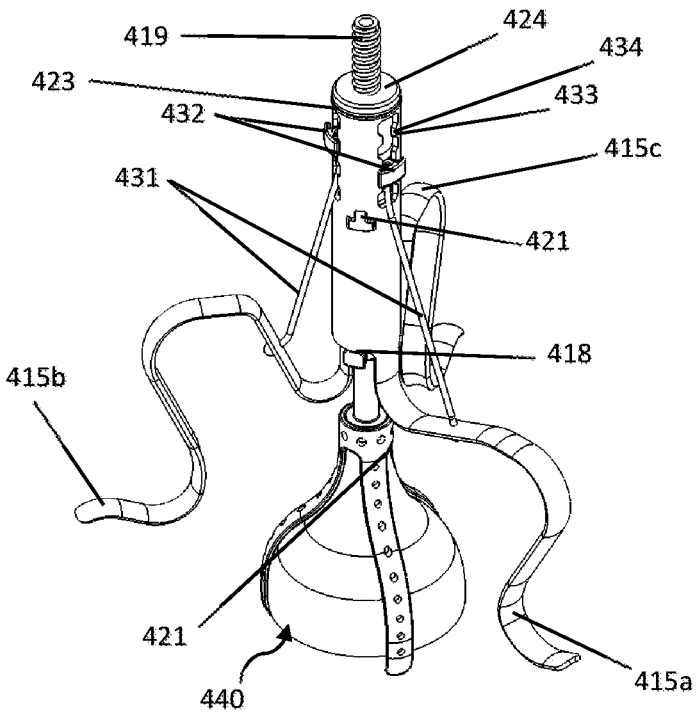
FIG. 35 is a schematic illustrating an exemplary embodiment of a commissures-anchored device in deployed conformation, with the anchoring mechanism 410 including the components to control independently expansion and/or retraction of each arm.
Figure 36:
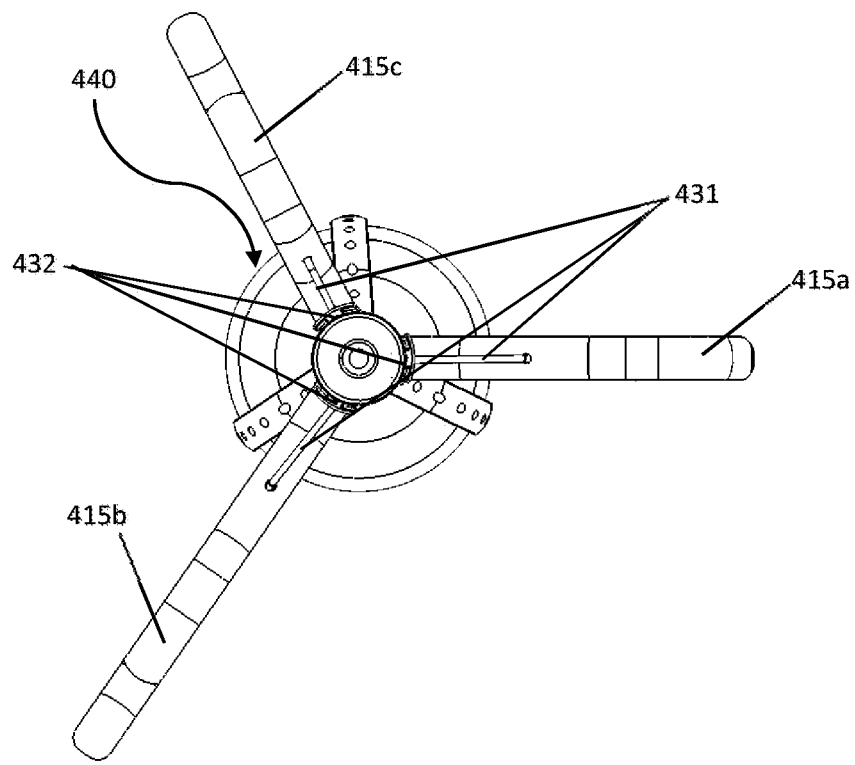
FIG. 36 is an atrial view illustrating an exemplary embodiment of a commissures-anchored device in deployed conformation, with the anchoring mechanism 410 including the components to control independently expansion and/or retraction of each arm.
Figure 37:
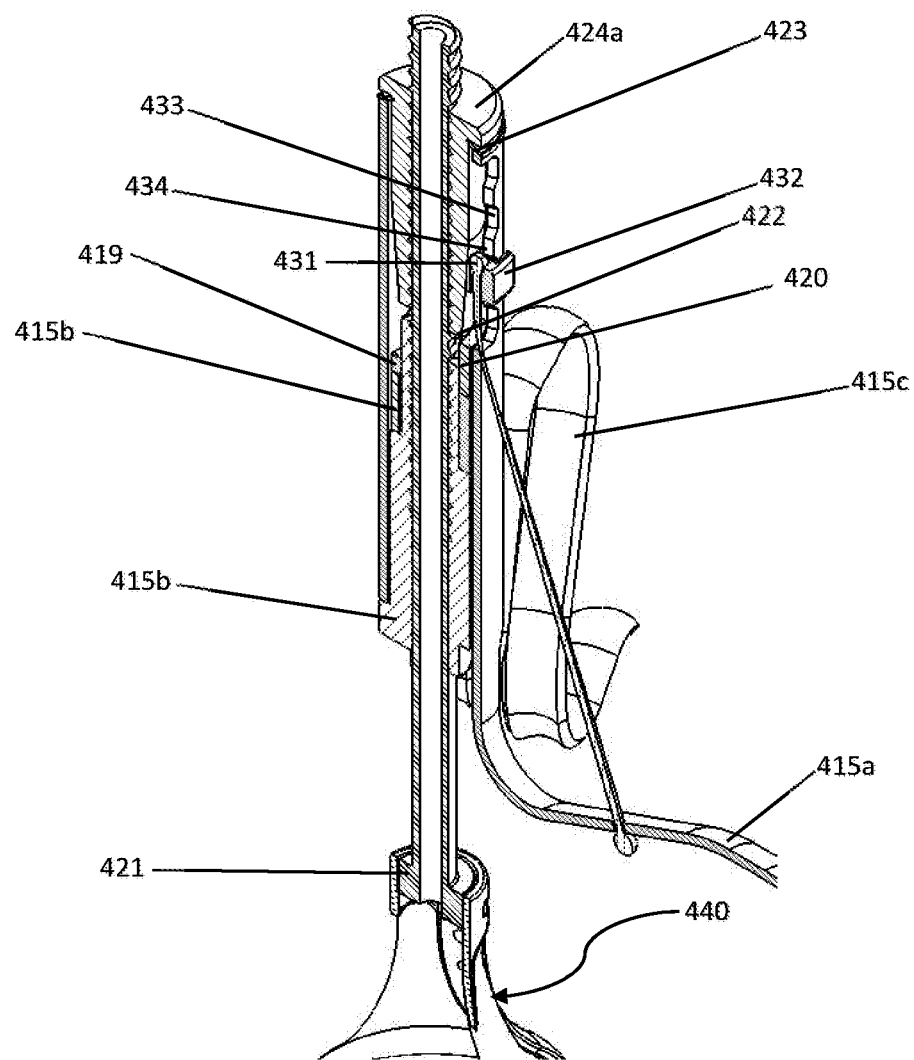
FIG. 37 a longitudinal cross-section illustrating an exemplary embodiment of a commissures-anchored device in deployed conformation, with the anchoring mechanism 410 including the components to control independently expansion and/or retraction of each arm.

The locking collar 420 is shown as sitting on the proximal end of the anchoring mechanism 410, over the inner core 418 and the arm 415c as shown in FIG. 34A and FIG. 34B. As shown in FIGS. 34C and 34D, the proximal surface 424 of the locking collar 420 can be displaced distally until being mated with a proximal cylindrical surface 425 of the arm 415a. The proximal surface 424 of the locking collar 420 can engage a snap-fit edge 426 of the inner core 418. In this position, the locking collar 420 compresses the arm 415a over the inner core 418, while radially constraining the arm 415c and the proximal ends of the inner core 418 over the threaded shaft 419, thus locking simultaneously the relative radial and axial positions of the inner core 418, the arms 415a-b-c and the threaded shaft 419.

Optionally, the commissures anchoring mechanism 410 can be coupled with a height adjustment mechanism to allow discrete individual control of the expansion or contraction of each arm 415. In one embodiment, illustrated in FIGS. 35-38, the end regions (or distal end regions) and/or the intermediate portions of the anchoring arms 415a-415c can be connected to cables 431. The proximal ends of the cable 431 are connected to sliders 432. The longitudinal cross-sectional profile of the sliders 432 is configured to mate with that of notches 433 cut along the cylindrical protrusion of the arm 415a. Expansion or contraction of the arms 415a-415c relative to the center axis of the anchoring mechanism can be individually controlled by longitudinally displacing distally or proximally the slider 432 along the arm 415a such that detents 434 disengage and re-engage with the sliders 432 as shown in FIGS. 39A-39B. In one embodiment, the detents 434 are configured to allow sliding in both distal and proximal directions. Optionally, unidirectional detents 434 are configured to allow translocation in either the distal direction (e.g. towards the ventricle) or the proximal direction (e.g. towards the atrium).

Deployment of Commissures/Atrial Wall Supported Device 400

Figure 40A:
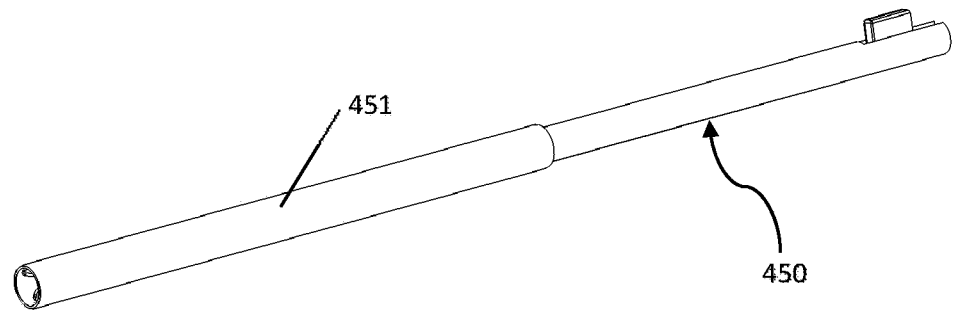
FIG. 40A is a schematic of an exemplary embodiment of a delivery system catheter for a commissures-anchored device.
Figure 40B:
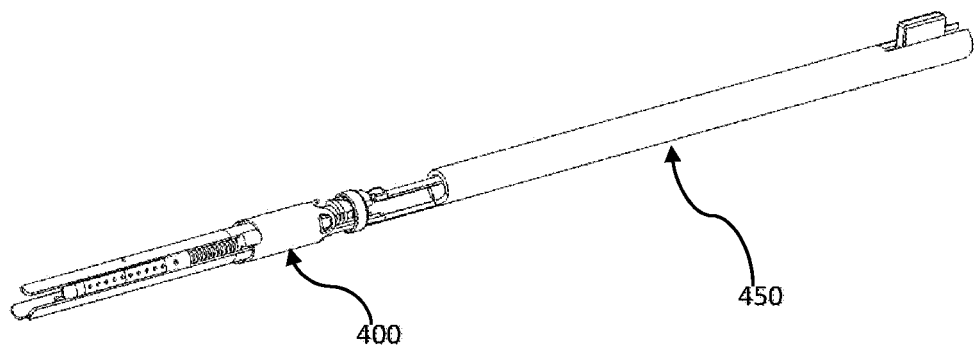
FIG. 40B is a schematic of a delivery system catheter shown in FIG. 40A with the outer layer 451 removed to show a commissures-anchored device in a loaded conformation.
Figure 41A:
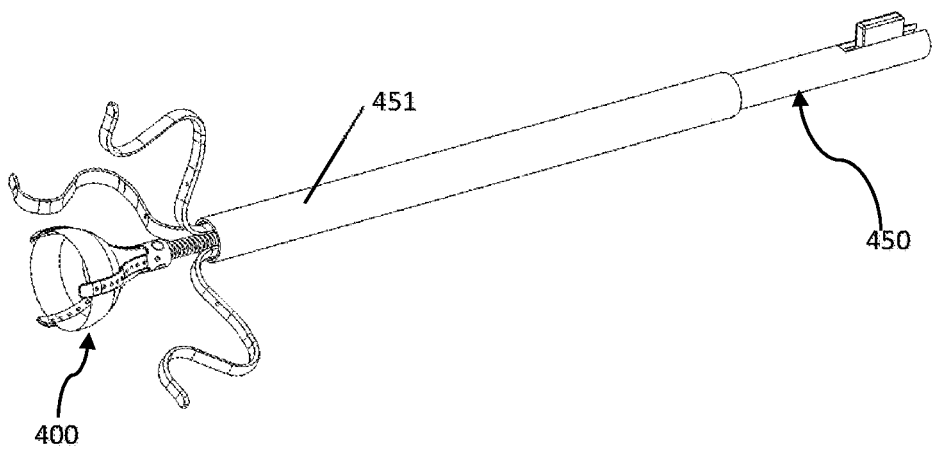
FIG. 41A is a schematic of an exemplary embodiment of a delivery system catheter with the outer layer 451 retracted and a commissures-anchored device in a deployed conformation.
Figure 41B:
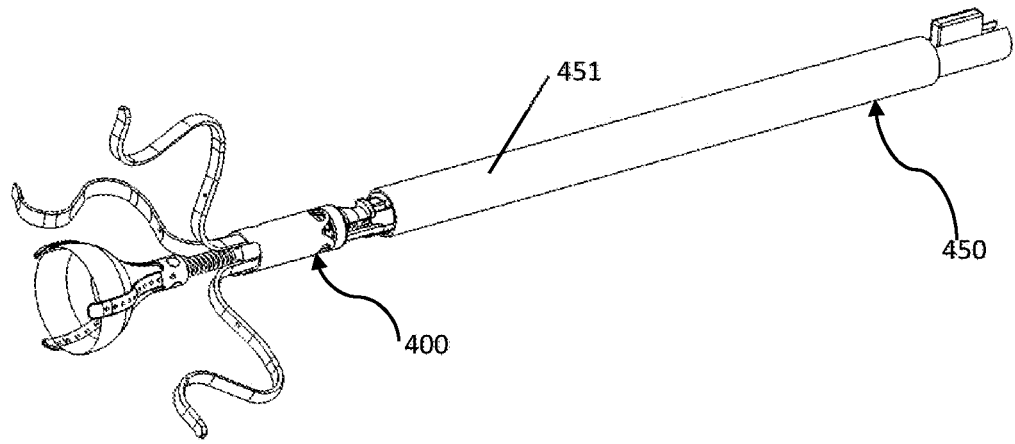
FIG. 41B is a schematic of an exemplary embodiment of a delivery system catheter with outer layer 451 removed and a commissures-anchored device in a deployed conformation.

Similarly to the deployment of the device 100, device 400 can be loaded within an intravascular catheter 450 as shown in FIGS. 40A and 40B, and delivered to the right atrium and into the tricuspid valve either via transfemoral access through the IVC, or via right internal jugular vein access of the IVC. Once positioned within the tricuspid valve, the distal end of outer lumen 451 can be partially retracted to allow the expansion of the flow optimizer 440 and partial opening of the anchoring arms 415 (shown in FIG. 41A).

Figure 42A:
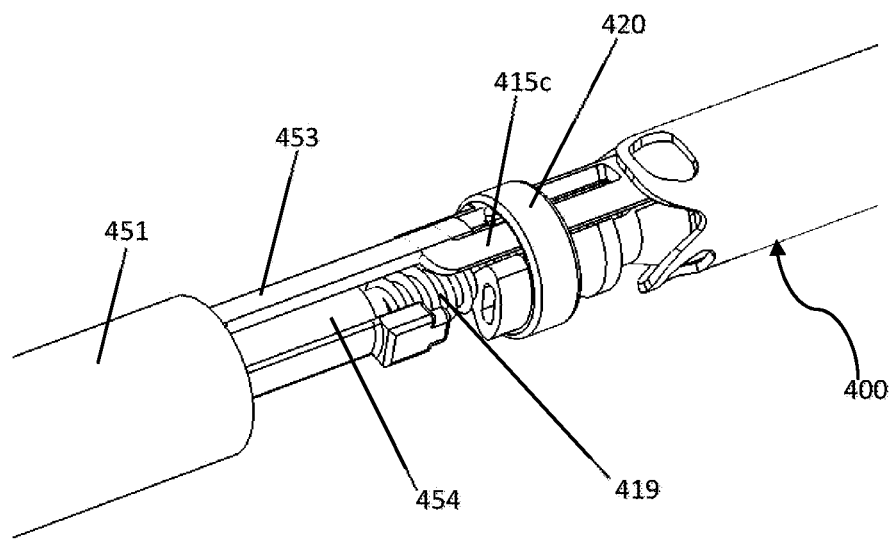
FIG. 42A is a close-up view of an exemplary embodiment of the connection mechanism between the distal end of a delivery catheter and the proximal end of a commissures-anchored device.
Figure 42B:
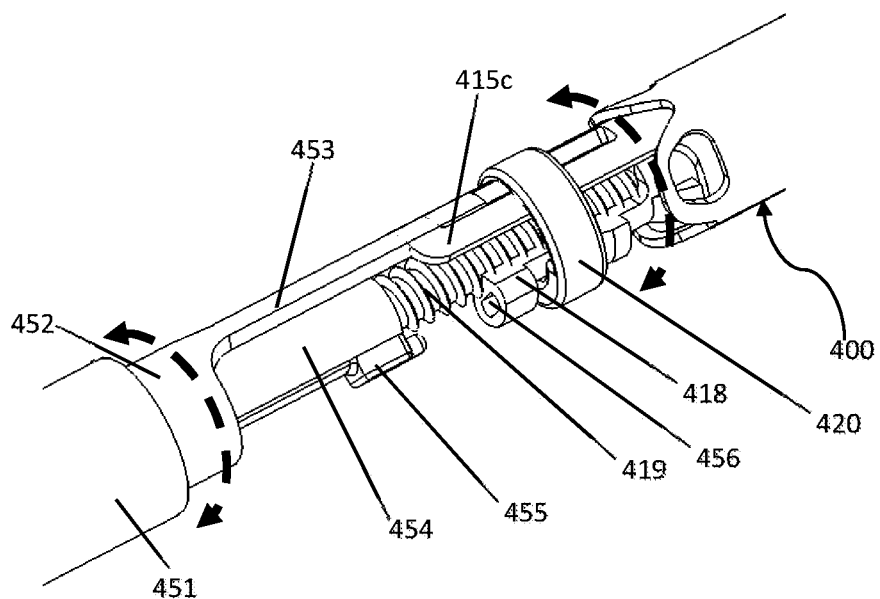
FIG. 42B is a close-up view of the schematic in FIG. 42A, showing the concurrent rotation of arm 415c of commissures-anchored device and mid lumen 452 of delivery system catheter.

Under standard visualization techniques (e.g., angiography, fluoroscopy, echocardiography), the radial position of the arm 415c can be modified by rotating CW or CCW the delivery system mid lumen 452 (shown in FIG. 42B). The mid lumen 452 is connected via the slider 453 (shown in FIG. 42A) to the proximal end of the Arm 415c.

Figure 43A:
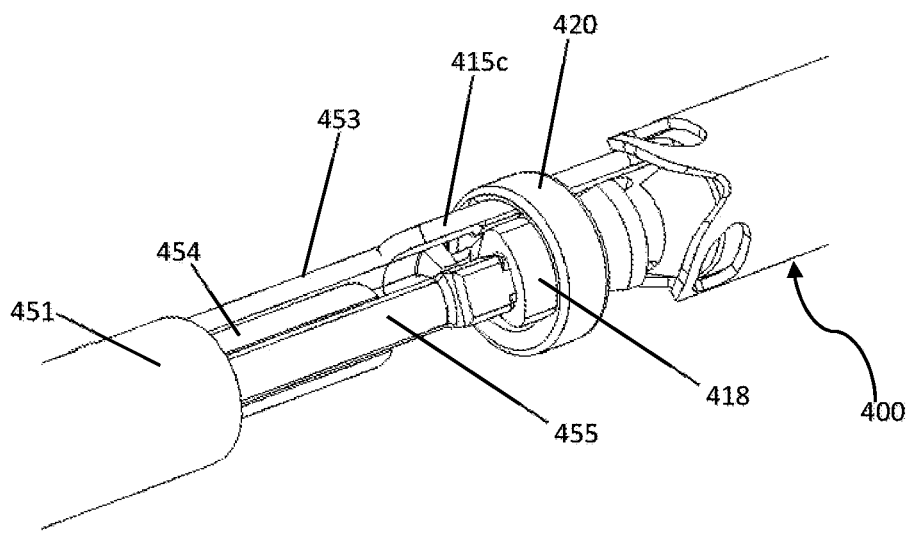
FIG. 43A is a close-up view of the connection between slider 455 of delivery system catheter and the inner core 418 of commissures-anchored device.
Figure 43B:
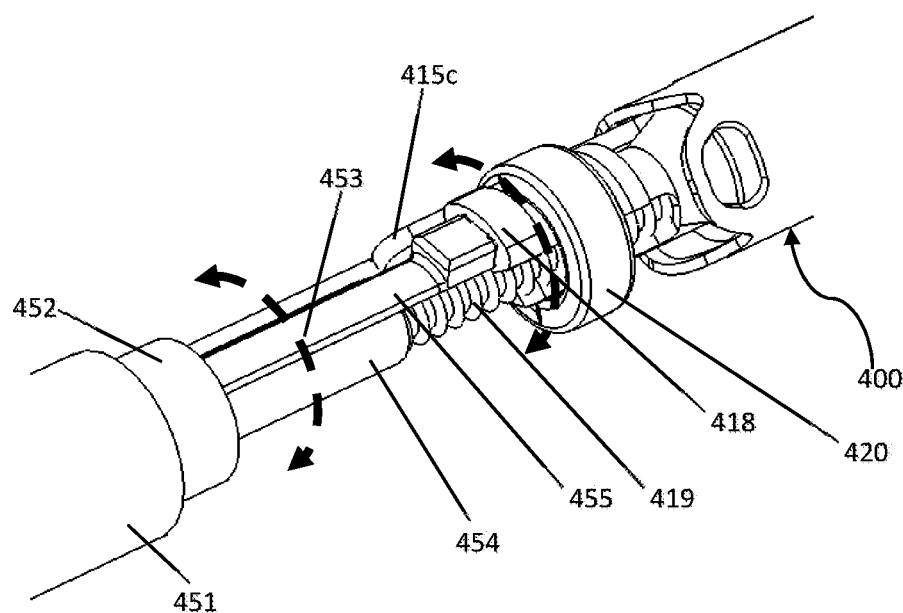
FIG. 43B is a close-up view of the schematic in FIG. 43A, showing the concurrent rotation of inner core 418 of commissures-anchored device and inner lumen 454 of delivery system catheter.

As shown in FIG. 43A, a slider 455 on an inner lumen 454 can be advanced to engage mating notch 456 at the distal end region of the inner core 418. As shown in FIG. 43B, the radial position of the arm 415b can be modified rotating CW or CCW the delivery system inner lumen 454.

Figure 44:
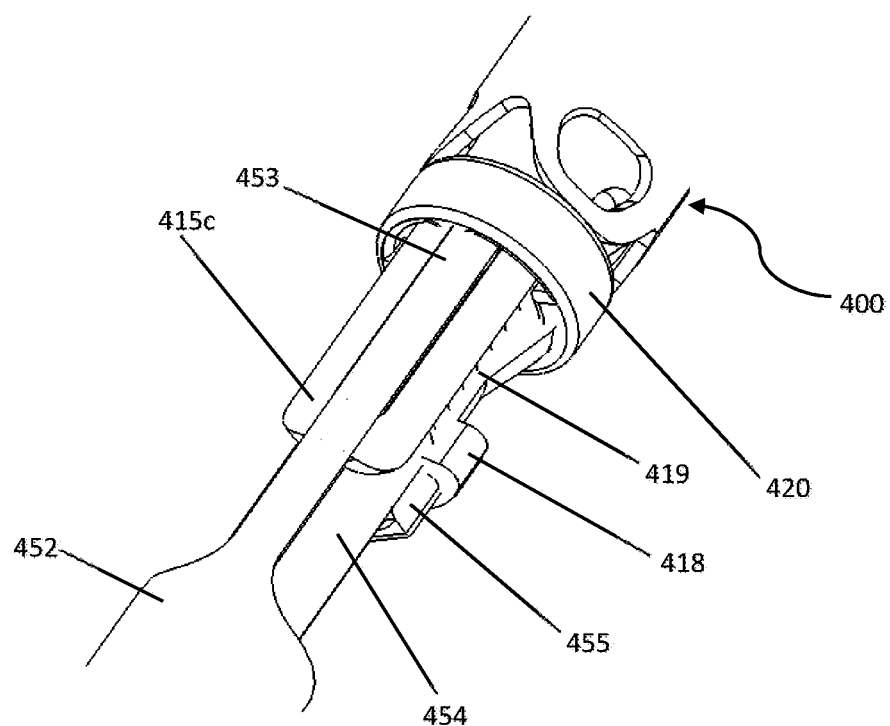
FIG. 44 is a close-up view of the connection mechanism between the distal end of a delivery catheter and the proximal end of commissures-anchored device, showing slider 453 distally advanced to activate locking collar 420.

Once the anchoring arms 415 have been aligned with commissures of leaflets of the native valve, the slider 455 on the inner lumen 454 can be retracted by the operator, thus disengaging the rotation control of Arm 415b, and then the height and orientation of the flow optimizer 440 can be modified by rotating CW or CCW the inner lumen 454. As shown in FIG. 44, locking the positions of the anchoring arms and of flow optimizer 440 can be achieved by sliding distally the slider 453 and advancing the locking collar 420 until is mated with the arm 415a.

Figure 45A:
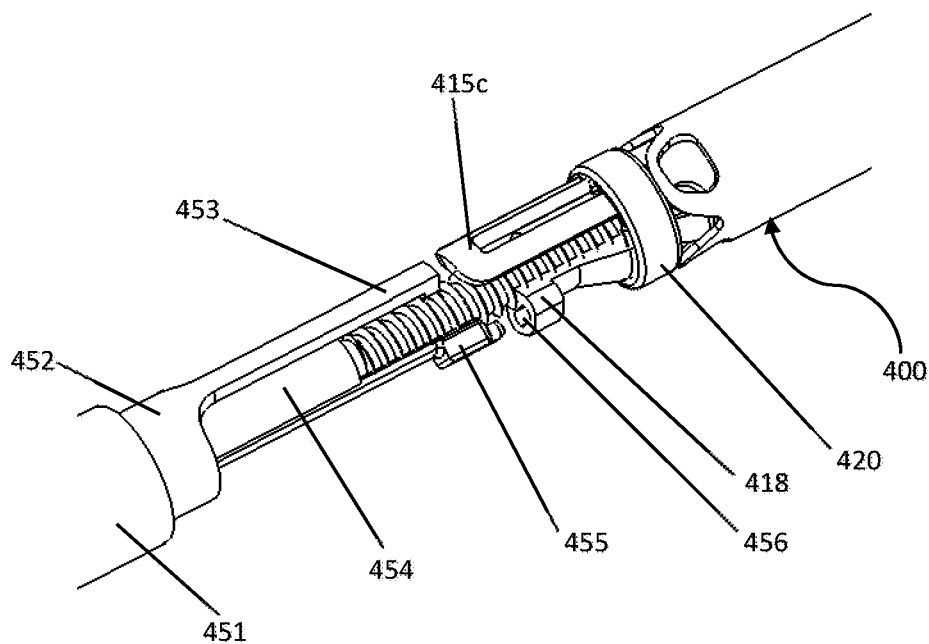
FIG. 45A is a close-up view of the connection mechanism between the distal end of a delivery catheter and the proximal end of commissures-anchored device, showing slider 453 and slider 455 disconnected respectively from arm 415c and inner core 418.
Figure 45B:
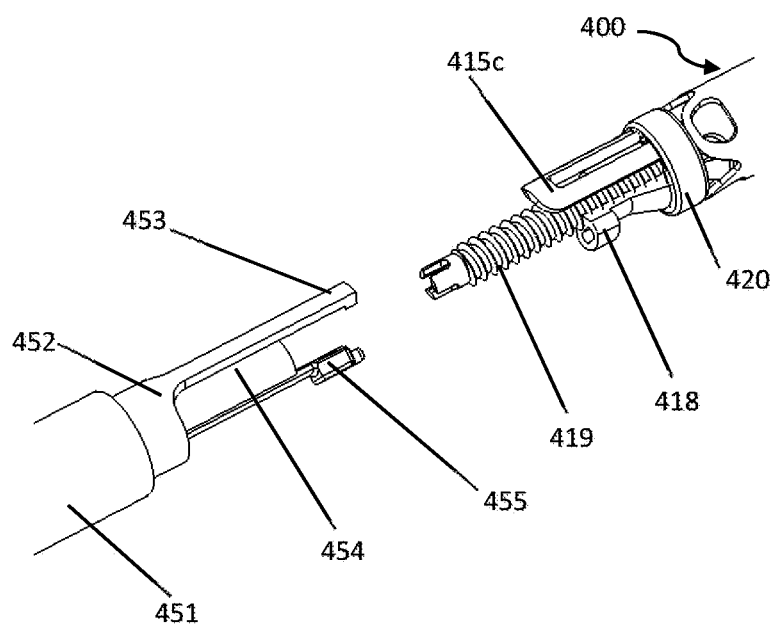
FIG. 45B is a close-up view of the connection mechanism between the distal end of a delivery catheter and the proximal end of commissures-anchored device, showing slider 453, slider 455 and inner lumen 454 disconnected respectively from arm 415c, inner core 418, and threaded shaft 419.

The outer lumen 451 can be further retrieved to allow the anchoring arms 415 to fully reach the annulus of the tricuspid valve at the commissures of the leaflets and/or at the supra-annular wall of the right atrium. As shown in FIGS. 45A-45B, the catheter operator can rotate (for example, CCW) the inner lumen 454 to disengage the threaded shaft 419, allowing release of the device and retrieval of the delivery system catheter. Optionally, an additional outer lumen (not shown) with three separate sliders (not shown) can be added to the delivery system to allow the operator to modify the position of the sliders 432 (shown in FIGS. 39A-39B), and thus controlling the expansion and/or contraction of each individual anchoring arm 415.

The disclosed embodiments are susceptible to various modifications and alternative forms, and specific examples thereof have been shown by way of example in the drawings and are herein described in detail. It should be understood, however, that the disclosed embodiments are not to be limited to the particular forms or methods disclosed, but to the contrary, the disclosed embodiments are to cover all modifications, equivalents, and alternatives.

What is claimed is:

1. A method of assisting a valve of a heart, comprising:
   implanting a flow optimizer into a native cardiac valve orifice;
   during diastole, reducing a cross-sectional area of the flow optimizer to allow hemodynamic flow around and through the flow optimizer; and
   during systole, increasing a cross-sectional area of the flow optimizer to seal the cardiac valve orifice.

2. The method of claim 1, wherein reducing a cross-sectional area comprises moving a leaflet of the flow optimizer to a concave shape to allow hemodynamic flow around the flow optimizer.

3. The method of claim 1, wherein reducing a cross-sectional area comprises forming a gap between overlapping circumferential leaflet layers of the flow optimizer to allow hemodynamic flow through the flow optimizer.

4. The method of claim 3, wherein a first layer of the overlapping circumferential leaflet layers is positioned towards an atrium and wherein a second layer of the overlapping circumferential leaflet layers is positioned towards a ventricle.

5. The method of claim 4, wherein the second layer is positioned radially outwards of the first layer such that the gap is formed between an atrial end of the second layer and a ventricular end of the first layer.

6. The method of claim 3, wherein increasing a cross-sectional area comprises closing the gap between the overlapping circumferential layers.

7. The method of claim 1, wherein increasing a cross-sectional area comprises inflating leaflets of the flow optimizer towards native cardiac valve leaflets during systole.

8. The method of claim 1, further comprising anchoring the flow optimizer in the native cardiac valve orifice at commissures of native cardiac valve leaflets.

9. The method of claim 1, further comprising anchoring the flow optimizer in the native cardiac valve orifice by expanding an anchoring mechanism attached to the flow optimizer.

10. The method of claim 1, wherein the cardiac valve is a tricuspid valve.

11. The method of claim 9, further comprising adjusting a vertical position of the anchoring mechanism relative to the flow optimizer.

12. The method of claim 9, wherein expanding an anchoring mechanism attached to the flow optimizer comprises expanding a plurality of anchoring arms at commissures of native cardiac valve leaflets.

13. The method of claim 12, further comprising rotating one or more of the plurality of anchoring arms to position the anchoring arms relative to one another.

14. The method of claim 12, further comprising rotating the flow optimizer relative to the plurality of anchoring arms.

15. The method of claim 12, further comprising individually expanding or contracting one of the plurality of anchoring arms.

16. The method of claim 12, further comprising locking a position of the plurality of anchoring arms.

17. The method of claim 12, further comprising locking a position of the flow optimizer relative to the plurality of anchoring arms.

18. The method of claim 1, further comprising advancing the flow optimizer through a catheter to the valve of the heart.

* * * * *